US006983177B2

(12) United States Patent
Rule et al.

(10) Patent No.: US 6,983,177 B2
(45) Date of Patent: Jan. 3, 2006

(54) LAYERED SPECTROSCOPIC SAMPLE ELEMENT WITH MICROPOROUS MEMBRANE

(75) Inventors: Peter Rule, Los Altos Hills, CA (US); James R. Braig, Piedmont, CA (US); Philip C. Hartstein, Palo Alto, CA (US)

(73) Assignee: Optiscan Biomedical Corporation, Alameda, CA (US)

( * ) Notice: Subject to any disclaimer, the term of this patent is extended or adjusted under 35 U.S.C. 154(b) by 13 days.

(21) Appl. No.: 10/337,226

(22) Filed: Jan. 6, 2003

(65) Prior Publication Data

US 2004/0133084 A1  Jul. 8, 2004

(51) Int. Cl.
  *A61B 5/00* (2006.01)
(52) U.S. Cl. .................................... 600/310
(58) Field of Classification Search ........... 600/310, 600/573, 583, 584; 436/164, 171; 250/339.07, 250/576; 422/58, 102, 82.09; 356/38, 244, 356/246, 300, 319, 326, 440
See application file for complete search history.

(56) References Cited

U.S. PATENT DOCUMENTS

| 4,042,335 A | 8/1977 | Clement |
| 4,088,448 A | 5/1978 | Lilja et al. |
| 4,440,301 A | 4/1984 | Intengan |
| 4,465,929 A | 8/1984 | Edgar |
| 4,477,190 A | 10/1984 | Liston et al. |
| 4,654,197 A | 3/1987 | Lilja et al. |
| 4,756,884 A | 7/1988 | Hillman et al. |
| 4,787,398 A | 11/1988 | Garcia et al. |
| 4,790,640 A | 12/1988 | Nason |
| 4,873,993 A | 10/1989 | Meserol et al. |
| 4,900,666 A | 2/1990 | Phillips |
| 4,935,346 A | 6/1990 | Phillips et al. |
| 4,953,552 A | 9/1990 | DeMarzo |
| 5,004,923 A | 4/1991 | Hillman et al. |
| 5,029,583 A | 7/1991 | Meserol et al. |
| 5,049,478 A | 9/1991 | Koch et al. |
| 5,109,850 A | 5/1992 | Blanco et al. |
| 5,128,171 A | 7/1992 | Gleisner |
| 5,165,418 A | 11/1992 | Tankovich |
| 5,204,525 A | 4/1993 | Hillman et al. |

(Continued)

FOREIGN PATENT DOCUMENTS

EP  0 725 275 B1  1/1996

(Continued)

OTHER PUBLICATIONS

Heise et al., "Multicomponent Assay for Blood Substrates in Human Plasma by Mid-Infrared Spectroscopy and its Evaluation for Clinical Analysis," *Applied Spectroscopy*, vol. 48, No. 1, pp. 85-95 (1994).

(Continued)

*Primary Examiner*—Eric F. Winakur
(74) *Attorney, Agent, or Firm*—Knobbe, Martens, Olson & Bear LLP

(57) ABSTRACT

A spectroscopic sample holder comprises a microporous sheet. The microporous sheet has a top surface, a bottom surface substantially parallel to the top surface, and at least one side surface oriented substantially perpendicular to the top and bottom surfaces. The side surface forms an exposed transit opening configured to contact a material sample and distribute the contacted material sample into the microporous sheet. The spectroscopic sample holder further comprises a first planar support member positioned on, and substantially parallel to, the top surface of the microporous sheet. The spectroscopic sample holder further comprises a second planar support member positioned on the bottom surface of the microporous sheet, and oriented substantially parallel to the first planar support member.

115 Claims, 27 Drawing Sheets

U.S. PATENT DOCUMENTS

| | | |
|---|---|---|
| 5,209,904 A | 5/1993 | Forney et al. |
| 5,223,219 A | 6/1993 | Subramanian et al. |
| 5,249,584 A | 10/1993 | Karkar et al. |
| 5,279,791 A | 1/1994 | Aldrich et al. |
| 5,286,454 A | 2/1994 | Nilsson et al. |
| 5,300,779 A | 4/1994 | Hillman et al. |
| 5,364,744 A | 11/1994 | Buican et al. |
| 5,371,020 A | 12/1994 | Brischauf |
| 5,418,142 A | 5/1995 | Kiser et al. |
| 5,430,542 A | 7/1995 | Shepherd |
| 5,452,716 A | 9/1995 | Clift |
| 5,470,757 A | 11/1995 | Gagnon et al. |
| 5,515,847 A | 5/1996 | Braig et al. |
| 5,547,702 A | 8/1996 | Gleisner |
| 5,567,869 A | 10/1996 | Hauch et al. |
| 5,582,184 A | 12/1996 | Erickson et al. |
| 5,620,863 A | 4/1997 | Tomasco et al. |
| 5,636,640 A | 6/1997 | Staehlin |
| 5,643,252 A | 7/1997 | Waner et al. |
| 5,700,695 A | 12/1997 | Yassinzadeh et al. |
| 5,707,799 A | 1/1998 | Hansmann et al. |
| 5,736,103 A | 4/1998 | Pugh |
| 5,753,452 A | 5/1998 | Smith |
| 5,776,078 A | 7/1998 | Wardlaw |
| 5,789,255 A | 8/1998 | Yu |
| 5,801,057 A | 9/1998 | Smart et al. |
| 5,815,258 A | 9/1998 | Nakanishi |
| 5,843,692 A | 12/1998 | Phillips et al. |
| 5,857,983 A | 1/1999 | Douglas et al. |
| 5,879,311 A | 3/1999 | Duchon et al. |
| 5,882,935 A | 3/1999 | Hirai et al. |
| 5,885,211 A | 3/1999 | Eppstein et al. |
| 5,900,632 A | 5/1999 | Sterling et al. |
| 5,912,114 A | 6/1999 | Hutchinson et al. |
| 5,922,530 A | 7/1999 | Yu |
| 5,948,695 A | 9/1999 | Douglas et al. |
| 5,951,492 A | 9/1999 | Douglas et al. |
| 5,951,493 A | 9/1999 | Douglas et al. |
| 5,963,335 A | 10/1999 | Boutelle |
| 5,964,718 A | 10/1999 | Duchon et al. |
| 5,965,453 A | 10/1999 | Skiffington et al. |
| 5,968,765 A | 10/1999 | Grage et al. |
| 5,971,941 A | 10/1999 | Simons et al. |
| 6,001,239 A | 12/1999 | Douglas et al. |
| 6,030,399 A | 2/2000 | Ignotz et al. |
| 6,036,924 A | 3/2000 | Simons et al. |
| 6,048,352 A | 4/2000 | Douglas et al. |
| 6,049,762 A | 4/2000 | Ganz et al. |
| 6,071,251 A | 6/2000 | Cunningham et al. |
| 6,071,294 A | 6/2000 | Simons et al. |
| 6,072,180 A | 6/2000 | Kramer et al. |
| 6,084,660 A | 7/2000 | Shartle |
| 6,086,545 A | 7/2000 | Roe et al. |
| 6,087,182 A | 7/2000 | Jeng et al. |
| 6,132,449 A | 10/2000 | Lum et al. |
| 6,162,639 A | 12/2000 | Douglas |
| 6,197,494 B1 | 3/2001 | Oberhardt |
| 6,198,949 B1 | 3/2001 | Braig et al. |
| 6,231,531 B1 | 5/2001 | Lum et al. |
| 6,245,215 B1 | 6/2001 | Douglas et al. |
| 6,248,067 B1 | 6/2001 | Causet, III et al. |
| 6,251,083 B1 * | 6/2001 | Yum et al. ............. 600/584 |
| 6,261,245 B1 | 7/2001 | Kawai et al. |
| 6,261,519 B1 | 7/2001 | Harding et al. |
| 6,285,448 B1 | 9/2001 | Kuenstner |
| 6,312,888 B1 | 11/2001 | Wong et al. |
| 6,315,738 B1 | 11/2001 | Nishikawa et al. |
| 6,424,847 B1 | 7/2002 | Mastrototaro et al. |
| 6,562,014 B2 | 5/2003 | Lin et al. |
| 6,579,690 B1 | 6/2003 | Bonnecaze et al. |
| 6,591,124 B2 | 7/2003 | Sherman et al. |
| 6,679,841 B2 | 1/2004 | Bojan et al. |
| 6,836,332 B2 | 12/2004 | Mosley et al. |
| 6,837,988 B2 | 1/2005 | Leong et al. |
| 2003/0090649 A1 | 5/2003 | Sterling et al. |

FOREIGN PATENT DOCUMENTS

| | | |
|---|---|---|
| WO | WO 93/00580 | 1/1993 |
| WO | WO 93/20939 | 10/1993 |
| WO | WO 96/07919 | 3/1996 |
| WO | WO 00/40150 | 12/1999 |
| WO | WO 00/29847 | 5/2000 |
| WO | WO 01/35820 A1 | 11/2000 |
| WO | WO 01/26813 A2 | 4/2001 |
| WO | WO 01/53806 A1 | 7/2001 |
| WO | WO 03/016882 A1 | 7/2002 |

OTHER PUBLICATIONS

McNichols et al., "Optical Glucose Sensing in Biological Fluids: An Overview," *Journal of Biomedical Optics*, vol. 5, No. 1, pp. 5-9 (Jan. 2000).

Petibois et al., "Glucose and Lactate Concentration Determination on Single Microsamples by Fourier-Transform Infrared Spectroscopy," *Journal of Laboratory and Clinical Medicine*, vol. 135, No. 2, pp. 210-215 (Feb. 2000).

Ward et al., "Post-Prandial Blood Glucose Determination by Quantitative Mid-Infrared Spectroscopy," *Applied Spectroscopy*, vol. 46, No. 6, pp. 959-965 (1992).

Wilson, "Measurement of Tissue Optical Properties: Methods and Theories," in *Optical-Thermal Response of Laser-Irradiated Tissue*, edited by Ashley J. Welch et al., Plenum Press, pp. 233-274 (1995).

* cited by examiner

LAYERED SPECTROSCOPIC SAMPLE ELEMENT WITH MICROPOROUS MEMBRANE

BACKGROUND OF THE INVENTION

1. Field of the Invention

This invention relates generally to determining analyte concentrations in material samples.

2. Description of the Related Art

Millions of diabetics draw samples of bodily fluid such as blood on a daily basis to monitor the level of glucose in their bloodstream. This practice is called self monitoring, and is commonly performed using one of a number of reagent based glucose monitors. These monitors measure glucose concentration by observing some aspect of a chemical reaction between a reagent and the glucose in the fluid sample. The reagent is a chemical compound that is known to react with glucose in a predictable manner, enabling the monitor to determine the concentration of glucose in the sample. For example, the monitor can be configured to measure a voltage or a current generated by the reaction between the glucose and the reagent. A small test strip is often used to hold the reagent and to host the reaction between the glucose and the reagent. Reagent based monitors and test strips suffer from a variety of problems and also have limited performance.

Problems and costs relating to reagent arise during manufacture, shipment, storage and use of the reagent containing test strips. Costly and demanding quality control strategies must be incorporated into the test strip manufacturing processes to assure that the strips ultimately function properly. For example, a manufacturing lot specific calibration code must be determined through blood or equivalent testing before the strips can be released for consumer sale. The diabetics using the reagent based monitors must often enter this calibration code into the monitor to ensure that the monitor accurately reads the concentration of glucose in a sample placed on the strip. Naturally, this requirement leads to errors in reading and entering the calibration code, which can cause the monitor to make dangerously inaccurate readings of glucose concentration.

Reagent based monitor test strips also require special packaging during shipment and storage to prevent hydration of the reagent. Premature hydration affects the manner in which the reagent reacts with glucose and can cause erroneous readings. Once the test strips have been shipped, they must be stored by the vendor and user within a controlled storage temperature range. Unfortunately, the multitude of users are often unable to follow these protocols. When test strips and their reagents are not properly handled and stored, erroneous monitor readings can occur. Even when all necessary process, packaging and storage controls are followed, the reagents on the strips still degrade with time, and thus the strips have a limited shelf life. All these factors have led consumers to view reagent based monitors and test strips as expensive and troublesome. Indeed, reagent based test strips would be even more expensive if they were designed to be made simpler and completely fail safe.

The performance of reagent based glucose monitors is limited in a number of respects related to reagents. As discussed above, the accuracy of such monitors is limited by the sensitive nature of the reagent, and thus any breakdown in the strict protocols relating to manufacture, packaging, storage and use reduces the accuracy of the monitor. The time during which the reaction occurs between the glucose and the reagent is limited by the amount of reagent on the strip. Accordingly, the time for measuring the glucose concentration in the sample is limited as well. Confidence in the reagent based blood glucose monitor output can be increased only by taking more fluid samples and making additional measurements. This is undesirable because it doubles or triples the number of painful fluid removals. At the same time, reagent based monitor performance is limited in that the reaction rate limits the speed with which an individual measurement can be obtained. The reaction time is regarded as too long by most users.

Generally, reagent based monitors are too complex for must users, and have limited performance. Additionally, such monitors require users to draw fluid multiple times per day using sharp lances which must be disposed of carefully.

SUMMARY OF THE INVENTION

In one embodiment, a spectroscopic sample holder comprises a microporous sheet. The microporous sheet has a top surface, a bottom surface substantially parallel to the top surface, and at least one side surface oriented substantially perpendicular to the top and bottom surfaces. The side surface forms an exposed transit opening configured to contact a material sample and distribute the contacted material sample into the microporous sheet. The spectroscopic sample holder further comprises a first planar support member positioned on, and substantially parallel to, the top surface of the microporous sheet. The spectroscopic sample holder further comprises a second planar support member positioned on the bottom surface of the microporous sheet, and oriented substantially parallel to the first planar support member.

In another embodiment, an apparatus comprises a microporous sheet positioned between first and second support members. At least a portion of the microporous sheet is an exposed transit opening configured to receive and distribute a material sample into the microporous sheet.

In another embodiment, a method comprises providing a microporous sheet disposed between first and second support members. At least a portion of the microporous sheet is left exposed. The method further comprises contacting the exposed portion of the microporous sheet with a material sample. At least a portion of the material sample is drawn into the microporous sheet. The method further comprises transmitting electromagnetic radiation through the material sample in the microporous sheet. The method further comprises analyzing the electromagnetic radiation transmitted through the material sample in a spectral region of interest.

In another embodiment, a method comprises providing a microporous sheet disposed between first and second support members. At least a portion of the microporous sheet is left exposed. The method further comprises contacting the exposed portion of the microporous sheet with a material sample. At least a portion of the material sample is drawn into the microporous sheet. The method further comprises transmitting electromagnetic radiation emitted from the material sample in the microporous sheet to a detector. The method further comprises analyzing the electromagnetic radiation emitted from the material sample in a spectral region of interest.

In another embodiment, a reagentless analyte detection system comprises a source configured to emit electromagnetic radiation. The reagentless analyte detection system further comprises a detector positioned in an optical path of the radiation. The reagentless detection system further comprises a microporous sheet situated in the optical path of the radiation. The microporous sheet is also positioned between first and second support members. At least a portion of the microporous sheet is an exposed transit opening configured to receive and distribute a material sample into the microporous sheet. The analyte detection system performs optical analysis on the material sample to assess at least one constituent of the material sample.

Figure 1:
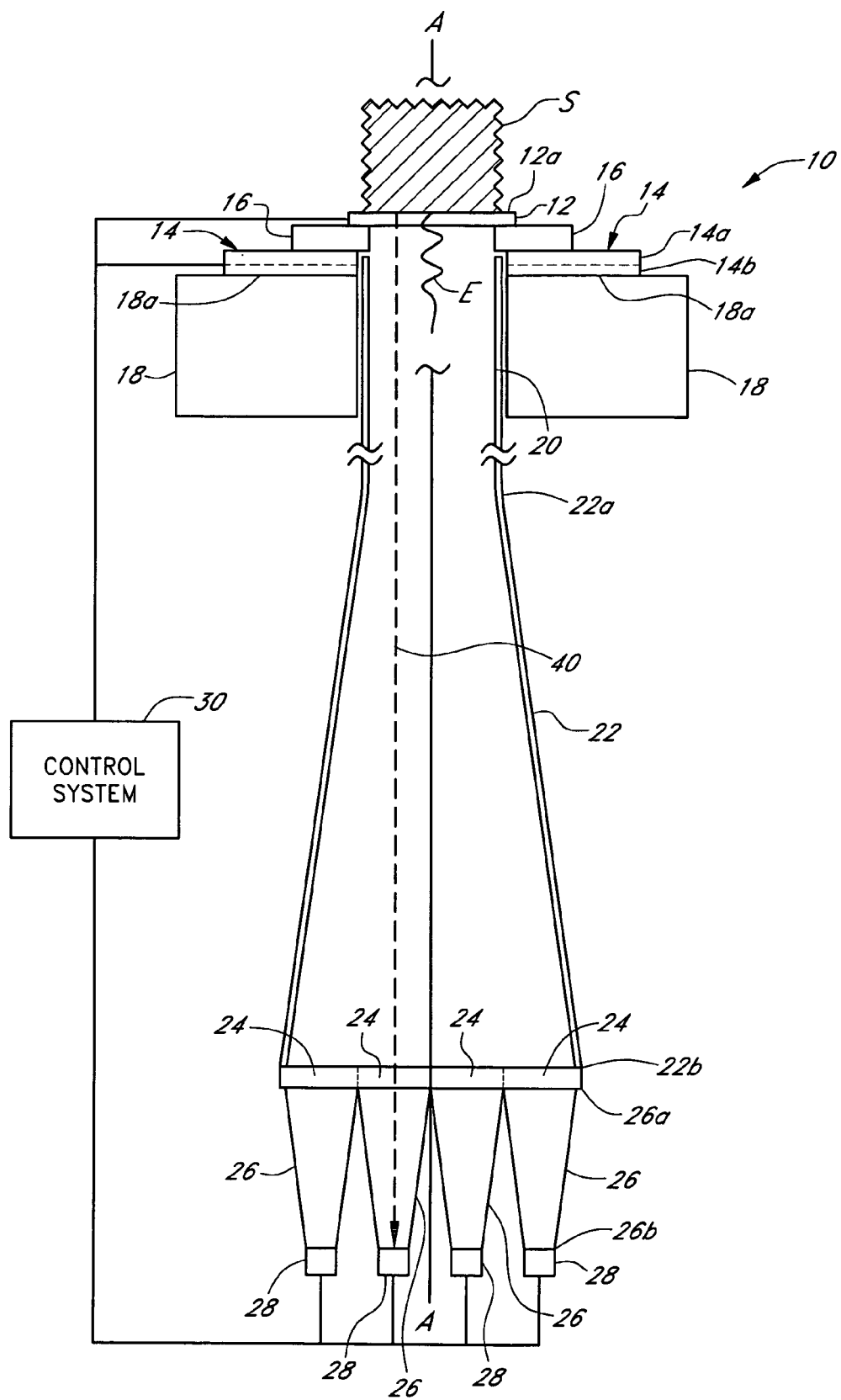
FIG. 1 is a schematic view of a noninvasive optical detection system.

These figures, which are idealized, are not to scale and are intended to be merely illustrative and non-limiting.

DETAILED DESCRIPTION OF PREFERRED EMBODIMENTS

Although certain preferred embodiments and examples are disclosed below, it will be understood by those skilled in the art that the invention extends beyond the specifically disclosed embodiments to other alternative embodiments and/or uses of the invention and obvious modifications and equivalents thereof. Thus, it is intended that the scope of the invention herein disclosed should not be limited by the particular disclosed embodiments described below.

OVERVIEW OF ANALYTE DETECTION SYSTEMS

Disclosed herein are analyte detection systems, including a noninvasive system discussed largely in part A below and a whole-blood system discussed largely in part B below. Also disclosed are various methods, including methods for detecting the concentration of an analyte in a material sample. Both the noninvasive system/method and the whole-blood system/method can employ optical measurement. As used herein with reference to measurement apparatus and methods, "optical" is a broad term and is used in its ordinary sense and refers, without limitation, to identification of the presence or concentration of an analyte in a material sample without requiring a chemical reaction to take place. As discussed in more detail below, the two approaches each can operate independently to perform an optical analysis of a material sample. The two approaches can also be combined in an apparatus, or the two approaches can be used together to perform different steps of a method.

In one embodiment, the two approaches are combined to perform calibration of an apparatus, for example, of an apparatus that employs a noninvasive approach. In another embodiment, an advantageous combination of the two approaches performs an invasive measurement to achieve greater accuracy and a whole-blood measurement to minimize discomfort to the patient. For example, the whole-blood technique may be more accurate than the noninvasive technique at certain times of the day, for example, at certain times after a meal has been consumed, or after a drug has been administered.

It should be understood, however, that any of the disclosed devices may be operated in accordance with any suitable detection methodology, and that any disclosed method may be employed in the operation of any suitable device. Furthermore, the disclosed devices and methods are applicable in a wide variety of situations or modes of operation, including but not limited to invasive, noninvasive, intermittent or continuous measurement, subcutaneous implantation, wearable detection systems, or any combination thereof.

Any method which is described and illustrated herein is not limited to the exact sequence of acts described, nor is it necessarily limited to the practice of all of the acts set forth. Other sequences of events or acts, or less than all of the events, or simultaneous occurrence of the events, may be used in practicing the method or methods in question.

A. Noninvasive System

1. Monitor Structure

FIG. 1 depicts a noninvasive optical detection system (hereinafter "noninvasive system") 10 in a presently preferred configuration. The depicted noninvasive system 10 is particularly suited for noninvasively detecting the concentration of an analyte in a material sample S, by observing the infrared energy emitted by the sample, as will be discussed in further detail below.

As used herein, the term "noninvasive" is a broad term and is used in its ordinary sense and refers, without limitation, to analyte detection devices and methods which have the capability to determine the concentration of an analyte in in-vivo tissue samples or bodily fluids. It should be understood, however, that the noninvasive system 10 disclosed herein is not limited to noninvasive use, as the noninvasive system 10 may be employed to analyze an in-vitro fluid or tissue sample which has been obtained invasively or noninvasively. As used herein, the term "invasive" (or, alternatively, "traditional") is a broad term and is used in its ordinary sense and refers, without limitation, to analyte detection methods which involve the removal of fluid samples through the skin. As used herein, the term "material sample" is a broad term and is used in its ordinary sense and refers, without limitation, to any collection of material which is suitable for analysis by the noninvasive system 10. For example, the material sample S may comprise a tissue sample, such as a human forearm, placed against the noninvasive system 10. The material sample S may also comprise a volume of a bodily fluid, such as whole blood, blood component(s), interstitial fluid or intercellular fluid obtained invasively, or saliva or urine obtained noninvasively, or any collection of organic or inorganic material. As used herein, the term "analyte" is a broad term and is used in its ordinary sense and refers, without limitation, to any chemical species the presence or concentration of which is sought in the material sample S by the noninvasive system 10. For example, the analyte(s) which may be detected by the noninvasive system 10 include but are not limited to glucose, ethanol, insulin, water, carbon dioxide, blood oxygen, cholesterol, bilirubin, ketones, fatty acids, lipoproteins, albumin, urea, creatinine, white blood cells, red blood cells, hemoglobin, oxygenated hemoglobin, carboxyhemoglobin, organic molecules, inorganic molecules, pharmaceuticals, cytochrome, various proteins and chromophores, microcalcifications, electrolytes, sodium, potassium, chloride, bicarbonate, and hormones. As used herein to describe measurement techniques, the term "continuous" is a broad term and is used in its ordinary sense and refers, without limitation, to the taking of discrete measurements more frequently than about once every 10 minutes, and/or the taking of a stream or series of measurements or other data over any suitable time interval, for example, over an interval of one to several seconds, minutes, hours, days, or longer. As used herein to describe measurement techniques, the term "intermittent" is a broad term and is used in its ordinary sense and refers, without limitation, to the taking of measurements less frequently than about once every 10 minutes.

The noninvasive system 10 preferably comprises a window assembly 12, although in some embodiments the window assembly 12 may be omitted. One function of the window assembly 12 is to permit infrared energy E to enter the noninvasive system 10 from the sample S when it is placed against an upper surface 12a of the window assembly 12. The window assembly 12 includes a heater layer (see discussion below) which is employed to heat the material sample S and stimulate emission of infrared energy therefrom. A cooling system 14, preferably comprising a Peltier-type thermoelectric device, is in thermally conductive relation to the window assembly 12 so that the temperature of the window assembly 12 and the material sample S can be manipulated in accordance with a detection methodology discussed in greater detail below. The cooling system 14 includes a cold surface 14a which is in thermally conductive relation to a cold reservoir 16 and the window assembly 12, and a hot surface 14b which is in thermally conductive relation to a heat sink 18.

As the infrared energy E enters the noninvasive system 10, it first passes through the window assembly 12, then through an optical mixer 20, and then through a collimator 22. The optical mixer 20 preferably comprises a light pipe having highly reflective inner surfaces which randomize the directionality of the infrared energy E as it passes therethrough and reflects against the mixer walls. The collimator 22 also comprises a light pipe having highly-reflective inner walls, but the walls diverge as they extend away from the mixer 20. The divergent walls cause the infrared energy E to tend to straighten as it advances toward the wider end of the collimator 22, due to the angle of incidence of the infrared energy E when reflecting against the collimator walls.

From the collimator 22 the infrared energy E passes through an array of filters 24, each of which allows only a selected wavelength or band of wavelengths to pass therethrough. These wavelengths/bands are selected to highlight or isolate the absorptive effects of the analyte of interest in the detection methodology discussed in greater detail below. Each filter 24 is preferably in optical communication with a concentrator 26 and an infrared detector 28. The concentrators 26 have highly reflective, converging inner walls which concentrate the infrared energy E as it advances toward the detectors 28, increasing the density of the energy incident upon the detectors 28.

The detectors 28 are in electrical communication with a control system 30 which receives electrical signals from the detectors 28 and computes the concentration of the analyte in the sample S. The control system 30 is also in electrical communication with the window 12 and cooling system 14, so as to monitor the temperature of the window 12 and/or cooling system 14 and control the delivery of electrical power to the window 12 and cooling system 14.

a. Window Assembly

Figure 2:
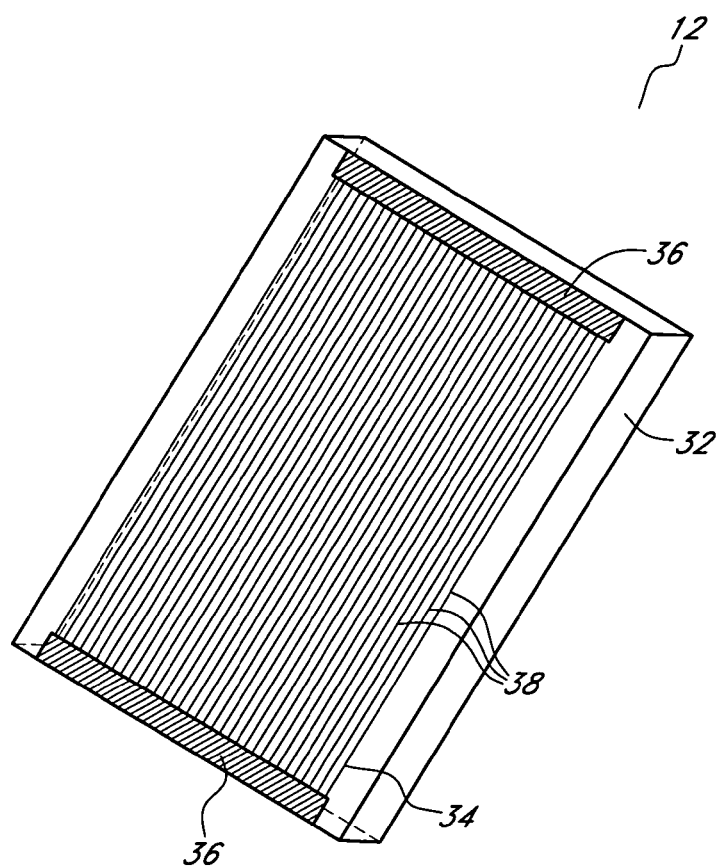
FIG. 2 is a perspective view of a window assembly for use with the noninvasive detection system.

A preferred configuration of the window assembly 12 is shown in perspective, as viewed from its underside (in other words, the side of the window assembly 12 opposite the sample S), in FIG. 2. The window assembly 12 generally comprises a main layer 32 formed of a highly infrared-transmissive material and a heater layer 34 affixed to the underside of the main layer 32. The main layer 32 is preferably formed from diamond, most preferably from chemical-vapor-deposited ("CVD") diamond, with a preferred thickness of about 0.25 millimeters. In other embodiments alternative materials which are highly infrared-transmissive, such as silicon or germanium, may be used in forming the main layer 32.

The heater layer 34 preferably comprises bus bars 36 located at opposing ends of an array of heater elements 38. The bus bars 36 are in electrical communication with the elements 38 so that, upon connection of the bus bars 36 to a suitable electrical power source (not shown) a current may be passed through the elements 38 to generate heat in the window assembly 12. The heater layer 34 may also include one or more temperature sensors (not shown), such as thermistors or resistance temperature devices ("RTDs"), to measure the temperature of the window assembly 12 and provide temperature feedback to the control system 30 (see FIG. 1).

Still referring to FIG. 2, the heater layer 34 preferably comprises a first adhesion layer of gold or platinum (hereinafter referred to as the "gold" layer) deposited over an alloy layer which is applied to the main layer 32. The alloy layer comprises a material suitable for implementation of the heater layer 34, such as, by way of example, 10/90 titanium/tungsten, titanium/platinum, nickel/chromium, or other similar material. The gold layer preferably has a thickness of about 4000 Å, and the alloy layer preferably has a thickness ranging between about 300 Å and about 500 Å. The gold layer and/or the alloy layer may be deposited onto the main layer 32 by chemical deposition including, but not necessarily limited to, vapor deposition, liquid deposition, plating, laminating, casting, sintering, or other forming or deposition methodologies well known to those of ordinary skill in the art. If desired, the heater layer 34 may be covered with an electrically insulating coating which also enhances adhesion to the main layer 32. One preferred coating material is aluminum oxide. Other acceptable materials include, but are not limited to, titanium dioxide or zinc selenide.

The heater layer 34 may incorporate a variable pitch distance between centerlines of adjacent heater elements 38 to maintain a constant power density, and promote a uniform temperature, across the entire heater layer 34. Where a constant pitch distance is employed, the preferred distance is at least about 50–100 microns. Although the heater elements 38 generally have a preferred width of about 25 microns, their width may also be varied as needed for the same reasons stated above.

Alternative structures suitable for use as the heater layer 34 include, but are not limited to, thermoelectric heaters, radiofrequency ("RF") heaters, infrared radiation heaters, optical heaters, heat exchangers, electrical resistance heating grids, wire bridge heating grids, or laser heaters. Whichever type of heater layer is employed, it is preferred that the heater layer obscures about 10% or less of the window assembly 12.

In a preferred embodiment, the window assembly 12 comprises substantially only the main layer 32 and the heater layer 34. Thus, when installed in an optical detection system such as the noninvasive system 10 shown in FIG. 1, the window assembly 12 will facilitate a minimally obstructed optical path between a (preferably flat) upper surface 12a of the window assembly 12 and the infrared detectors 28 of the noninvasive system 10. The optical path 40 in the preferred noninvasive system 10 proceeds only through the main layer 32 and heater layer 34 of the window assembly 12 (including any antireflective, index-matching, electrical insulating or protective coatings applied thereto or placed therein), through the optical mixer 20 and collimator 22 and to the detectors 28.

Figure 2A:
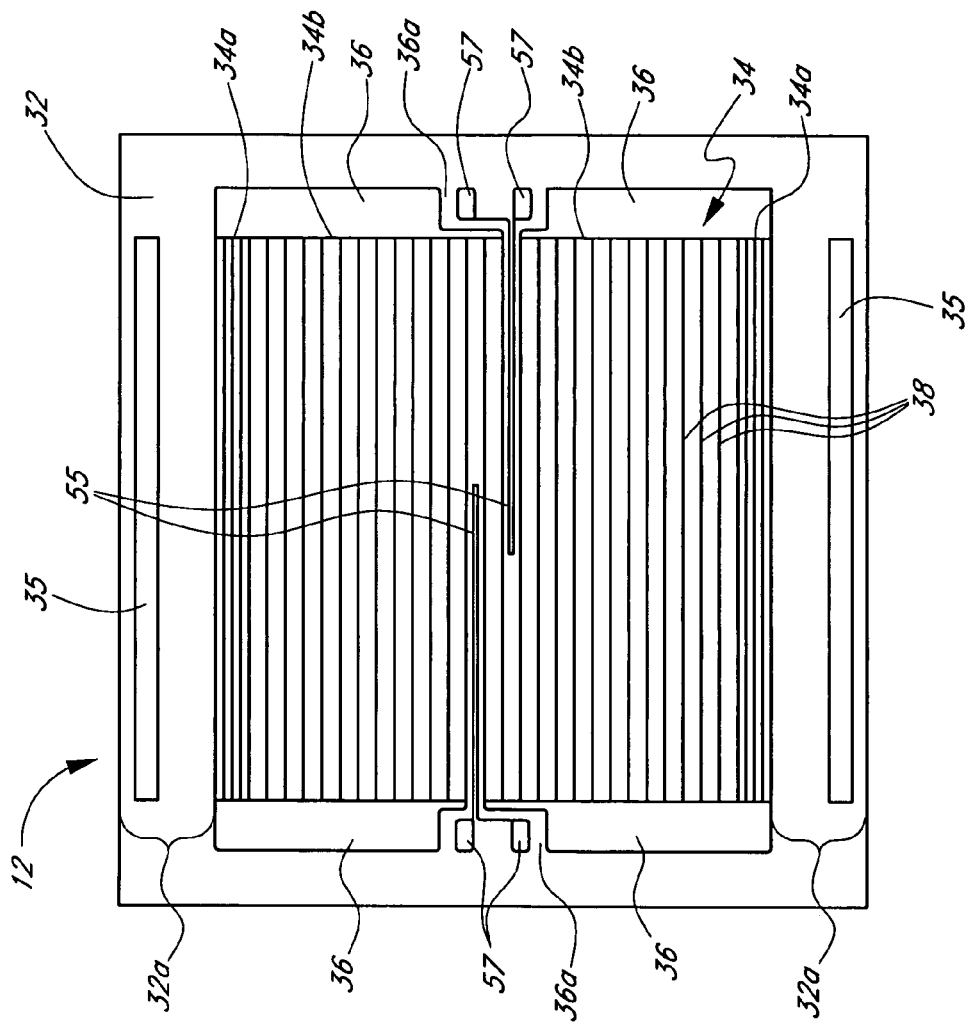
FIG. 2A is a plan view of another embodiment of a window assembly for use with the noninvasive detection system.

FIG. 2A shows another embodiment of the window assembly 12, that may be used in place of the window assembly 12 depicted in FIG. 2. The window assembly 12 shown in FIG. 2A may be similar to that shown in FIG. 2, except as described below. In the embodiment of FIG. 2A the main layer 32 has a preferred thickness of up to about 0.012" and more preferably about 0.010" or less. The heater layer 34 may also include one or more resistance temperature devices ("RTDs") 55 to measure the temperature of the window assembly 12 and provide temperature feedback to a control system 30. The RTDs 55 terminate in RTD connection pads 57.

In the embodiment of FIG. 2A, the heater elements 38 are typically provided with a width of about 25 microns. The pitch distance separating centerlines of adjacent heater elements 38 may be reduced, and/or the width of the heater elements 38 may be increased, in the regions of the window assembly 12 near the point(s) of contact with the thermal diffuser 410 (see FIGS. 6B through 6D and discussion below). This arrangement advantageously promotes an isothermal temperature profile at the upper surface of the main layer 32 despite thermal contact with the thermal diffuser.

The embodiment shown in FIG. 2A includes a plurality of heater elements 38 of substantially equal width which are variably spaced across the width of the main layer 32. In the embodiment of FIG. 2A, the centerlines of the heater elements 38 are spaced at a first pitch distance of about 0.0070" at peripheral portions 34a of the heater layer 34, and at a second pitch distance of about 0.015" at a central portion 34b of the main layer 32. The heater elements 38 closest to the center are preferably sufficiently spaced to allow the RTDs 55 to extend therebetween. In the embodiment of FIG. 2A, the main layer 32 includes peripheral regions 32a which extend about 0.053" from the outermost heater element on each side of the heater layer 34 to the adjacent edge of the main layer 32. As shown, the bus bars 36 are preferably configured and segmented to allow space for the RTDs 55 and the RTD connection pads 57, in intermediate gaps 36a. The RTDs 55 preferably extend into the array of heater elements 38 by a distance that is slightly longer than half of the length of an individual heater element 38. In alternative embodiments, the RTDs 55 may be located at the edges of the main layer 32, or at other locations as desired for a particular noninvasive system.

With continued reference to FIG. 2A, the peripheral regions 32a of the main layer 32 may include metallized edge portions 35 for facilitating connection to the diffuser 410 (discussed below in connection with FIGS. 6B through 6D). The metallized edge portions 35 may be formed by the same or similar processes used in forming the heater elements 38 and RTDs 55. In the embodiment of FIG. 2A, the edge portions 35 are typically between about 0.040" and about 0.060" wide by between about 0.450" and about 0.650" long, and in one embodiment, they are about 0.050" by about 0.550". Other dimensions may be appropriately used so long as the window assembly 12 may be joined in thermal communication with the diffuser 410 as needed.

In the embodiment shown in FIG. 2A, the main layer 32 is about 0.690" long by about 0.571" wide, and the heater layer 34 (excluding the metallized edge portions 35) is about 0.640" long by about 0.465" wide. The main layer 32 is about 0.010"–0.012" thick, and is advantageously thinner than about 0.010" where possible. Each heater element 38 is about 0.570" long, and each peripheral portion 34a is about 0.280" wide. These dimensions are merely exemplary; of course, other dimensions may be used as desired.

Figure 3:
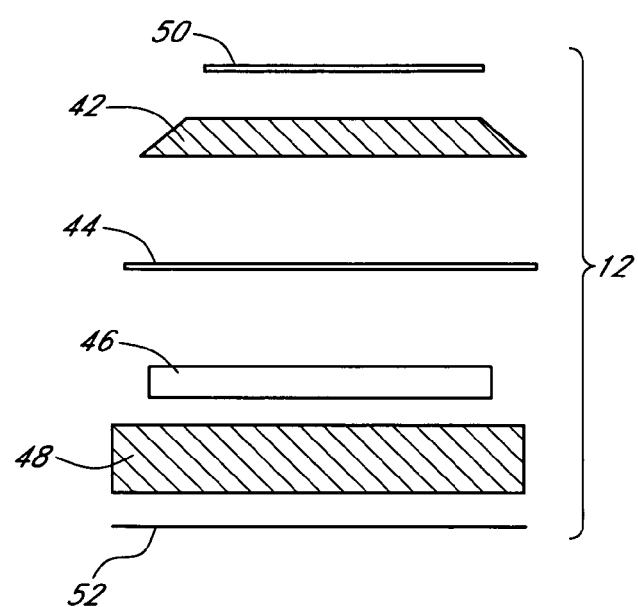
FIG. 3 is an exploded schematic view of another embodiment of a window assembly for use with the noninvasive detection system.

FIG. 3 depicts an exploded side view of an alternative configuration for the window assembly 12, which may be used in place of the configuration shown in FIG. 2. The window assembly 12 depicted in FIG. 3 includes near its upper surface (the surface intended for contact with the sample S) a highly infrared-transmissive, thermally conductive spreader layer 42. Underlying the spreader layer 42 is a heater layer 44. A thin electrically insulating layer (not shown), such as layer of aluminum oxide, titanium dioxide or zinc selenide, may be disposed between the heater layer 44 and the spreader layer 42. (An aluminum oxide layer also increases adhesion of the heater layer 44 to the spreader layer 42.) Adjacent to the heater layer 44 is an impedance matching and thermal insulating layer 46. Adjacent to the thermal insulating layer 46 is a thermally conductive inner layer 48. The spreader layer 42 is coated on its top surface with a thin layer of protective coating 50. The bottom surface of the inner layer 48 is coated with a thin overcoat layer 52. Preferably, the protective coating 50 and the overcoat layer 52 have antireflective properties.

The spreader layer 42 is preferably formed of a highly infrared-transmissive material having a high thermal conductivity sufficient to facilitate heat transfer from the heater layer 44 uniformly into the material sample S when it is placed against the window assembly 12. Other effective materials include, but are not limited to, CVD diamond, diamond-like carbon, gallium arsenide, germanium, and other infrared-transmissive materials having sufficiently high thermal conductivity. Preferred dimensions for the spreader layer 42 are about one inch in diameter and about 0.010 inch thick. As shown in FIG. 3, a preferred embodiment of the spreader layer 42 incorporates a beveled edge. Although not required, an approximate 45-degree bevel is preferred.

The protective coating 50 is intended to protect the top surface of the spreader layer 42 from damage. Ideally, the protective coating 50 is highly infrared-transmissive and highly resistant to mechanical damage, such as scratching or abrasion. It is also preferred that the protective coating 50 and the overcoat layer 52 have high thermal conductivity and antireflective and/or index-matching properties. A satisfactory material for use as the protective coating 50 and the overcoat layer 52 is the multi-layer Broad Band Anti-Reflective Coating produced by Deposition Research Laboratories, Inc. of Saint Charles, Mo. Diamond-like carbon coatings are also suitable.

Except as noted below, the heater layer 44 is generally similar to the heater layer 34 employed in the window assembly shown in FIG. 2. Alternatively, the heater layer 44 may comprise a doped infrared-transmissive material, such as a doped silicon layer, with regions of higher and lower resistivity. The heater layer 44 preferably has a resistance of about 2 ohms and has a preferred thickness of about 1500 angstroms. A preferred material for forming the heater layer 44 is a gold alloy, but other acceptable materials include, but are not limited to, platinum, titanium, tungsten, copper, and nickel.

The thermal insulating layer 46 prevents the dissipation of heat from the heater layer 44 while allowing the cooling system 14 to effectively cool the material sample S (see FIG. 1). The thermal insulating layer 46 comprises a material having thermally insulative (for example, lower thermal conductivity than the spreader layer 42) and infrared transmissive qualities. A preferred material is a germanium-arsenic-selenium compound of the calcogenide glass family known as AMTIR-1 produced by Amorphous Materials, Inc. of Garland, Tex. The illustrated embodiment has a diameter of about 0.85 inches and a preferred thickness in the range of about 0.005 to about 0.010 inches. As heat generated by the heater layer 44 passes through the spreader layer 42 into the material sample S, the thermal insulating layer 46 insulates this heat.

The inner layer 48 is formed of thermally conductive material, preferably crystalline silicon formed using a conventional floatzone crystal growth method. The purpose of the inner layer 48 is to serve as a cold-conducting mechanical base for the entire layered window assembly.

The overall optical transmission of the window assembly 12 shown in FIG. 3 is preferably at least 70%. The window assembly 12 of FIG. 3 is preferably held together and secured to the noninvasive system 10 by a holding bracket (not shown). The bracket is preferably formed of a glass-filled plastic, for example Ultem 2300, manufactured by General Electric. Ultem 2300 has low thermal conductivity which prevents heat transfer from the layered window assembly 12.

b. Cooling System

The cooling system 14 (see FIG. 1) preferably comprises a Peltier-type thermoelectric device. Thus, the application of an electrical current to the preferred cooling system 14 causes the cold surface 14a to cool and causes the opposing hot surface 14b to heat up. The cooling system 14 cools the window assembly 12 via the situation of the window assembly 12 in thermally conductive relation to the cold surface 14a of the cooling system 14. It is contemplated that the cooling system 14, the heater layer 34, or both, can be operated to induce a desired time-varying temperature in the window assembly 12 to create an oscillating thermal gradient in the sample S, in accordance with various analyte-detection methodologies discussed herein.

Preferably, the cold reservoir 16 is positioned between the cooling system 14 and the window assembly 12, and functions as a thermal conductor between the cooling system 14 and the window assembly 12. The cold reservoir 16 is formed from a suitable thermally conductive material, preferably brass. Alternatively, the window assembly 12 can be situated in direct contact with the cold surface 14a of the cooling system 14.

In alternative embodiments, the cooling system 14 may comprise a heat exchanger through which a coolant, such as air, nitrogen or chilled water, is pumped, or a passive conduction cooler such as a heat sink. As a further alternative, a gas coolant such as nitrogen may be circulated through the interior of the noninvasive system 10 so as to contact the underside of the window assembly 12 (see FIG. 1) and conduct heat therefrom.

Figure 4:
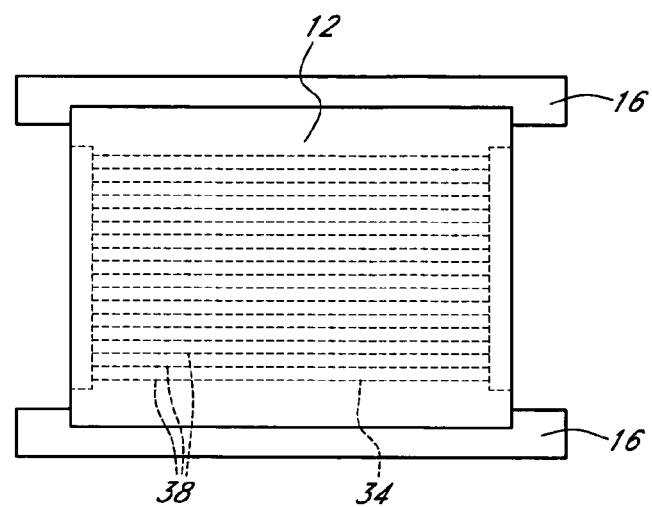
FIG. 4 is a plan view of the window assembly connected to a cooling system.
Figure 5:
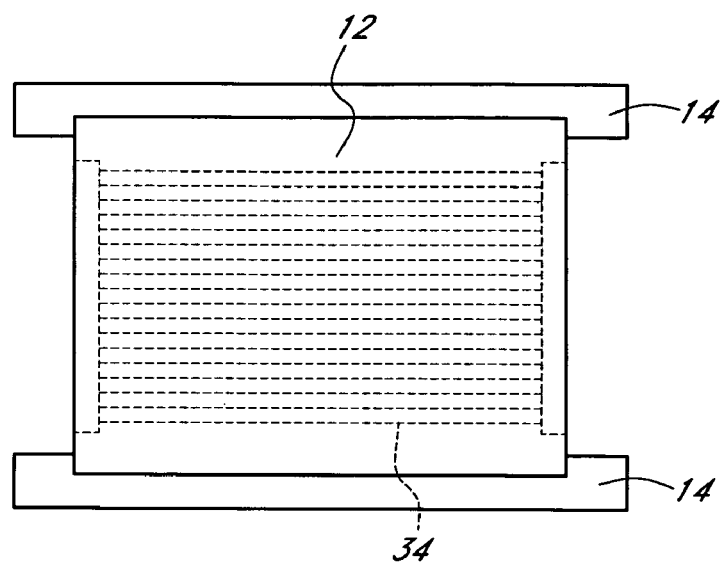
FIG. 5 is a plan view of the window assembly connected to a cold reservoir.

FIG. 4 is a top schematic view of a preferred arrangement of the window assembly 12 (of the types shown in FIG. 2 or 2A) and the cold reservoir 16. FIG. 5 is a top schematic view of an alternative arrangement in which the window assembly 12 directly contacts the cooling system 14. The cold reservoir 16/cooling system 14 preferably contacts the underside of the window assembly 12 along opposing edges thereof, on either side of the heater layer 34. With thermal conductivity thus established between the window assembly 12 and the cooling system 14, the window assembly can be cooled as needed during operation of the noninvasive system 10. To promote a substantially uniform or isothermal temperature profile over the upper surface 12a of the window assembly 12, the pitch distance between centerlines of adjacent heater elements 38 may be made smaller (thereby increasing the density of heater elements 38) near the region(s) of contact between the window assembly 12 and the cold reservoir 16/cooling system 14. As a supplement or alternative, the heater elements 38 themselves may be made wider near these regions of contact. As used herein, "isothermal" is a broad term and is used in its ordinary sense and refers, without limitation, to a condition in which, at a given point in time, the temperature of the window assembly 12 or other structure is substantially uniform across a surface intended for placement in thermally conductive relation to the material sample S. Thus, although the temperature of the structure or surface may fluctuate over time, at any given point in time the structure or surface may nonetheless be isothermal.

Figure 6:
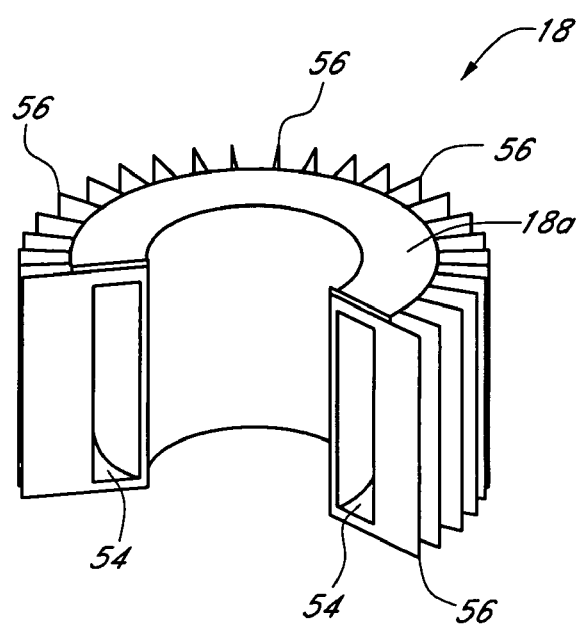
FIG. 6 is a cutaway view of a heat sink for use with the noninvasive detection system.

The heat sink 18 drains waste heat from the hot surface 14b of the cooling system 14 and stabilizes the operational temperature of the noninvasive system 10. The preferred heat sink 18 (see FIG. 6) comprises a hollow structure formed from brass or any other suitable material having a relatively high specific heat and high heat conductivity. The heat sink 18 has a conduction surface 18a which, when the heat sink 18 is installed in the noninvasive system 10, is in thermally conductive relation to the hot surface 14b of the cooling system 14 (see FIG. 1). A cavity 54 is formed in the heat sink 18 and preferably contains a phase-change material (not shown) to increase the capacity of the heat sink 18. A preferred phase change material is a hydrated salt, such as calcium chloride hexahydrate, available under the name TH29 from PCM Thermal Solutions, Inc., of Naperville, Ill. Alternatively, the cavity 54 may be omitted to create a heat sink 18 comprising a solid, unitary mass. The heat sink 18 also forms a number of fins 56 to further increase the conduction of heat from the heat sink 18 to surrounding air.

Alternatively, the heat sink 18 may be formed integrally with the optical mixer 20 and/or the collimator 22 as a unitary mass of rigid, heat-conductive material such as brass or aluminum. In such a heat sink, the mixer 20 and/or collimator 22 extend axially through the heat sink 18, and the heat sink defines the inner walls of the mixer 20 and/or collimator 22. These inner walls are coated and/or polished to have appropriate reflectivity and non-absorbance in infrared wavelengths as will be further described below. Where such a unitary heat sink-mixer-collimator is employed, it is desirable to thermally insulate the detector array from the heat sink.

It should be understood that any suitable structure may be employed to heat and/or cool the material sample S, instead of or in addition to the window assembly 12/cooling system 14 disclosed above, so long a proper degree of cycled heating and/or cooling are imparted to the material sample S. In addition other forms of energy, such as but not limited to light, radiation, chemically induced heat, friction and vibration, may be employed to heat the material sample S. It will be further appreciated that heating of the sample can achieved by any suitable method, such as convection, conduction, radiation, and so forth.

c. Window Mounting System

Figure 6A:
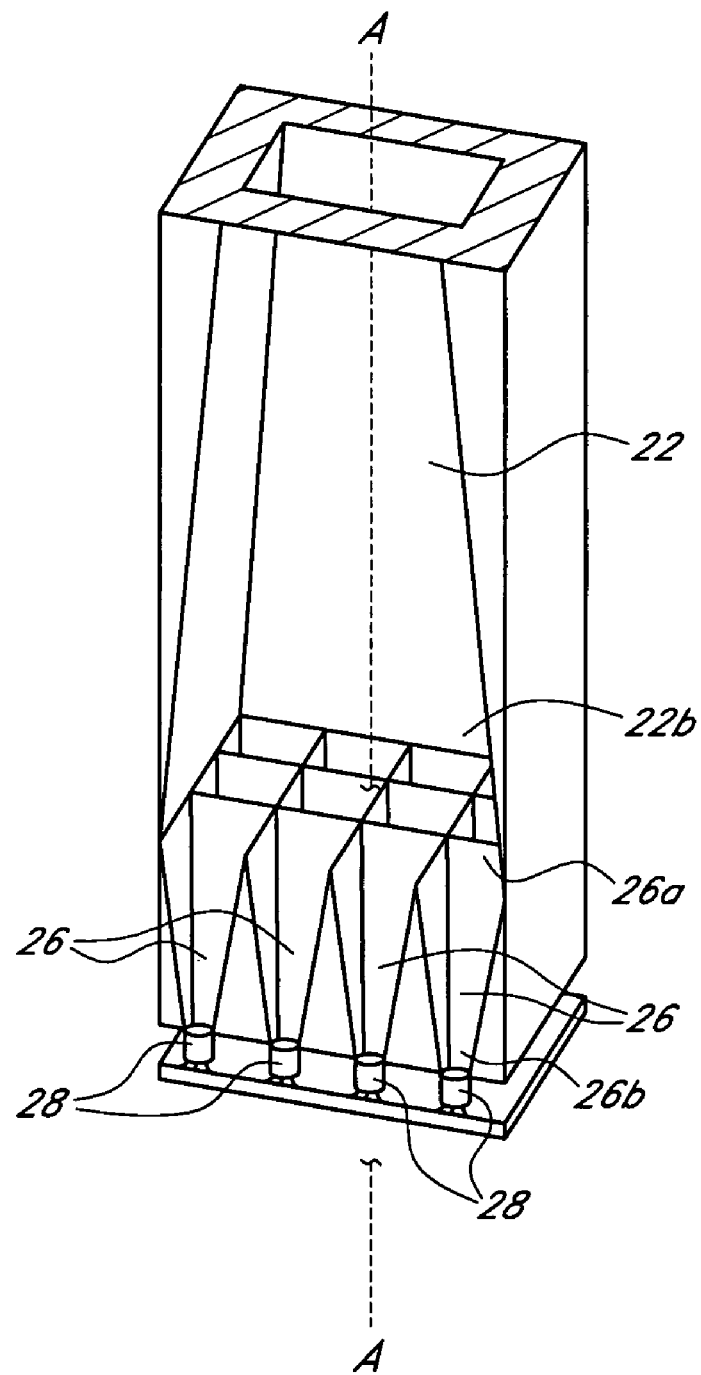
FIG. 6A is a cutaway perspective view of a lower portion of the noninvasive detection system of FIG. 1.
Figure 6B:
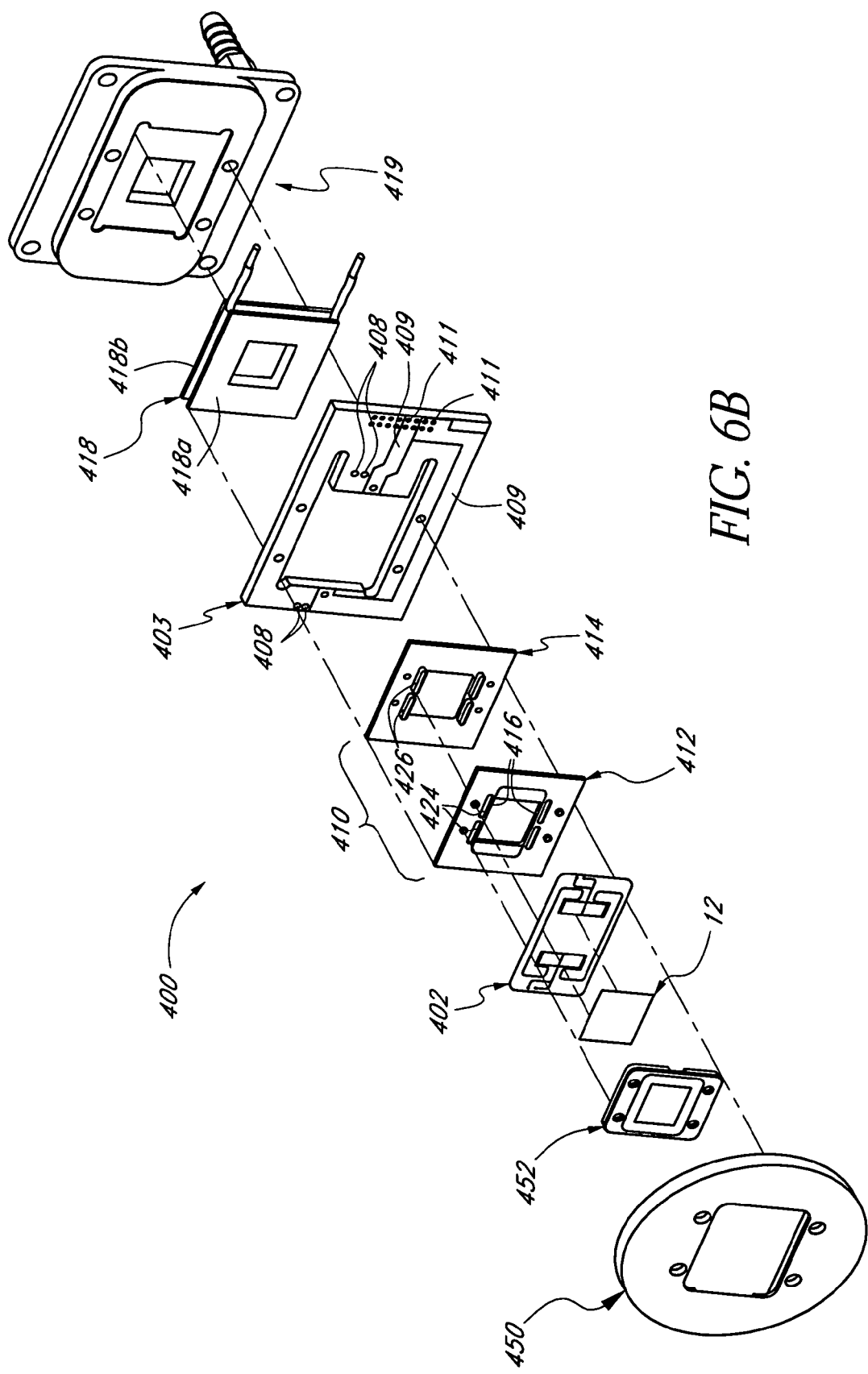
FIG. 6B is an exploded perspective view of a window mounting system for use with the noninvasive optical detection system.

FIG. 6B illustrates an exploded view of a window mounting system 400 which, in one embodiment, is employed as part of the noninvasive system 10 disclosed above. Where employed in connection with the noninvasive system 10, the window mounting system 400 supplements or, where appropriate, replaces any of the window assembly 12, cooling system 14, cold reservoir 16 and heat sink 18 shown in FIG. 1. In one embodiment, the window mounting system 400 is employed in conjunction with the window assembly 12 depicted in FIG. 2A; in alternative embodiments, the window assemblies shown in FIGS. 2 and 3 and described above may also be used in conjunction with the window mounting system 400 illustrated in FIG. 6B.

In the window mounting system 400, the window assembly 12 is physically and electrically connected (typically by soldering) to a first printed circuit board ("first PCB") 402. The window assembly 12 is also in thermally conductive relation (typically by contact) to a thermal diffuser 410. The window assembly may also be fixed to the diffuser 410 by soldering.

The thermal diffuser 410 generally comprises a heat spreader layer 412 which, as mentioned, preferably contacts the window assembly 12, and a conductive layer 414 which is typically soldered to the heat spreader layer 412. The conductive layer 414 may then be placed in direct contact with a cold side 418a of a thermoelectric cooler ("TEC") 418 or other cooling device. The TEC 418, which in one embodiment comprises a 25 watt TEC manufactured by MELCOR, is in electrical communication with a second PCB 403, which includes TEC power leads 409 and TEC power terminals 411 for connection of the TEC 418 to an appropriate power source (not shown). The second PCB 403 also includes contacts 408 for connection with RTD terminals 407 (see FIG. 6C) of the first PCB 402. A heat sink 419, which may take the form of the illustrated water jacket, the heat sink 18 shown in FIG. 6, any other heat sink structures mentioned herein, or any other appropriate device, is in thermal communication with a hot side 418b of the TEC 418 (or other cooling device), in order to remove any excess heat created by the TEC 418.

Figure 6C:
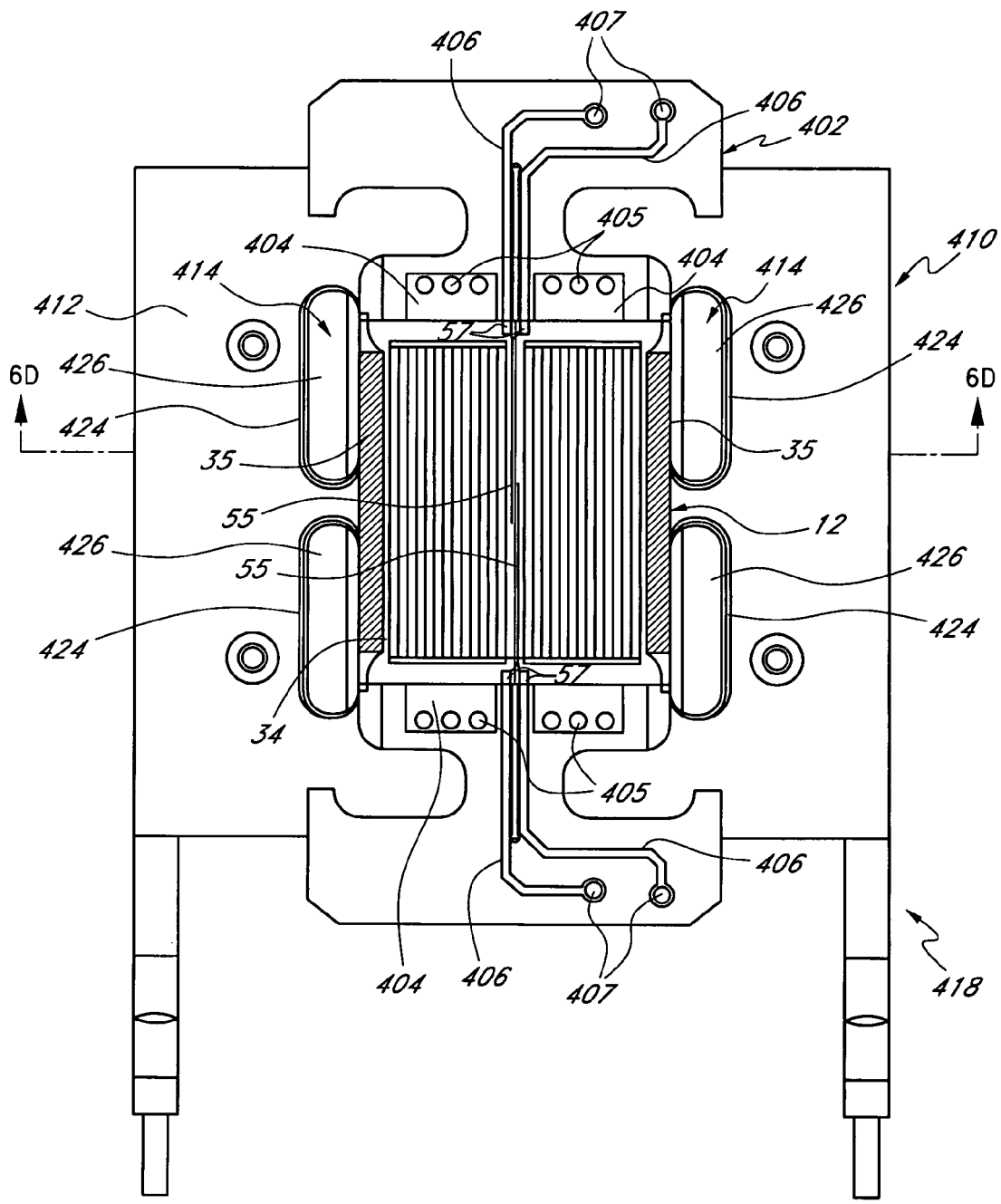
FIG. 6C is a partial plan view of the window mounting system of FIG. 6B.

FIG. 6C illustrates a plan view of the interconnection of the window assembly 12, the first PCB 402, the diffuser 410 and the thermoelectric cooler 418. The first PCB 402 includes RTD bonding leads 406 and heater bonding pads 404 which permit attachment of the RTDs 55 and bus bars 36, respectively, of the window assembly 12 to the first PCB 402 via soldering or other conventional techniques. Electrical communication is thus established between the heater elements 38 of the heater layer 34, and heater terminals 405 formed in the heater bonding pads 404. Similarly, electrical communication is established between the RTDs 55 and RTD terminals 407 formed at the ends of the RTD bonding leads 406. Electrical connections can be established with the heater elements 38 and the RTDs 55 via simple connection to the heater terminals 405 and the RTD terminals 407 of the first PCB 402.

With further reference to FIGS. 2A and 6B through 6C, the heat spreader layer 412 of the thermal diffuser 410 contacts the underside of the main layer 32 of the window assembly 12 via a pair of rails 416. The rails 416 may contact the main layer 32 at the metallized edge portions 35, or at any other appropriate location. The physical and thermal connection between the rails 416 and the window main layer 32 may be achieved by soldering, as indicated above. Alternatively, the connection may be achieved by an adhesive such as epoxy, or any other appropriate method. The material chosen for the window main layer 32 is preferably sufficiently thermally conductive that heat may be quickly removed from the main layer 32 through the rails 416, the diffuser 410, and the TEC 418.

Figure 6D:
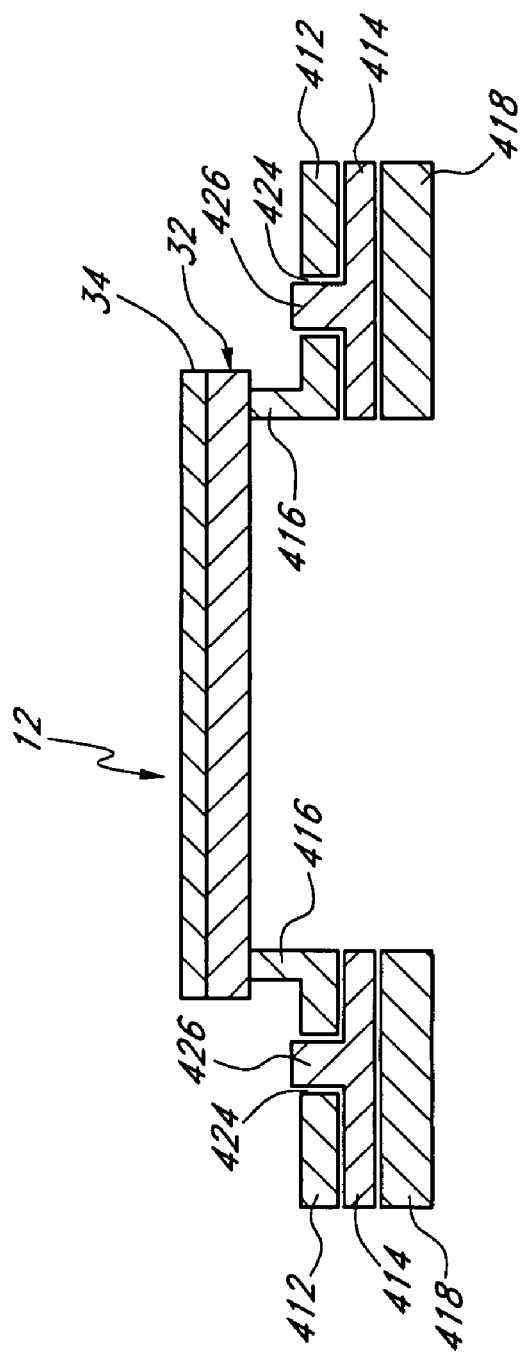
FIG. 6D is a sectional view of the window mounting system of FIG. 6C.

FIG. 6D shows a cross-sectional view of the assembly of FIG. 6C through line 6D—6D. As can be seen in FIG. 6D, the window assembly 12 contacts the rails 416 of the heat spreader layer 412. The conductive layer 414 underlies the heat spreader layer 412 and may comprise protrusions 426 configured to extend through openings 424 formed in the spreader layer 412. The openings 424 and protrusions 426 are sized to leave sufficient expansion space therebetween, to allow expansion and contraction of the conductive layer 414 without interference with, or causing deformation of, the window assembly 12 or the heat spreader layer 412. Moreover, the protrusions 426 and openings 424 coact to prevent displacement of the spreader layer 412 with respect to the conductive layer 414 as the conductive layer 414 expands and contracts.

The thermal diffuser 410 provides a thermal impedance between the TEC 418 and the window assembly 12, which impedance is selected to drain heat from the window assembly at a rate proportional to the power output of the heater layer 34. In this way, the temperature of the main layer 32 can be rapidly cycled between "hot" and a "cold" temperatures, thereby allowing a time-varying thermal gradient to be induced in a sample S placed against the window assembly 12.

The heat spreader layer 412 is preferably made of a material which has substantially the same coefficient of thermal expansion as the material used to form the window assembly main layer 32, within the expected operating temperature range. Preferably, both the material used to form the main layer 32 and the material used to form the heat spreader layer 412 have substantially the same, extremely low, coefficient of thermal expansion. For this reason, CVD diamond is preferred for the main layer 32 (as mentioned above); with a CVD diamond main layer 32 the preferred material for the heat spreader layer 412 is Invar. Invar advantageously has an extremely low coefficient of thermal expansion and a relatively high thermal conductivity. Because Invar is a metal, the main layer 32 and the heat spreader layer 412 can be thermally bonded to one another with little difficulty. Alternatively, other materials may be used for the heat spreader layer 412; for example, any of a number of glass and ceramic materials with low coefficients of thermal expansion may be employed.

The conductive layer 414 of the thermal diffuser 410 is typically a highly thermally conductive material such as copper (or, alternatively, other metals or non-metals exhibiting comparable thermal conductivities). The conductive layer 414 is typically soldered or otherwise bonded to the underside of the heat spreader layer 412.

In the illustrated embodiment, the heat spreader layer 412 may be constructed according to the following dimensions, which are to be understood as exemplary; accordingly the dimensions may be varied as desired. The heat spreader layer 412 has an overall length and width of about 1.170", with a central opening of about 0.590" long by 0.470" wide. Generally, the heat spreader layer 412 is about 0.030" thick; however, the rails 416 extend a further 0.045" above the basic thickness of the heat spreader layer 412. Each rail 416 has an overall length of about 0.710"; over the central 0.525" of this length each rail 416 is about 0.053" wide. On either side of the central width each rail 416 tapers, at a radius of about 0.6", down to a width of about 0.023". Each opening 424 is about 0.360" long by about 0.085" wide, with corners rounded at a radius of about 0.033".

In the illustrated embodiment, conductive layer 414 may be constructed according to the following dimensions, which are to be understood as exemplary; accordingly the dimensions may be varied as desired. The conductive layer 414 has an overall length and width of about 1.170", with a central opening of about 0.590" long by 0.470" wide. Generally, the conductive layer 414 is about 0.035" thick; however, the protrusions 426 extend a further 0.075"–0.085" above the basic thickness of the conductive layer 414. Each protrusion 426 is about 0.343" long by about 0.076" wide, with corners rounded at a radius of about 0.035".

As shown in FIG. 6B, first and second clamping plates 450 and 452 may be used to clamp the portions of the window mounting system 400 to one another. For example, the second clamping plate 452 is configured to clamp the window assembly 12 and the first PCB 402 to the diffuser 410 with screws or other fasteners extending through the openings shown in the second clamping plate 452, the heat spreader layer 412 and the conductive layer 414. Similarly, the first clamping plate 450 is configured to overlie the second clamping plate 452 and clamp the rest of the window mounting system 400 to the heat sink 419, thus sandwiching the second clamping plate 452, the window assembly 12, the first PCB 402, the diffuser 410, the second PCB 403, and the TEC 418 therebetween. The first clamping plate 450 prevents undesired contact between the sample S and any portion of the window mounting system 400, other than the window assembly 12 itself. Other mounting plates and mechanisms may also be used as desired.

d. Optics

As shown in FIG. 1, the optical mixer 20 comprises a light pipe with an inner surface coating which is highly reflective and minimally absorptive in infrared wavelengths, preferably a polished gold coating, although other suitable coatings may be used where other wavelengths of electromagnetic radiation are employed. The pipe itself may be fabricated from a another rigid material such as aluminum or stainless steel, as long as the inner surfaces are coated or otherwise treated to be highly reflective. Preferably, the optical mixer 20 has a rectangular cross-section (as taken orthogonal to the longitudinal axis A—A of the mixer 20 and the collimator 22), although other cross-sectional shapes, such as other polygonal shapes or circular or elliptical shapes, may be employed in alternative embodiments. The inner walls of the optical mixer 20 are substantially parallel to the longitudinal axis A—A of the mixer 20 and the collimator 22. The highly reflective and substantially parallel inner walls of the mixer 20 maximize the number of times the infrared energy E will be reflected between the walls of the mixer 20, thoroughly mixing the infrared energy E as it propagates through the mixer 20. In a presently preferred embodiment, the mixer 20 is about 1.2 inches to 2.4 inches in length and its cross-section is a rectangle of about 0.4 inches by about 0.6 inches. Of course, other dimensions may be employed in constructing the mixer 20. In particular it is advantageous to miniaturize the mixer or otherwise make it as small as possible Still referring to FIG. 1, the collimator 22 comprises a tube with an inner surface coating which is highly reflective and minimally absorptive in infrared wavelengths, preferably a polished gold coating. The tube itself may be fabricated from a another rigid material such as aluminum, nickel or stainless steel, as long as the inner surfaces are coated or otherwise treated to be highly reflective. Preferably, the collimator 22 has a rectangular cross-section, although other cross-sectional shapes, such as other polygonal shapes or circular, parabolic or elliptical shapes, may be employed in alternative embodiments. The inner walls of the collimator 22 diverge as they extend away from the mixer 20. Preferably, the inner walls of the collimator 22 are substantially straight and form an angle of about 7 degrees with respect to the longitudinal axis A—A. The collimator 22 aligns the infrared energy E to propagate in a direction that is generally parallel to the longitudinal axis A—A of the mixer 20 and the collimator 22, so that the infrared energy E will strike the surface of the filters 24 at an angle as close to 90 degrees as possible.

In a presently preferred embodiment, the collimator is about 7.5 inches in length. At its narrow end 22a, the cross-section of the collimator 22 is a rectangle of about 0.4 inches by 0.6 inches. At its wide end 22b, the collimator 22 has a rectangular cross-section of about 1.8 inches by 2.6 inches. Preferably, the collimator 22 aligns the infrared energy E to an angle of incidence (with respect to the longitudinal axis A—A) of about 0–15 degrees before the energy E impinges upon the filters 24. Of course, other dimensions or incidence angles may be employed in constructing and operating the collimator 22.

With further reference to FIGS. 1 and 6A, each concentrator 26 comprises a tapered surface oriented such that its wide end 26a is adapted to receive the infrared energy exiting the corresponding filter 24, and such that its narrow end 26b is adjacent to the corresponding detector 28. The inward-facing surfaces of the concentrators 26 have an inner surface coating which is highly reflective and minimally absorptive in infrared wavelengths, preferably a polished gold coating. The concentrators 26 themselves may be fabricated from a another rigid material such as aluminum, nickel or stainless steel, so long as their inner surfaces are coated or otherwise treated to be highly reflective.

Preferably, the concentrators 26 have a rectangular cross-section (as taken orthogonal to the longitudinal axis A—A), although other cross-sectional shapes, such as other polygonal shapes or circular, parabolic or elliptical shapes, may be employed in alternative embodiments. The inner walls of the concentrators converge as they extend toward the narrow end 26b. Preferably, the inner walls of the concentrators 26 are substantially straight and form an angle of about 8 degrees with respect to the longitudinal axis A—A. Such a configuration is adapted to concentrate infrared energy as it passes through the concentrators 26 from the wide end 26a to the narrow end 26b, before reaching the detectors 28.

In a presently preferred embodiment, each concentrator 26 is about 1.5 inches in length. At the wide end 26a, the cross-section of each concentrator 26 is a rectangle of about 0.6 inches by 0.57 inches. At the narrow end 26b, each concentrator 26 has a rectangular cross-section of about 0.177 inches by 0.177 inches. Of course, other dimensions or incidence angles may be employed in constructing the concentrators 26.

e. Filters

The filters 24 preferably comprise standard interference-type infrared filters, widely available from manufacturers such as Optical Coating Laboratory, Inc. ("OCLI") of Santa Rosa, Calif. In the embodiment illustrated in FIG. 1, a 3×4 array of filters 24 is positioned above a 3×4 array of detectors 28 and concentrators 26. As employed in this embodiment, the filters 24 are arranged in four groups of three filters having the same wavelength sensitivity. These four groups have bandpass center wavelengths of 7.15 $\mu m \pm 0.03$ $\mu m$, 8.40 $\mu m \pm 0.03$ $\mu m$, 9.48 $\mu m \pm 0.04$ $\mu m$, and 11.10 $\mu m \pm 0.04$ $\mu m$, respectively, which correspond to wavelengths around which water and glucose absorb electromagnetic radiation. Typical bandwidths for these filters range from 0.20 $\mu m$ to 0.50 $\mu m$.

In an alternative embodiment, the array of wavelength-specific filters 24 may be replaced with a single Fabry-Perot interferometer, which can provide wavelength sensitivity which varies as a sample of infrared energy E is taken from the material sample S. Thus, this embodiment permits the use of only one detector 28, the output signal of which varies in wavelength specificity over time. The output signal can be de-multiplexed based on the wavelength sensitivities induced by the Fabry-Perot interferometer, to provide a multiple-wavelength profile of the infrared energy E emitted by the material sample S. In this embodiment, the optical mixer 20 may be omitted, as only one detector 28 need be employed.

In still other embodiments, the array of filters 24 may comprise a filter wheel that rotates different filters with varying wavelength sensitivities over a single detector 24. Alternatively, an electronically tunable infrared filter may be employed in a manner similar to the Fabry-Perot interferometer discussed above, to provide wavelength sensitivity which varies during the detection process. In either of these embodiments, the optical mixer 20 may be omitted, as only one detector 28 need be employed.

f. Detectors

The detectors 28 may comprise any detector type suitable for sensing infrared energy, preferably in the mid-infrared wavelengths. For example, the detectors 28 may comprise mercury-cadmium-telluride ("MCT") detectors. A detector such as a Fermionics (Simi Valley, Calif.) model PV-9.1 with a PVA481-1 pre-amplifier is acceptable. Similar units from other manufacturers such as Graseby (Tampa, Fla.) can be substituted. Other suitable components for use as the detectors 28 include pyroelectric detectors, thermopiles, bolometers, silicon microbolometers and lead-salt focal plane arrays.

g. Control System

Figure 7:
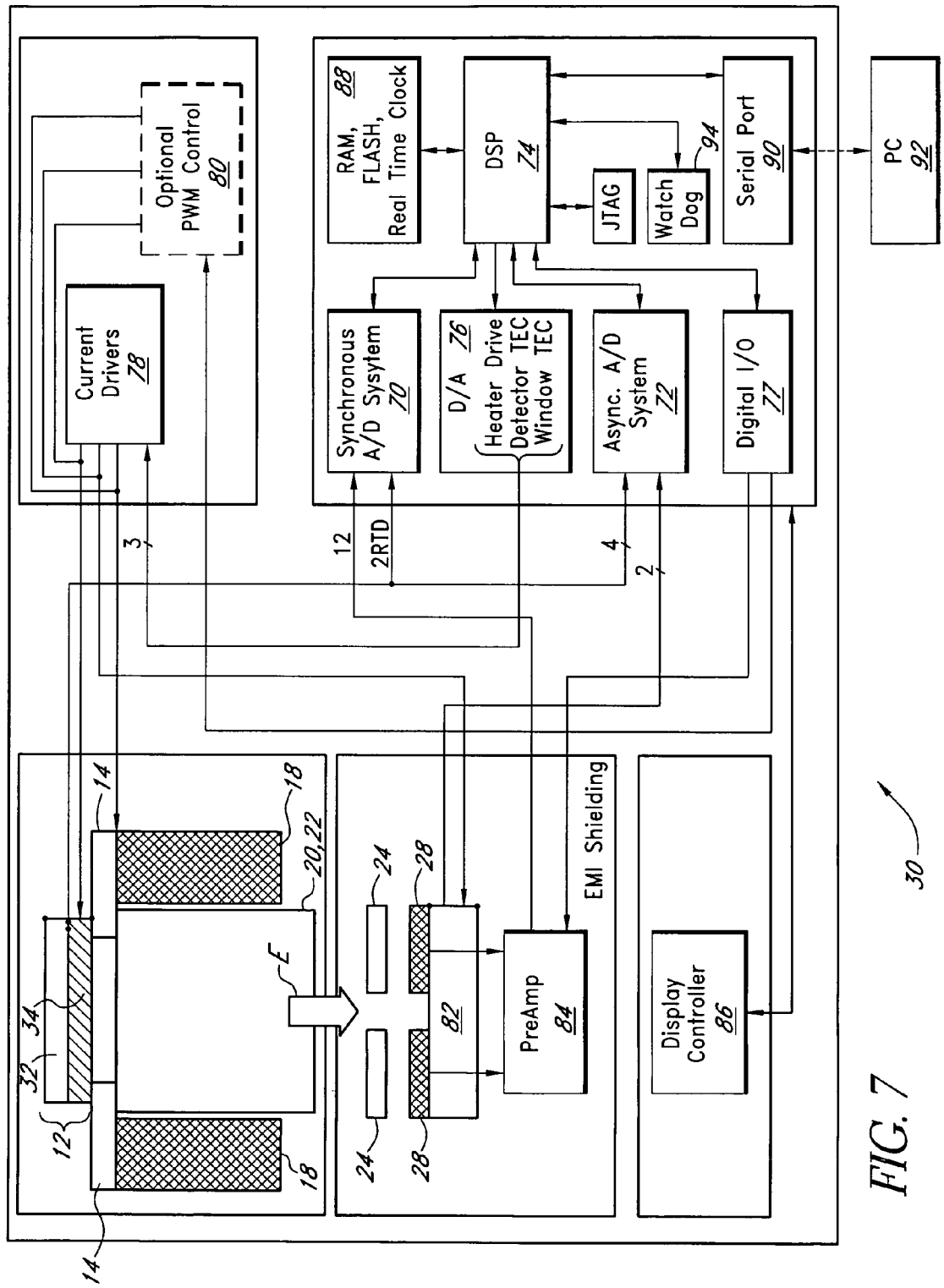
FIG. 7 is a schematic view of a control system for use with the noninvasive optical detection system.

FIG. 7 depicts the control system 30 in greater detail, as well as the interconnections between the control system 30 and other relevant portions of the noninvasive system 10. The control system 30 includes a temperature control subsystem and a data acquisition subsystem.

In the temperature control subsystem, temperature sensors (such as RTDs and/or thermistors) located in the window assembly 12 provide a window temperature signal to a synchronous analog-to-digital ("A/D") conversion system 70 and an asynchronous A/D conversion system 72. The A/D systems 70, 72 in turn provide a digital window temperature signal to a digital signal processor ("DSP") 74. The processor 74 executes a window temperature control algorithm and determines appropriate control inputs for the heater layer 34 of the window assembly 12 and/or for the cooling system 14, based on the information contained in the window temperature signal. The processor 74 outputs one or more digital control signals to a digital-to-analog ("D/A") conversion system 76 which in turn provides one or more analog control signals to current drivers 78. In response to the control signal(s), the current drivers 78 regulate the power supplied to the heater layer 34 and/or to the cooling system 14. In one embodiment, the processor 74 provides a control signal through a digital input/output ("I/O") device 77 to a pulse-width modulator ("PWM") control 80, which provides a signal that controls the operation of the current drivers 78. Alternatively, a low-pass filter (not shown) at the output of the PWM provides for continuous operation of the current drivers 78.

In another embodiment, temperature sensors may be located at the cooling system 14 and appropriately connected to the A/D system(s) and processor to provide closed-loop control of the cooling system as well.

In yet another embodiment, a detector cooling system 82 is located in thermally conductive relation to one or more of the detectors 28. The detector cooling system 82 may comprise any of the devices disclosed above as comprising the cooling system 14, and preferably comprises a Peltier-type thermoelectric device. The temperature control subsystem may also include temperature sensors, such as RTDs and/or thermistors, located in or adjacent to the detector cooling system 82, and electrical connections between these sensors and the asynchronous A/D system 72. The temperature sensors of the detector cooling system 82 provide detector temperature signals to the processor 74. In one embodiment, the detector cooling system 82 operates independently of the window temperature control system, and the detector cooling system temperature signals are sampled using the asynchronous A/D system 72. In accordance with the temperature control algorithm, the processor 74 determines appropriate control inputs for the detector cooling system 82, based on the information contained in the detector temperature signal. The processor 74 outputs digital control signals to the D/A conversion system 76 which in turn provides analog control signals to the current drivers 78. In response to the control signals, the current drivers 78 regulate the power supplied to the detector cooling system 14. In one embodiment, the processor 74 also provides a control signal through the digital I/O device 77 and the PWM control 80, to control the operation of the detector cooling system 82 by the current drivers 78. Alternatively, a low-pass filter (not shown) at the output of the PWM provides for continuous operation of the current drivers 78.

In the data acquisition subsystem, the detectors 28 respond to the infrared energy E incident thereon by passing one or more analog detector signals to a preamp 84. The preamp 84 amplifies the detector signals and passes them to the synchronous A/D system 70, which converts the detector signals to digital form and passes them to the processor 74. The processor 74 determines the concentrations of the analyte(s) of interest, based on the detector signals and a concentration-analysis algorithm and/or phase/concentration regression model stored in a memory module 88. The concentration-analysis algorithm and/or phase/concentration regression model may be developed according to any of the analysis methodologies discussed herein. The processor 74 may communicate the concentration results and/or other information to a display controller 86, which operates a display (not shown), such as a liquid crystal display ("LCD"), to present the information to the user.

A watchdog timer 94 may be employed to ensure that the processor 74 is operating correctly. If the watchdog timer 94 does not receive a signal from the processor 74 within a specified time, the watchdog timer 94 resets the processor 74. The control system may also include a joint test action group ("JTAG") interface 96 to enable testing of the noninvasive system 10.

In one embodiment, the synchronous A/D system 70 comprises a 20-bit, 14 channel system, and the asynchronous A/D system 72 comprises a 16-bit, 16 channel system. The preamp 84 may comprise a 12-channel preamp corresponding to an array of 12 detectors 28.

The control system may also include a serial port 90 or other conventional data port to permit connection to a personal computer 92. The personal computer 92 can be employed to update the algorithm(s) and/or phase/concentration regression model(s) stored in the memory module 88, or to download a compilation of analyte-concentration data from the noninvasive system 10. A real-time clock or other timing device may be accessible by the processor 74 to make any time-dependent calculations which may be desirable to a user.

2. Analysis Methodology

The detector(s) 28 of the noninvasive system 10 are used to detect the infrared energy E emitted by the material sample S in various desired wavelengths. At each measured wavelength, the material sample S emits infrared energy at an intensity which varies over time. The time-varying intensities arise largely in response to the use of the window assembly 12 (including its heater layer 34) and the cooling system 14 to induce a thermal gradient in the material sample S. As used herein, "thermal gradient" is a broad term and is used in its ordinary sense and refers, without limitation, to a difference in temperature and/or thermal energy between different locations, such as different depths, of a material sample, which can be induced by any suitable method of increasing or decreasing the temperature and/or thermal energy in one or more locations of the sample. As will be discussed in detail below, the concentration of an analyte of interest (such as glucose) in the material sample S can be determined with a device such as the noninvasive system 10, by comparing the time-varying intensity profiles of the various measured wavelengths.

Analysis methodologies are discussed herein within the context of detecting the concentration of glucose within a material sample, such as a tissue sample, which includes a large proportion of water. However, it will evident that these methodologies are not limited to this context and may be applied to the detection of a wide variety of analytes within a wide variety of sample types. It should also be understood that other suitable analysis methodologies and suitable variations of the disclosed methodologies may be employed in operating an analyte detection system, such as the noninvasive system 10.

Figure 8:
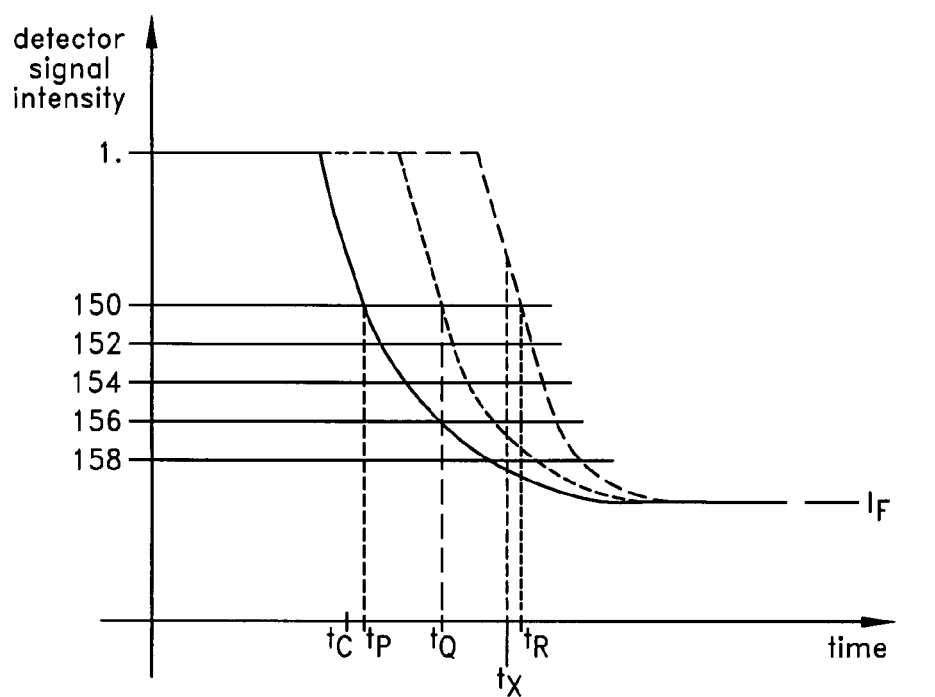
FIG. 8 depicts a first methodology for determining the concentration of an analyte of interest.

As shown in FIG. 8, a first reference signal P may be measured at a first reference wavelength. The first reference signal P is measured at a wavelength where water strongly absorbs (for example, 2.9 $\mu$m or 6.1 $\mu$m). Because water strongly absorbs radiation at these wavelengths, the detector signal intensity is reduced at those wavelengths. Moreover, at these wavelengths water absorbs the photon emissions emanating from deep inside the sample. The net effect is that a signal emitted at these wavelengths from deep inside the sample is not easily detected. The first reference signal P is thus a good indicator of thermal-gradient effects near the sample surface and may be known as a surface reference signal. This signal may be calibrated and normalized, in the absence of heating or cooling applied to the sample, to a baseline value of 1. For greater accuracy, more than one first reference wavelength may be measured. For example, both 2.9 $\mu$m and 6.1 $\mu$m may be chosen as first reference wavelengths.

As further shown in FIG. 8, a second reference signal R may also be measured. The second signal R may be measured at a wavelength where water has very low absorbance (for example, 3.6 $\mu$m or 4.2 $\mu$m). This second reference signal R thus provides the analyst with information concerning the deeper regions of the sample, whereas the first signal P provides information concerning the sample surface. This signal may also be calibrated and normalized, in the absence of heating or cooling applied to the sample, to a baseline value of 1. As with the first (surface) reference signal P, greater accuracy may be obtained by using more than one second (deep) reference signal R.

To determine analyte concentration, a third (analytical) signal Q is also measured. This signal is measured at an infrared absorbance peak of the selected analyte. The infrared absorbance peaks for glucose are in the range of about 6.5 $\mu$m to 11.0 $\mu$m. This detector signal may also be calibrated and normalized, in the absence of heating or cooling applied to the material sample S, to a baseline value of 1. As with the reference signals P, R, the analytical signal Q may be measured at more than one absorbance peak.

Optionally, or additionally, reference signals may be measured at wavelengths that bracket the analyte absorbance peak. These signals may be advantageously monitored at reference wavelengths which do not overlap the analyte absorbance peaks. Further, it is advantageous to measure reference wavelengths at absorbance peaks which do not overlap the absorbance peaks of other possible constituents contained in the sample.

a. Basic Thermal Gradient

As further shown in FIG. 8, the intensities of the signals P, Q, R are shown initially at the normalized baseline signal intensity of 1. This of course reflects the baseline radiative behavior of a test sample in the absence of applied heating or cooling. At a time $t_C$, the surface of the sample is subjected to a temperature event which induces a thermal gradient in the sample. The gradient can be induced by heating or cooling the sample surface. The example shown in FIG. 8 uses cooling, for example, using a 10° C. cooling event. In response to the cooling event, the intensities of the detector signals P, Q, R decrease over time.

Since the cooling of the sample is neither uniform nor instantaneous, the surface cools before the deeper regions of the sample cool. As each of the signals P, Q, R drop in intensity, a pattern emerges. Signal intensity declines as expected, but as the signals P, Q, R reach a given amplitude value (or series of amplitude values: 150, 152, 154, 156, 158), certain temporal effects are noted. After the cooling event is induced at $t_C$, the first (surface) reference signal P declines in amplitude most rapidly, reaching a checkpoint 150 first, at time $t_P$. This is due to the fact that the first reference signal P mirrors the sample's radiative characteristics near the surface of the sample. Since the sample surface cools before the underlying regions, the surface (first) reference signal P drops in intensity first.

Simultaneously, the second reference signal R is monitored. Since the second reference signal R corresponds to the radiation characteristics of deeper regions of the sample, which do not cool as rapidly as the surface (due to the time needed for the surface cooling to propagate into the deeper regions of the sample), the intensity of signal R does not decline until slightly later. Consequently, the signal R does not reach the magnitude 150 until some later time $t_R$. In other words, there exists a time delay between the time $t_P$ at which the amplitude of the first reference signal P reaches the checkpoint 150 and the time $t_R$ at which the second reference signal R reaches the same checkpoint 150. This time delay can be expressed as a phase difference $\Phi(\lambda)$. Additionally, a phase difference may be measured between the analytical signal Q and either or both reference signals P, R.

As the concentration of analyte increases, the amount of absorbance at the analytical wavelength increases. This reduces the intensity of the analytical signal Q in a concentration-dependent way. Consequently, the analytical signal Q reaches intensity 150 at some intermediate time $t_Q$. The higher the concentration of analyte, the more the analytical signal Q shifts to the left in FIG. 8. As a result, with increasing analyte concentration, the phase difference $\Phi(\lambda)$ decreases relative to the first (surface) reference signal P and increases relative to the second (deep tissue) reference signal R. The phase difference(s) $\Phi(\lambda)$ are directly related to analyte concentration and can be used to make accurate determinations of analyte concentration.

The phase difference $\Phi(\lambda)$ between the first (surface) reference signal P and the analytical signal Q is represented by the equation:

$$\Phi(\lambda) = |t_P - t_Q|$$

The magnitude of this phase difference decreases with increasing analyte concentration.

The phase difference $\Phi(\lambda)$ between the second (deep tissue) reference signal R and the analytical signal Q signal is represented by the equation:

$$\Phi(\lambda) = |t_Q - t_R|$$

The magnitude of this phase difference increases with increasing analyte concentration.

Accuracy may be enhanced by choosing several checkpoints, for example, 150, 152, 154, 156, and 158 and averaging the phase differences observed at each checkpoint. The accuracy of this method may be further enhanced by integrating the phase difference(s) continuously over the entire test period. Because in this example only a single temperature event (here, a cooling event) has been induced, the sample reaches a new lower equilibrium temperature and the signals stabilize at a new constant level $I_F$. Of course, the method works equally well with thermal gradients induced by heating or by the application or introduction of other forms of energy, such as but not limited to light, radiation, chemically induced heat, friction and vibration.

This methodology is not limited to the determination of phase difference. At any given time (for example, at a time $t_x$) the amplitude of the analytical signal Q may be compared to the amplitude of either or both of the reference signals P, R. The difference in amplitude may be observed and processed to determine analyte concentration.

This method, the variants disclosed herein, and the apparatus disclosed as suitable for application of the method(s), are not limited to the detection of in-vivo glucose concentration. The method and disclosed variants and apparatus may be used on human, animal, or even plant subjects, or on organic or inorganic compositions in a non-medical setting. The method may be used to take measurements of in-vivo or in-vitro samples of virtually any kind. The method is useful for measuring the concentration of a wide range of additional chemical analytes, including but not limited to, glucose, ethanol, insulin, water, carbon dioxide, blood oxygen, cholesterol, bilirubin, ketones, fatty acids, lipoproteins, albumin, urea, creatinine, white blood cells, red blood cells, hemoglobin, oxygenated hemoglobin, carboxyhemoglobin, organic molecules, inorganic molecules, pharmaceuticals, cytochrome, various proteins and chromophores, microcalcifications, hormones, as well as other chemical compounds. To detect a given analyte, one needs only to select appropriate analytical and reference wavelengths.

The method is adaptable and may be used to determine chemical concentrations in samples of body fluids (for example, blood, urine or saliva) once they have been extracted from a patient. In fact, the method may be used for the measurement of in-vitro samples of virtually any kind.

b. Modulated Thermal Gradient

In some embodiments of the methodology described above, a periodically modulated thermal gradient can be employed to make accurate determinations of analyte concentration.

As previously shown in FIG. 8, once a thermal gradient is induced in the sample, the reference and analytical signals P, Q, R fall out of phase with respect to each other. This phase difference $\Phi(\lambda)$ is present whether the thermal gradient is induced through heating or cooling. By alternatively subjecting the test sample to cyclic pattern of heating, cooling, or alternately heating and cooling, an oscillating thermal gradient may be induced in a sample for an extended period of time.

Figure 9:
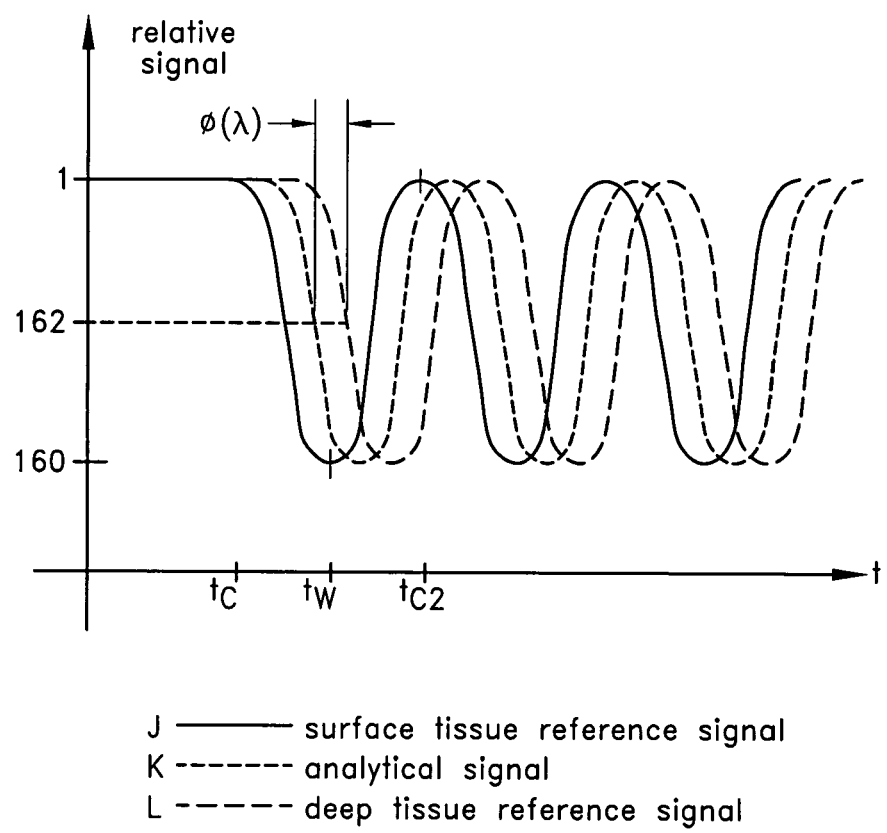
FIG. 9 depicts a second methodology for determining the concentration of an analyte of interest.

An oscillating thermal gradient is illustrated using a sinusoidally modulated gradient. FIG. 9 depicts detector signals emanating from a test sample. As with the methodology shown in FIG. 8, one or more reference signals J, L are measured. One or more analytical signals K are also monitored. These signals may be calibrated and normalized, in the absence of heating or cooling applied to the sample, to a baseline value of 1. FIG. 9 shows the signals after normalization. At some time $t_C$, a temperature event (for example, cooling) is induced at the sample surface. This causes a decline in the detector signal. As shown in FIG. 8, the signals (P, Q, R) decline until the thermal gradient disappears and a new equilibrium detector signal $I_F$ is reached. In the method shown in FIG. 9, as the gradient begins to disappear at a signal intensity 160, a heating event, at a time $t_W$, is induced in the sample surface. As a result the detector output signals J, K, L will rise as the sample temperature rises. At some later time $t_{C2}$, another cooling event is induced, causing the temperature and detector signals to decline. This cycle of cooling and heating may be repeated over a time interval of arbitrary length. Moreover, if the cooling and heating events are timed properly, a periodically modulated thermal gradient may be induced in the test sample.

As previously explained in the discussions relating to FIG. 8, the phase difference $\Phi(\lambda)$ may be measured and used to determine analyte concentration. FIG. 9 shows that the first (surface) reference signal J declines and rises in intensity first. The second (deep tissue) reference signal L declines and rises in a time-delayed manner relative to the first reference signal J. The analytical signal K exhibits a time/phase delay dependent on the analyte concentration. With increasing concentration, the analytical signal K shifts to the left in FIG. 9. As with FIG. 8, the phase difference $\Phi(\lambda)$ may be measured. For example, a phase difference $\Phi(\lambda)$ between the second reference signal L and the analytical signal K, may be measured at a set amplitude 162 as shown in FIG. 9. Again, the magnitude of the phase signal reflects the analyte concentration of the sample.

The phase-difference information compiled by any of the methodologies disclosed herein can correlated by the control system 30 (see FIG. 1) with previously determined phase-difference information to determine the analyte concentration in the sample. This correlation could involve comparison of the phase-difference information received from analysis of the sample, with a data set containing the phase-difference profiles observed from analysis of wide variety of standards of known analyte concentration. In one embodiment, a phase/concentration curve or regression model is established by applying regression techniques to a set of phase-difference data observed in standards of known analyte concentration. This curve is used to estimate the analyte concentration in a sample based on the phase-difference information received from the sample.

Advantageously, the phase difference $\Phi(\lambda)$ may be measured continuously throughout the test period. The phase-difference measurements may be integrated over the entire test period for an extremely accurate measure of phase difference $\Phi(\lambda)$. Accuracy may also be improved by using more than one reference signal and/or more than one analytical signal.

As an alternative or as a supplement to measuring phase difference(s), differences in amplitude between the analytical and reference signal(s) may be measured and employed to determine analyte concentration. Additional details relating to this technique and not necessary to repeat here may be found in U.S. patent application Ser. No. 09/538,164, incorporated by reference below.

Additionally, these methods may be advantageously employed to simultaneously measure the concentration of one or more analytes. By choosing reference and analyte wavelengths that do not overlap, phase differences can be simultaneously measured and processed to determine analyte concentrations. Although FIG. 9 illustrates the method used in conjunction with a sinusoidally modulated thermal gradient, the principle applies to thermal gradients conforming to any periodic function. In more complex cases, analysis using signal processing with Fourier transforms or other techniques allows accurate determinations of phase difference $\Phi(\lambda)$ and analyte concentration.

Figure 10:
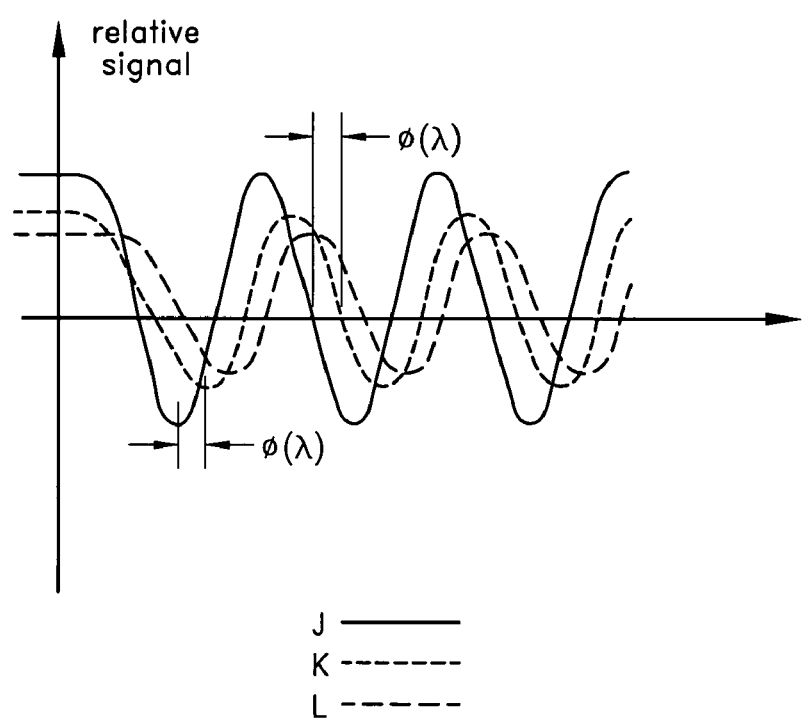
FIG. 10 depicts a third methodology for determining the concentration of an analyte of interest.

As shown in FIG. 10, the magnitude of the phase differences may be determined by measuring the time intervals between the amplitude peaks (or troughs) of the reference signals J, L and the analytical signal K. Alternatively, the time intervals between the "zero crossings" (the point at which the signal amplitude changes from positive to negative, or negative to positive) may be used to determine the phase difference between the analytical signal K and the reference signals J, L. This information is subsequently processed and a determination of analyte concentration may then be made. This particular method has the advantage of not requiring normalized signals.

As a further alternative, two or more driving frequencies may be employed to determine analyte concentrations at selected depths within the sample. A slow (for example, 1 Hz) driving frequency creates a thermal gradient which penetrates deeper into the sample than the gradient created by a fast (for example, 3 Hz) driving frequency. This is because the individual heating and/or cooling events are longer in duration where the driving frequency is lower. Thus, the use of a slow driving frequency provides analyte-concentration information from a deeper "slice" of the sample than does the use of a fast driving frequency.

It has been found that when analyzing a sample of human skin, a temperature event of 10° C. creates a thermal gradient which penetrates to a depth of about 150 $\mu$m, after about 500 ms of exposure. Consequently, a cooling/heating cycle or driving frequency of 1 Hz provides information to a depth of about 150 $\mu$m. It has also been determined that exposure to a temperature event of 10° C. for about 167 ms creates a thermal gradient that penetrates to a depth of about 50 $\mu$m. Therefore, a cooling/heating cycle of 3 Hz provides information to a depth of about 50 $\mu$m. By subtracting the detector signal information measured at a 3 Hz driving frequency from the detector signal information measured at a 1 Hz driving frequency, one can determine the analyte concentration(s) in the region of skin between 50 and 150 $\mu$m. Of course, a similar approach can be used to determine analyte concentrations at any desired depth range within any suitable type of sample.

Figure 11:
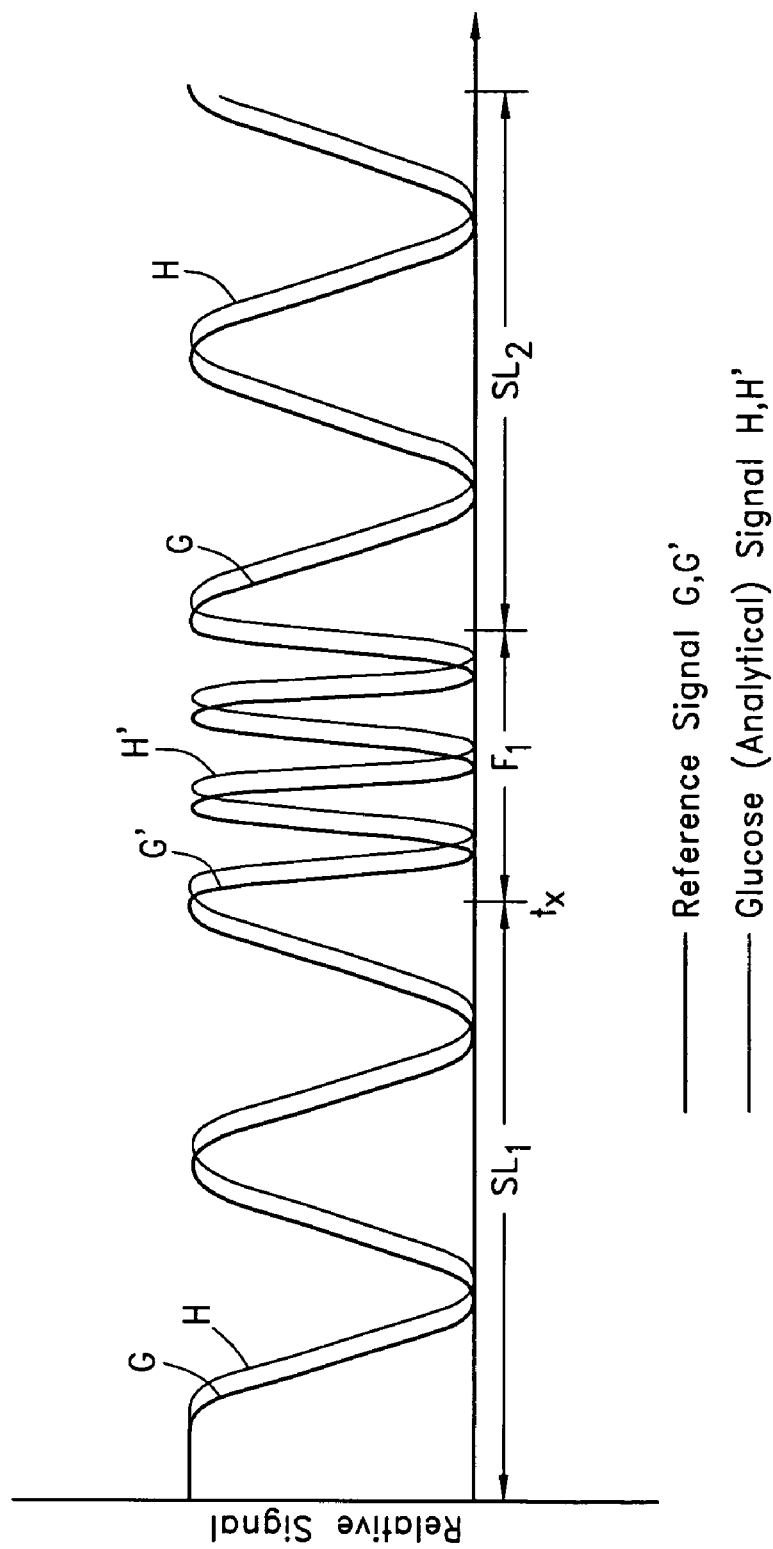
FIG. 11 depicts a fourth methodology for determining the concentration of an analyte of interest.

As shown in FIG. 11, alternating deep and shallow thermal gradients may be induced by alternating slow and fast driving frequencies. As with the methods described above, this variation also involves the detection and measurement of phase differences $\Phi(\lambda)$ between reference signals G, G' and analytical signals H, H'. Phase differences are measured at both fast (for example, 3 Hz) and slow (for example, 1 Hz) driving frequencies. The slow driving frequency may continue for an arbitrarily chosen number of cycles (in region $SL_1$), for example, two full cycles. Then the fast driving frequency is employed for a selected duration, in region $F_1$. The phase difference data is compiled in the same manner as disclosed above. In addition, the fast frequency (shallow sample) phase difference data may be subtracted from the slow frequency (deep sample) data to provide an accurate determination of analyte concentration in the region of the sample between the gradient penetration depth associated with the fast driving frequency and that associated with the slow driving frequency.

Figure 12:
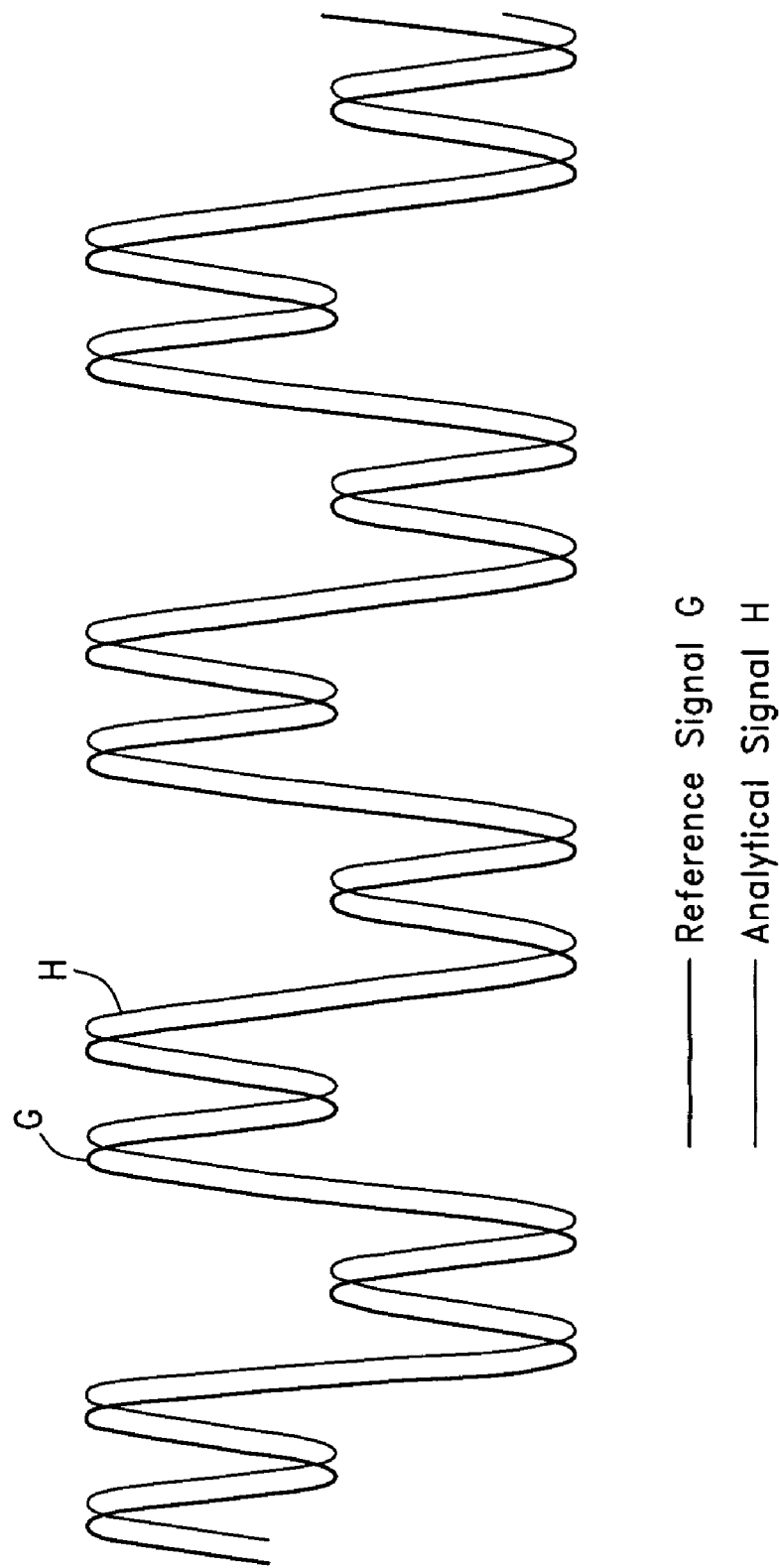
FIG. 12 depicts a fifth methodology for determining the concentration of an analyte of interest.

The driving frequencies (for example, 1 Hz and 3 Hz) can be multiplexed as shown in FIG. 12. The fast (3 Hz) and slow (1 Hz) driving frequencies can be superimposed rather than sequentially implemented. During analysis, the data can be separated by frequency (using Fourier transform or other techniques) and independent measurements of phase delay at each of the driving frequencies may be calculated. Once resolved, the two sets of phase delay data are processed to determine absorbance and analyte concentration.

Additional details not necessary to repeat here may be found in U.S. Pat. No. 6,198,949, titled SOLID-STATE NON-INVASIVE INFRARED ABSORPTION SPECTROMETER FOR THE GENERATION AND CAPTURE OF THERMAL GRADIENT SPECTRA FROM LIVING TISSUE, issued Mar. 6, 2001; U.S. Pat. No. 6,161,028, titled METHOD FOR DETERMINING ANALYTE CONCENTRATION USING PERIODIC TEMPERATURE MODULATION AND PHASE DETECTION, issued Dec. 12, 2000; U.S. Pat. No. 5,877,500, titled MULTICHANNEL INFRARED DETECTOR WITH OPTICAL CONCENTRATORS FOR EACH CHANNEL, issued on Mar. 2, 1999; U.S. patent application Ser. No. 09/538,164, filed Mar. 30, 2000 and titled METHOD AND APPARATUS FOR DETERMINING ANALYTE CONCENTRATION USING PHASE AND MAGNITUDE DETECTION OF A RADIATION TRANSFER FUNCTION; U.S. Provisional Patent Application No. 60/336,404, filed Oct. 29, 2001 and titled WINDOW ASSEMBLY; U.S. Provisional Patent Application No. 60/340,435, filed Dec. 12, 2001 and titled CONTROL SYSTEM FOR BLOOD CONSTITUENT MONITOR; U.S. Provisional Patent Application No. 60/340,654, filed Dec. 12, 2001 and titled SYSTEM AND METHOD FOR CONDUCTING AND DETECTING INFRARED RADIATION; U.S. Provisional Patent Application No. 60/336,294, filed Oct. 29, 2001 and titled METHOD AND DEVICE FOR INCREASING ACCURACY OF BLOOD CONSTITUENT MEASUREMENT; and U.S. Provisional Patent Application No. 60/339,116, filed Nov. 7, 2001 and titled METHOD AND APPARATUS FOR IMPROVING CLINICALLY SIGNIFICANT ACCURACY OF ANALYTE MEASUREMENTS. The entire disclosure of all of the above-mentioned patents, patent applications and publications (less any appendices thereto) are hereby incorporated by reference herein and made a part of this specification.

B. Whole-Blood Detection System

Figure 13:
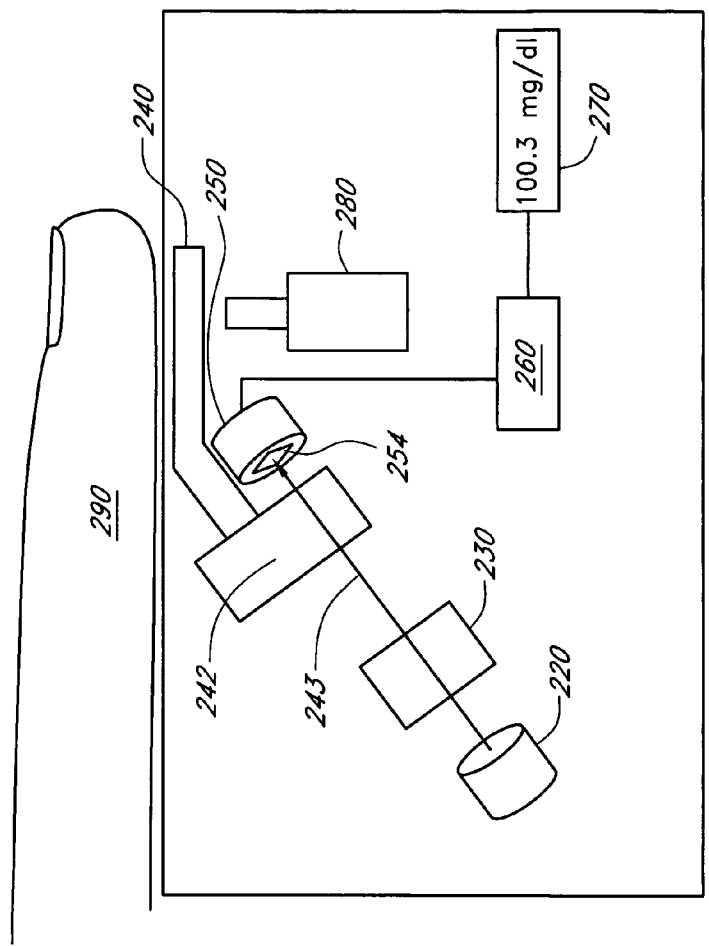
FIG. 13 is a schematic view of a reagentless whole-blood detection system.

FIG. 13 is a schematic view of a reagentless whole-blood analyte detection system 200 (hereinafter "whole-blood system") in a preferred configuration. The whole-blood system 200 may comprise a radiation source 220, a filter 230, a cuvette 240 that includes a sample cell 242, and a radiation detector 250. The whole-blood system 200 preferably also comprises a signal processor 260 and a display 270. Although a cuvette 240 is shown here, other sample elements, as described below, could also be used in the system 200. The whole-blood system 200 can also comprise a sample extractor 280, which can be used to access bodily fluid from an appendage, such as the finger 290, forearm, or any other suitable location.

As used herein, the terms "whole-blood analyte detection system" and "whole-blood system" are broad, synonymous terms and are used in their ordinary sense and refer, without limitation, to analyte detection devices which can determine the concentration of an analyte in a material sample by passing electromagnetic radiation into the sample and detecting the absorbance of the radiation by the sample. As used herein, the term "whole-blood" is a broad term and is used in its ordinary sense and refers, without limitation, to blood that has been withdrawn from a patient but that has not been otherwise processed, for example, it has not been hemolyzed, lyophilized, centrifuged, or separated in any other manner, after being removed from the patient. Whole-blood may contain amounts of other fluids, such as interstitial fluid or intracellular fluid, which may enter the sample during the withdrawal process or are naturally present in the blood. It should be understood, however, that the whole-blood system 200 disclosed herein is not limited to analysis of whole-blood, as the whole-blood system 200 may be employed to analyze other substances, such as saliva, urine, sweat, interstitial fluid, intracellular fluid, hemolyzed, lyophilized, or centrifuged blood or any other organic or inorganic materials.

The whole-blood system 200 may comprise a near-patient testing system. As used herein, "near-patient testing system" is a broad term and is used in its ordinary sense, and includes, without limitation, test systems that are configured to be used where the patient is rather than exclusively in a laboratory, for example, systems that can be used at a patient's home, in a clinic, in a hospital, or even in a mobile environment. Users of near-patient testing systems can include patients, family members of patients, clinicians, nurses; or doctors. A "near-patient testing system" could also include a "point-of-care" system.

The whole-blood system 200 may in one embodiment be configured to be operated easily by the patient or user. As such, the system 200 is preferably a portable device. As used herein, "portable" is a broad term and is used in its ordinary sense and means, without limitation, that the system 200 can be easily transported by the patient and used where convenient. For example, the system 200 is advantageously small. In one preferred embodiment, the system 200 is small enough to fit into a purse or backpack. In another embodiment, the system 200 is small enough to fit into a pants pocket. In still another embodiment, the system 200 is small enough to be held in the palm of a hand of the user.

Some of the embodiments described herein employ a sample element to hold a material sample, such as a sample of biological fluid. As used herein, "sample element" is a broad term and is used in its ordinary sense and includes, without limitation, structures that have a sample cell and at least one sample cell wall, but more generally includes any of a number of structures that can hold, support or contain a material sample and that allow electromagnetic radiation to pass through a sample held, supported or contained thereby; for example, a cuvette, test strip, and so forth. As used herein, the term "disposable" when applied to a component, such as a sample element, is a broad term and is used in its ordinary sense and means, without limitation, that the component in question is used a finite number of times and then discarded. Some disposable components are used only once and then discarded. Other disposable components are used more than once and then discarded.

The radiation source 220 of the whole-blood system 200 emits electromagnetic radiation in any of a number of spectral ranges, for example, within infrared wavelengths; in the mid-infrared wavelengths; above about 0.8 $\mu$m; between about 5.0 $\mu$m and about 20.0 $\mu$m; and/or between about 5.25 $\mu$m and about 12.0 $\mu$m. However, in other embodiments the whole-blood system 200 may employ a radiation source 220 which emits in wavelengths found anywhere from the visible spectrum through the microwave spectrum, for example anywhere from about 0.4 $\mu$m to greater than about 100 $\mu$m. In still further embodiments the radiation source emits electromagnetic radiation in wavelengths between about 3.5 $\mu$m and about 14 $\mu$m, or between about 0.8 $\mu$m and about 2.5 $\mu$m, or between about 2.5 $\mu$m and about 20 $\mu$m, or between about 20 $\mu$m and about 100 $\mu$m, or between about 6.85 $\mu$m and about 10.10 $\mu$m. As used herein, "source" is a broad term, and is used in its ordinary sense and further refers, without limitation, to anything that emits electromagnetic radiation, or that causes electromagnetic radiation to be emitted.

The radiation emitted from the source 220 is in one embodiment modulated at a frequency between about one-half hertz and about one hundred hertz, in another embodiment between about 2.5 hertz and about 7.5 hertz, in still another embodiment at about 50 hertz, and in yet another embodiment at about 5 hertz. With a modulated radiation source, ambient light sources, such as a flickering fluorescent lamp, can be more easily identified and rejected when analyzing the radiation incident on the detector 250. One source that is suitable for this application is produced by Ion Optics, Inc., and sold under the part number NL5LNC.

The filter 230 permits electromagnetic radiation of selected wavelengths to pass through and impinge upon the cuvette/sample element 240. Preferably, the filter 230 permits radiation at least at about the following wavelengths to pass through to the cuvette/sample element: 3.9 $\mu$m, 4.0 $\mu$m, 4.05 $\mu$m, 4.2 $\mu$m, 4.75 $\mu$m, 4.95 $\mu$m, 5.25 $\mu$m, 6.12 $\mu$m, 7.4 $\mu$m, 8.0 $\mu$m, 8.45 $\mu$m, 9.25 $\mu$m, 9.5 $\mu$m, 9.65 $\mu$m, 10.4 $\mu$m, 12.2 $\mu$m. In another embodiment, the filter 230 permits radiation at least at about the following wavelengths to pass through to the cuvette/sample element: 5.25 $\mu$m, 6.12 $\mu$m, 6.8 $\mu$m, 8.03 $\mu$m, 8.45 $\mu$m, 9.25 $\mu$m, 9.65 $\mu$m, 10.4 $\mu$m, 12 $\mu$m. In still another embodiment, the filter 230 permits radiation at least at about the following wavelengths to pass through to the cuvette/sample element: 6.85 $\mu$m, 6.97 $\mu$m, 7.39 $\mu$m, 8.23 $\mu$m, 8.62 $\mu$m, 9.02 $\mu$m, 9.22 $\mu$m, 9.43 $\mu$m, 9.62 $\mu$m, and 10.10 $\mu$m. The sets of wavelengths recited above correspond to specific embodiments within the scope of this disclosure. Furthermore, other subsets of the foregoing sets or other combinations of wavelengths can be selected. Finally, other sets of wavelengths can be selected within the scope of this disclosure based on cost of production, development time, availability, and other factors relating to cost, manufacturability, and time to market of the filters used to generate the selected wavelengths, and/or reduction of the total number of filters needed.

In one embodiment, the filter 230 is capable of cycling its passband among a variety of narrow spectral bands or a variety of selected wavelengths. The filter 230 may thus comprise a solid-state tunable infrared filter, such as that available from Ion Optics, Inc. The filter 230 could also be implemented as a filter wheel with a plurality of fixed-passband filters mounted on the wheel, generally perpendicular to the direction of the radiation emitted by the source 220. Rotation of the filter wheel alternately presents filters that pass radiation at wavelengths that vary in accordance with the filters as they pass through the field of view of the detector 250.

The detector 250 preferably comprises a 3 mm long by 3 mm wide pyroelectric detector. Suitable examples are produced by DIAS Angewandte Sensorik GmbH of Dresden, Germany, or by BAE Systems (such as its TGS model detector). The detector 250 could alternatively comprise a thermopile, a bolometer, a silicon microbolometer, a lead-salt focal plane array, or a mercury-cadmium-telluride ("MCT") detector. Whichever structure is used as the detector 250, it is desirably configured to respond to the radiation incident upon its active surface 254 to produce electrical signals that correspond to the incident radiation.

In one embodiment, the sample element comprises a cuvette 240 which in turn comprises a sample cell 242 configured to hold a sample of tissue and/or fluid (such as whole-blood, blood components, interstitial fluid, intercellular fluid, saliva, urine, sweat and/or other organic or inorganic materials) from a patient within its sample cell. The cuvette 240 is installed in the whole-blood system 200 with the sample cell 242 located at least partially in the optical path 243 between the radiation source 220 and the detector 250. Thus, when radiation is emitted from the source 220 through the filter 230 and the sample cell 242 of the cuvette 240, the detector 250 detects the radiation signal strength at the wavelength(s) of interest. Based on this signal strength, the signal processor 260 determines the degree to which the sample in the cell 242 absorbs radiation at the detected wavelength(s). The concentration of the analyte of interest is then determined from the absorption data via any suitable spectroscopic technique.

As shown in FIG. 13, the whole-blood system 200 can also comprise a sample extractor 280. As used herein, the term "sample extractor" is a broad term and is used in its ordinary sense and refers, without limitation, to any device which is suitable for drawing a sample material, such as whole-blood, other bodily fluids, or any other sample material, through the skin of a patient. In various embodiments, the sample extractor may comprise a lance, laser lance, iontophoretic sampler, gas-jet, fluid-jet or particle-jet perforator, ultrasonic enhancer (used with or without a chemical enhancer), or any other suitable device.

As shown in FIG. 13, the sample extractor 280 could form an opening in an appendage, such as the finger 290, to make whole-blood available to the cuvette 240. It should be understood that other appendages could be used to draw the sample, including but not limited to the forearm. With some embodiments of the sample extractor 280, the user forms a tiny hole or slice through the skin, through which flows a sample of bodily fluid such as whole-blood. Where the sample extractor 280 comprises a lance (see FIG. 14), the sample extractor 280 may comprise a sharp cutting implement made of metal or other rigid materials. One suitable laser lance is the Lasette Plus® produced by Cell Robotics International, Inc. of Albuquerque, N.Mex. If a laser lance, iontophoretic sampler, gas-jet or fluid-jet perforator is used as the sample extractor 280, it could be incorporated into the whole-blood system 200 (see FIG. 13), or it could be a separate device.

Additional information on laser lances can be found in U.S. Pat. No. 5,908,416, issued Jun. 1, 1999, titled LASER DERMAL PERFORATOR; the entirety of this patent is hereby incorporated by reference herein and made a part of this specification. One suitable gas-jet, fluid-jet or particle-jet perforator is disclosed in U.S. Pat. No. 6,207,400, issued Mar. 27, 2001, titled NON- OR MINIMALLY INVASIVE MONITORING METHODS USING PARTICLE DELIVERY METHODS; the entirety of this patent is hereby incorporated by reference herein and made a part of this specification. One suitable iontophoretic sampler is disclosed in U.S. Pat. No. 6,298,254, issued Oct. 2, 2001, titled DEVICE FOR SAMPLING SUBSTANCES USING ALTERNATING POLARITY OF IONTOPHORETIC CURRENT; the entirety of this patent is hereby incorporated by reference herein and made a part of this specification. One suitable ultrasonic enhancer, and chemical enhancers suitable for use therewith, are disclosed in U.S. Pat. No. 5,458,140, issued Oct. 17, 1995, titled ENHANCEMENT OF TRANSDERMAL MONITORING APPLICATIONS WITH ULTRASOUND AND CHEMICAL ENHANCERS; the entire disclosure of this patent is hereby incorporated by reference and made a part of this specification.

Figure 14:
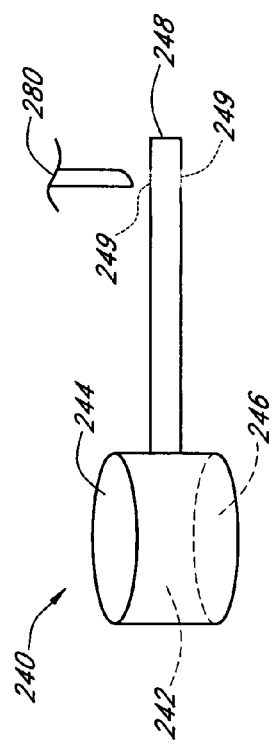
FIG. 14 is a perspective view of one embodiment of a cuvette for use with the reagentless whole-blood detection system.

FIG. 14 shows one embodiment of a sample element, in the form of a cuvette 240, in greater detail. The cuvette 240 further comprises a sample supply passage 248, a pierceable portion 249, a first window 244, and a second window 246, with the sample cell 242 extending between the first and second windows 244, 246. In one embodiment, the cuvette 240 does not have a second window 246. The first window 244 (or second window 246) is one form of a sample cell wall; in other embodiments of the sample elements and cuvettes disclosed herein, any sample cell wall may be used that at least partially contains, holds or supports a material sample, such as a biological fluid sample, and which is transmissive of at least some bands of electromagnetic radiation, and which may but need not be transmissive of electromagnetic radiation in the visible range. The pierceable portion 249 is an area of the sample supply passage 248 that can be pierced by suitable embodiments of the sample extractor 280. Suitable embodiments of the sample extractor 280 can pierce the portion 249 and the appendage 290 to create a wound in the appendage 290 and to provide an inlet for the blood or other fluid from the wound to enter the cuvette 240. (The sample extractor 280 is shown on the opposite side of the sample element in FIG. 14, as compared to FIG. 13, as it may pierce the pierceable portion 249 from either side.)

The windows 244, 246 are preferably optically transmissive in the range of electromagnetic radiation that is emitted by the source 220, or that is permitted to pass through the filter 230. In one embodiment, the material that makes up the windows 244, 246 is completely transmissive, that is, it does not absorb any of the electromagnetic radiation from the source 220 and filter 230 that is incident upon it. In another embodiment, the material of the windows 244, 246 has some absorption in the electromagnetic range of interest, but its absorption is negligible. In yet another embodiment, the absorption of the material of the windows 244, 246 is not negligible, but it is known and stable for a relatively long period of time. In another embodiment, the absorption of the windows 244, 246 is stable for only a relatively short period of time, but the whole-blood system 200 is configured to observe the absorption of the material and eliminate it from the analyte measurement before the material properties can change measurably.

The windows 244, 246 are made of polypropylene in one embodiment. In another embodiment, the windows 244, 246 are made of polyethylene. Polyethylene and polypropylene are materials having particularly advantageous properties for handling and manufacturing, as is known in the art. Also, polypropylene can be arranged in a number of structures, for example, isotactic, atactic and syndiotactic, which may enhance the flow characteristics of the sample in the sample element. Preferably the windows 244, 246 are made of durable and easily manufactureable materials, such as the above-mentioned polypropylene or polyethylene, or silicon or any other suitable material. The windows 244, 246 can be made of any suitable polymer, which can be isotactic, atactic or syndiotactic in structure.

The distance between the windows 244, 246 comprises an optical pathlength and can be between about 1 $\mu$m and about 100 $\mu$m. In one embodiment, the optical pathlength is between about 10 $\mu$m and about 40 $\mu$m, or between about 25 $\mu$m and about 60 $\mu$m, or between about 30 $\mu$m and about 50 $\mu$m. In still another embodiment, the optical pathlength is about 25 $\mu$m. The transverse size of each of the windows 244, 246 is preferably about equal to the size of the detector 250. In one embodiment, the windows are round with a diameter of about 3 mm. In this embodiment, where the optical pathlength is about 25 $\mu$m the volume of the sample cell 242 is about 0.177 $\mu$L. In one embodiment, the length of the sample supply passage 248 is about 6 mm, the height of the sample supply passage 248 is about 1 mm, and the thickness of the sample supply passage 248 is about equal to the thickness of the sample cell, for example, 25 $\mu$m. The volume of the sample supply passage is about 0.150 $\mu$L. Thus, the total volume of the cuvette 240 in one embodiment is about 0.327 $\mu$L. Of course, the volume of the cuvette 240/sample cell 242 can vary, depending on many variables, such as the size and sensitivity of the detectors 250, the intensity of the radiation emitted by the source 220, the expected flow properties of the sample, and whether flow enhancers (discussed below) are incorporated into the cuvette 240. The transport of fluid to the sample cell 242 is achieved preferably through capillary action, but may also be achieved through wicking, or a combination of wicking and capillary action.

Figure 16:
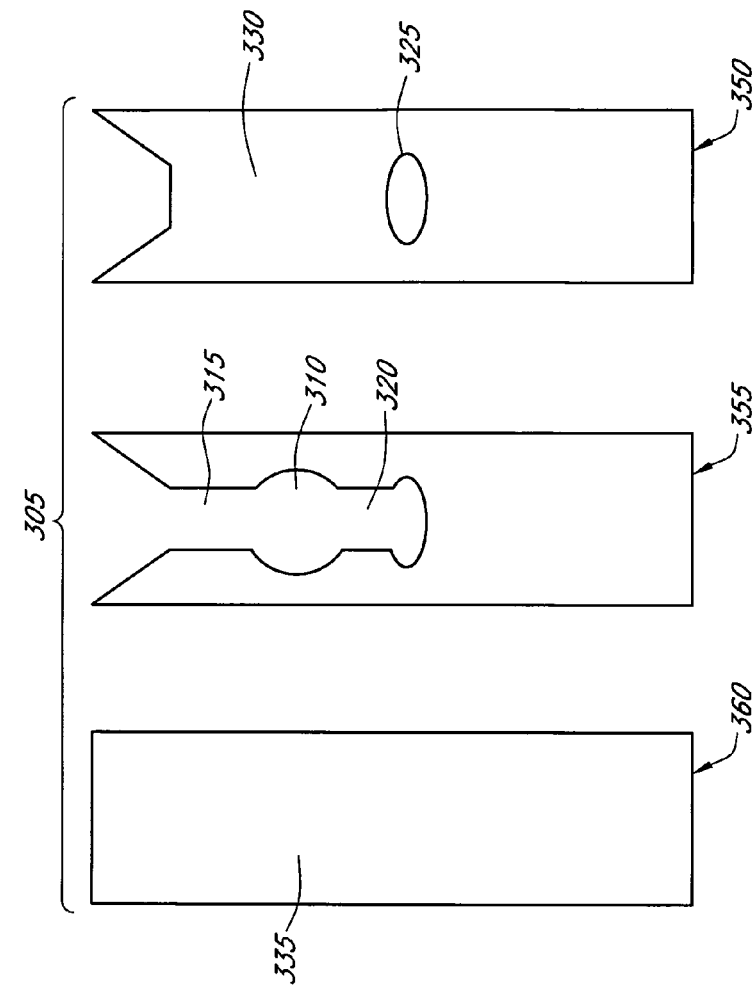
FIG. 16 is a disassembled plan view of the cuvette of FIG. 15.
Figure 17:
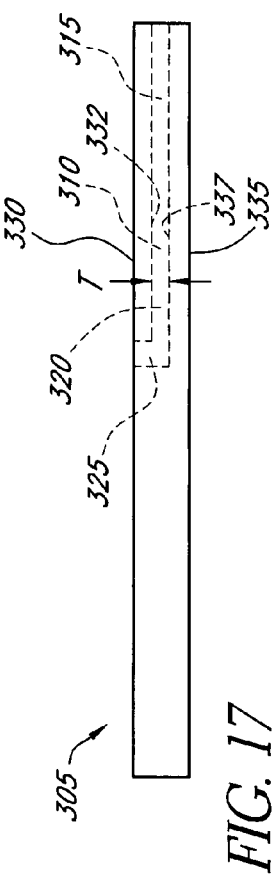
FIG. 17 is a side view of the cuvette of FIG. 15.
Figure 15:
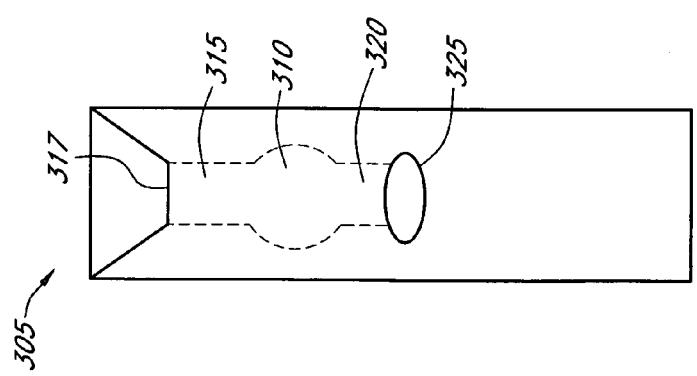
FIG. 15 is a plan view of another embodiment of a cuvette for use with the reagentless whole-blood detection system.
Figure 16A:
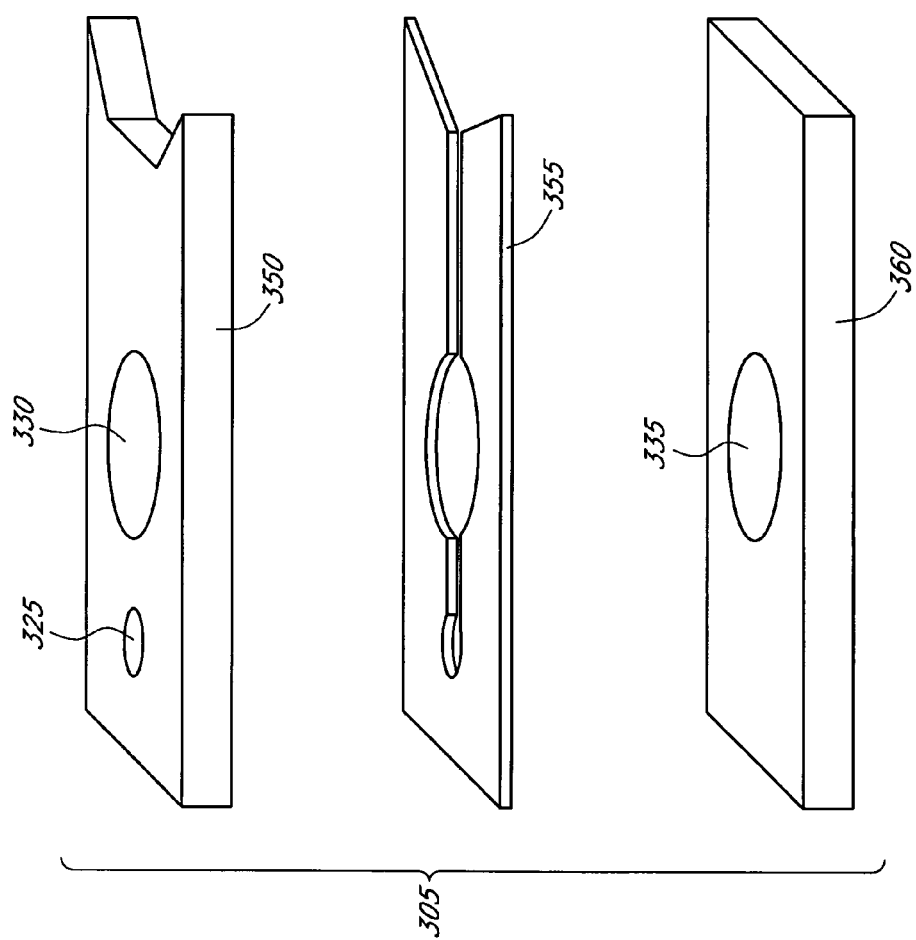
FIG. 16A is an exploded perspective view of the cuvette of FIG. 15.

FIGS. 15 through 17 depict another embodiment of a cuvette 305 that could be used in connection with the whole-blood system 200. The cuvette 305 comprises a sample cell 310, a sample supply passage 315, an air vent passage 320, and a vent 325. As best seen in FIGS. 16, 16A and 17, the cuvette also comprises a first sample cell window 330 having an inner side 332, and a second sample cell window 335 having an inner side 337. As discussed above, the first and second sample cell windows 330, 335 in some embodiments also comprise sample cell walls. The cuvette 305 also comprises an opening 317 at the end of the sample supply passage 315 opposite the sample cell 310. The cuvette 305 is preferably about ¼–⅛ inch wide and about ¾ inch long; however, other dimensions are possible while still achieving the advantages of the cuvette 305.

The sample cell 310 is defined between the inner side 332 of the first sample cell window 330 and the inner side 337 of the second sample cell window 335. The perpendicular distance T between the two inner sides 332, 337 comprises an optical pathlength that can be between about 1 $\mu$m and about 1.22 mm. The optical pathlength can alternatively be between about 1 $\mu$m and about 100 $\mu$m. The optical pathlength could still alternatively be about 80 $\mu$m, but is preferably between about 10 $\mu$m and about 50 $\mu$m. In another embodiment, the optical pathlength is about 25 $\mu$m. The first and second windows 330, 335 are preferably formed from any of the materials discussed above as possessing sufficient radiation transmissivity. The thickness of each window is preferably as small as possible without overly weakening the sample cell 310 or cuvette 305.

Once a wound is made in the appendage 290, the opening 317 of the sample supply passage 315 of the cuvette 305 is placed in contact with the fluid that flows from the wound. In another embodiment, the sample is obtained without creating a wound, for example as is done with a saliva sample. In that case, the opening 317 of the sample supply passage 315 of the cuvette 305 is placed in contact with the fluid obtained without creating a wound. The fluid is then transported through the sample supply passage 315 and into the sample cell 310 via capillary action. The air vent passage 320 improves the capillary action by preventing the buildup of air pressure within the cuvette and allowing the blood to displace the air as the blood flows therein.

Other mechanisms may be employed to transport the sample to the sample cell 310. For example, wicking could be used by providing a wicking material in at least a portion of the sample supply passage 315. In another variation, wicking and capillary action could be used together to transport the sample to the sample cell 310. Membranes could also be positioned within the sample supply passage 315 to move the blood while at the same time filtering out components that might complicate the optical measurement performed by the whole-blood system 200.

FIGS. 16 and 16A depict one approach to constructing the cuvette 305. In this approach, the cuvette 305 comprises a first layer 350, a second layer 355, and a third layer 360. The second layer 355 is positioned between the first layer 350 and the third layer 360. The first layer 350 forms the first sample cell window 330 and the vent 325. As mentioned above, the vent 325 provides an escape for the air that is in the sample cell 310. While the vent 325 is shown on the first layer 350, it could also be positioned on the third layer 360, or could be a cutout in the second layer 355, and would then be located between the first layer 350 and the third layer 360 The third layer 360 forms the second sample cell window 335.

The second layer 355 may be formed entirely of an adhesive that joins the first and third layers 350, 360. In other embodiments, the second layer 355 may be formed from similar materials as the first and third layers 350, 360, or any other suitable material. The second layer 355 may also be formed as a carrier with an adhesive deposited on both sides thereof. The second layer 355 forms the sample supply passage 315, the air vent passage 320, and the sample cell 310. The thickness of the second layer 355 can be between about 1 $\mu$m and about 1.22 mm. This thickness can alternatively be between about 1 $\mu$m and about 100 $\mu$m. This thickness could alternatively be about 80 $\mu$m, but is preferably between about 10 $\mu$m and about 50 $\mu$m. In another embodiment, the second layer thickness is about 25 $\mu$m.

In other embodiments, the second layer 355 can be constructed as an adhesive film having a cutout portion to define the sample supply and air vent passages 315, 320, or as a cutout surrounded by adhesive.

Further information can be found in U.S. patent application Ser. No. 10/055,875, filed Jan. 21, 2002, titled REAGENT-LESS WHOLE-BLOOD GLUCOSE METER. The entire contents of this patent application are hereby incorporated by reference herein and made a part of this specification.

II. Layered Spectroscopic Sample Element with Microporous Membrane

Disclosed in this section are various embodiments of a sample holder that can be used with the noninvasive system 10 and the whole-blood system 200 described above. Specifically, the sample holders disclosed in this section can be used in place of the cuvette 240 described above in connection with the whole-blood system 200. Additionally, any of the sample holders disclosed in this section can also be affixed to the window assembly 12 of the noninvasive system 10 described above for measurement of a sample contained in the sample holder by the noninvasive system 10. In particular, placement of any of the sample holders disclosed in this section on the window assembly 12 allows thermal energy to be delivered to, and infrared energy E to be received from, the material sample S.

As described above, to obtain an infrared absorbance spectrum of a material sample S, the material sample S is typically applied to or contained in a sample holder (also referred to hereafter as a "sample cell" or "cell"). This sample holder or cell holds the sample in an optical path between a radiation source and a radiation detector. It is desired that the material used for the sample holder be highly transmissive in the region of the electromagnetic spectrum which is of interest. In addition, the sample holder should not be soluble in, or reactive with, either the sample or the solvent (if any). A sample holder according to a preferred embodiment of the present invention comprises a microporous sheet disposed between two planar support surfaces or faces which facilitate mounting the sample holder on the noninvasive system 10 or in the whole-blood system 200, both of which are described above. In a modified embodiment, the sample holder further comprises an aperture shield.

A. Structural Properties

Figure 18:
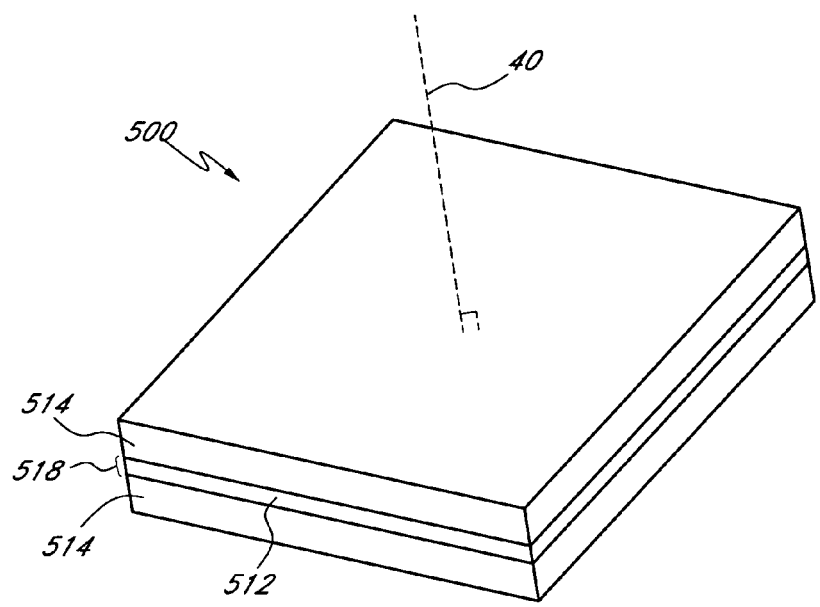
FIG. 18 is a perspective view of a sample holder according to a preferred embodiment of the present invention.

FIG. 18 illustrates a sample holder 500 comprising a microporous sheet 512 disposed between two substantially planar support members 514. Preferably, the microporous sheet 512 is exposed edgewise along its entire periphery, thus forming a transit opening 518 through which a material sample S can be applied to the microporous sheet 512. In other embodiments, the microporous sheet 512 is exposed edgewise along only a portion of its periphery, such as along only one edge of a sample holder 500 having a square, rectangular, triangular or other configuration; or such as along one or more arcuate portions of a sample holder 500 having a circular, elliptical or other configuration having one or more curved edges; or such as intermittently along one or more edges of the sample holder 500. One or more transit openings 518 are thus formed at each such exposed portion. The microporous sheet 512 is configured to hold the material sample S during a spectroscopic analysis. The support members 514 preferably provide the sample holder 500 with a rigid structure, prevent contamination of the material sample S and the spectroscopic equipment, and facilitate the mounting of the sample holder 500 in or on an analyte detection system, including but not limited to a whole-blood system such as the system 200 disclosed herein, or a noninvasive system such as the noninvasive system disclosed herein, or any other suitable whole-blood system or noninvasive system.

As used herein, "microporous sheet" is a broad term and is used in its ordinary sense, and further refers, without limitation, to any non-solid material having a network of voids through which a material sample, for example a bodily fluid, can propagate. As used herein, "transit opening" is a broad term and is used in its ordinary sense, and further refers, without limitation, to any region at which a fluid can enter a microporous sheet. As used herein, "planar support member" is a broad term and is used in its ordinary sense, and further refers, without limitation, to any member having structural rigidity greater than or equal to the structural rigidity of the microporous sheet.

The microporous sheet 512 is preferably thin, typically being less than about 150 $\mu$m thick, and is preferably between about 2.5 $\mu$m and about 25 $\mu$m thick. Thicker films may be used in some instances, but may tend to lead to greater interference due to the stronger spectral absorbances associated with thicker films. Both the microporous sheet 512 and the support members 514 are preferably inert (that is, non-reactive) with respect to any material sample S, such as any of the bodily fluids or other material sample types disclosed herein, to be applied thereto.

The sample holder 500 can have any dimensions sufficient to accommodate a material sample applied thereto and to permit mounting on the analyte detection system in question. For example, in one preferred embodiment, the area of the sample holder is preferably small, ranging from less than 1.0 cm$^2$ to about 6.0 cm$^2$ per each face in many instances. It will be understood by one of ordinary skill in the art that larger or smaller sample holders can be used. The increase in sensitivity of modern instruments enables the taking of spectra of small material samples, and therefore small sizes of sample holders can be used.

In a preferred embodiment, the microporous sheet 512 and the support members 514 comprise polymeric sheets. In such embodiments, the polymeric sheets preferably have a basis weight between about 0.03 g m$^{-2}$ and 1.0 g m$^{-2}$. Polymeric sheets with lower basis weights may be used in some instances, but may tend to be too weak to support the material sample S. Polymeric sheets with higher basis weights may be used in some instances, but may tend to interfere undesirably with material composition analysis.

B. Sample Holder Optical Properties

Selection of appropriate components for the microporous sheet 512 and the support members 514 for a particular application will partially depend on the composition of the material sample and on the analysis to be performed thereon. Polymeric films typically scatter a portion of the light incident thereto. Components of the sample holder can be evaluated for use in particular applications by measuring the aggregate baseline transmittance or absorbance of the sample holder 500. The transmittance T is the ratio of the power of the radiation passed through the sample holder to the power of the radiation incident to the sample holder. Transmittance T is typically expressed as a percentage. Absorbance A is the negative of the log of transmittance. That is, $A=-\log(T)$.

The observed transmittance of the sample holder 500 is a function of overall thickness, porosity of the microporous sheet 512, light scattering characteristics, and composition. Observed transmittance can also partially depend upon the particular wavelength or wavenumber of interest. In a preferred embodiment, the average baseline transmittance of the sample holder 500 in some or all of the wavelength ranges disclosed above for analysis of bodily fluids is greater than about 1%, is preferably greater than about 10%, and is more preferably greater than about 50%. Expressed in terms of absorbance units, the absorbance of the sample holder 500 is less than about 2, is preferably less than about 1, and is more preferably less than about 0. The average baseline absorbance of the sample holder 500 is readily determined by averaging the absorbance of the sample holder 500 at various points within the wavelength range of interest.

The standard deviation (n=20) of the sample holder transmittance variability is a measure of the variation in transmittance of the sample holder at (n=20) different locations on the surface of the sample holder. Sample holder transmittance variability is preferably less than about 25 percent relative, and is more preferably less than about 10 percent relative. To ensure highly probative evaluation of sample holder transmittance variability, it is typically measured at a wavenumber at which the sample holder has an absorbance of about 0.7 to about 1.0 absorbance units. For example, for a sample holder 500 having a polyethylene microporous sheet 512, sample holder transmittance variability is preferably measured at approximately 6.85 μm. When using a dual beam (dispersive) instrument, a small standard deviation in sample holder variability facilitates more accurate subtraction of the absorbances of the sample holder from those of the material sample S. Similarly, with Fourier transform infrared ("FTIR") instruments, a small standard deviation in variability permits subtraction of a standard reference spectrum from those of later analyses.

Although any microporous polymeric film can be used as a microporous sheet 512 in the sample holder 500, the microporous sheet 512 preferably is selected to reduce spectral interference caused by the inherent absorbances of the polymer with the absorbance bands being analyzed in the material sample. Likewise, the support members 514 are also preferably selected to reduce spectral interference caused by the inherent absorbances of the support member 514 with the absorbance bands being analyzed in the material sample. Characteristic absorbances of the microporous sheet 512 and the support members 514 are preferably in regions of the infrared spectrum that do not interfere with the absorbances of the material sample. In other words, the sample holder 500 is preferably highly transmissive in the spectral region or regions of interest. For example, as discussed below, except for the region of about 3.33 μm to about 3.57 μm, where its aliphatic carbon-hydrogen stretching is evident as strong absorbances, sheets of polyethylene can be used in sample holders to perform infrared spectroscopic analysis across the wavelength ranges disclosed above for analysis of bodily fluids. Polyethylene exhibits a limited number of other absorbances in other portions of this range, but these are typically narrow, well-defined absorbances that are easily taken into account. For example, TEFLON™ films and KEL-F™ films (chlorotrifluoroethylene polymers and copolymers) are also useful as constituents of the microporous sheet 512 and the support members 514 for spectroscopic analysis in the wavelength ranges disclosed above for analysis of bodily fluids.

It should be noted that certain spectroscopic instruments have the capacity to "subtract" background absorbances due to solvents, the cell, the atmosphere, and so forth. In a dispersive-type instrument, the infrared beam is split into two parallel beams. One beam is passed through the sample, and the other reference beam is passed through a "blank" cell. When measuring a spectrum of a material sample dissolved in solvent, a cell containing only pure solvent is placed in the reference beam so that the instrument can subtract the spectrum of the solvent from that of the dissolved sample. Additionally, the spectrum of the background of a blank or reference cell can be scanned and electronically stored so that it can be subtracted from sample spectra collected later.

However, the process of subtraction of background absorbances may be imperfect because absorbances may not be cleanly subtracted and may interfere with the absorbances of the material sample, particularly when the sample exhibits subtle absorbances which can be inadvertently masked or lost by the subtraction process. Accordingly, the materials comprising the sample holder 500 are preferably selected to minimize, and more preferably to eliminate, interference due to absorbances of such components with absorbances of the material sample. Because the infrared spectra of many polymer films are well known, it is straightforward to select appropriate materials for the microporous sheet 512 and the support members 514.

In certain embodiments of the sample holder 500, the microporous sheet 512 comprises microporous polyethylene and the support members 514 comprise polyethylene. Polyethylene exhibits a relatively simple spectrum consisting of only four distinctive absorbances in the region of interest: at 3.43 μm, 3.51 μm, 6,83 μm, and 13.9 μm, the latter two being of relatively low intensity. This simple spectrum can be easily subtracted from the spectrum of the material sample S. Polyethylene having a degree of substantial crystallinity has two additional absorbances caused by the splitting of the latter two absorbances into pairs of peaks. Advantageously, polyethylene is inert to many chemicals, is insensitive to moisture, and provides strong, (for example, tear- and puncture-resistant) films at low thicknesses.

In other embodiments, particularly in embodiments wherein the carbon-hydrogen bond (C—H) stretching region is of significant interest, the microporous sheet 512 comprises microporous polytetrafluoroethylene ("PTFE") and the support members 514 comprise polytetrafluoroethylene. PTFE has no absorbances above about 6.67 μm, so the C—H stretching region which is at about 3.33 μm to about 3.57 μm is not subject to interfering absorbances.

C. Microporous Sheet Properties

The void volume of the microporous sheet 512 is typically greater than about 20 percent and is preferably greater than about 50 percent. Many useful microporous polymer films are open structures wherein only a fraction of the total volume is occupied by the polymer material. In sample holders 500 comprising such films, a greater portion of the material in the optical path 40 (see FIG. 18) is the material sample S itself.

When a material sample S is applied to the microporous sheet 512, such as through the transit opening 518 on the edgewise exposed portion(s) of the microporous sheet 512, the material sample will be conducted into and occupy most or all of the microporous sheet 512, thereby containing the material sample in the sample holder 500, and enabling the sample to be analyzed in an appropriate analyte detection system.

By using microporous sheets as provided herein, it is possible to obtain acceptable spectra of material samples that readily crystallize when put on a flat surface for a time. It has previously been considered difficult to obtain spectra of crystalline samples due to the dispersive and reflective effects of the crystal lattice. Applying such a material sample to a microporous sheet retards crystallization and/or limits crystal growth due to the constraint of the pore size. This reduces the previously encountered unwanted dispersive and reflective effects of the crystal lattice, thereby permitting effective spectroscopic analysis.

Microporous polymer sheets can be characterized as having a plurality of interconnecting microscopic pores. Preferably, the pore size distribution across the microporous sheet is substantially uniform so as to provide a low sheet transmittance variability as discussed above. Pore sizes typically range from about 0.1 μm to about 50 μm in their "average characteristic width". For example, in applications wherein the material sample S comprises whole blood, the pore sizes are preferably greater than about 20 μm. Preferably, the support members 514 are not microporous, thereby preventing the material sample S from contacting elements of the analyte detection system to be employed with the holder 500, which could lead to undesirable contamination of both the material sample and the analyte detection system.

As used herein, "average characteristic width" means the average of the largest of the cross-sectional dimension of the pores. For example, if the pores are substantially circular in cross-section, the average characteristic width is the average pore diameter. The pore density is such that the void volume of the microporous sheet 512, as measured by ASTM D4197-82, is typically greater than about 20 percent, is preferably in the range of about 50 percent to about 98 percent, and is more preferably between about 70 percent and about 85 percent. In general, as void volume increases, the inherent absorbances of the microporous sheet 512 are less likely to interfere with the absorbances of the material sample S. The pore configuration is not critical. For instance, the microporous sheet 512 can comprise, for example, a sheet with uniform, substantially circular pores formed by laser ablation or nuclear etching; a sheet made of fibrillated masses with openings of varying size and configuration; a sheet made of non-woven materials; or a sheet made of strands having uniform diameter of material defining a tortuous path (for example, random or fixed) through the sheet. Uniformity of pore size along the transit openings reduces or prevents coagulation of the material sample S at the transit openings, thus enhancing the accuracy of analyte concentration measurements. In addition, uniformity of pore size along the support structures enhances uniform distribution of the material sample S within the microporous sheet. As used herein, "microporous" describes sheets having any such openings.

In a modified embodiment, the porosity of the microporous sheet has a porosity gradient between the edges of the sample holder and the center of the sample holder. For example, if the microporous sheet has a greater porosity in central regions of the sample holder than in the edge regions of the sample holder (that is, near the transit openings), greater capillary forces can be created, thus facilitating the drawing of the material sample into the sample holder.

As used herein, "microporous sheet" also further includes polymeric sheets having at least one structured surface wherein the surface has surface voids, grooves, depressions, and so forth, having a minimum depth of about 0.1 μm and a minimum width of about 0.1 μm therein, and typically having an average characteristic dimension of at least between about 0.1 μm and about 50 μm, sometimes even substantially larger. As described above, in applications wherein the material sample S comprises whole blood, the pore sizes are preferably greater than about 20 μm. As used in this context, "average characteristic dimension" means the average of the largest dimension of the structure element in a plane parallel to the transit opening 518 of the sample holder 500. Such sheets can be formed from solid polymeric sheets by a variety of surface modifying and replication techniques, including but not limited to laser ablation, molding, embossing, extrusion, and the like. Such surface features can increase the sample holder's retention of the material sample, especially material samples containing particulate materials. Structured surface features can also be formed on microporous sheets having a plurality of pores as described above.

Figure 19A:
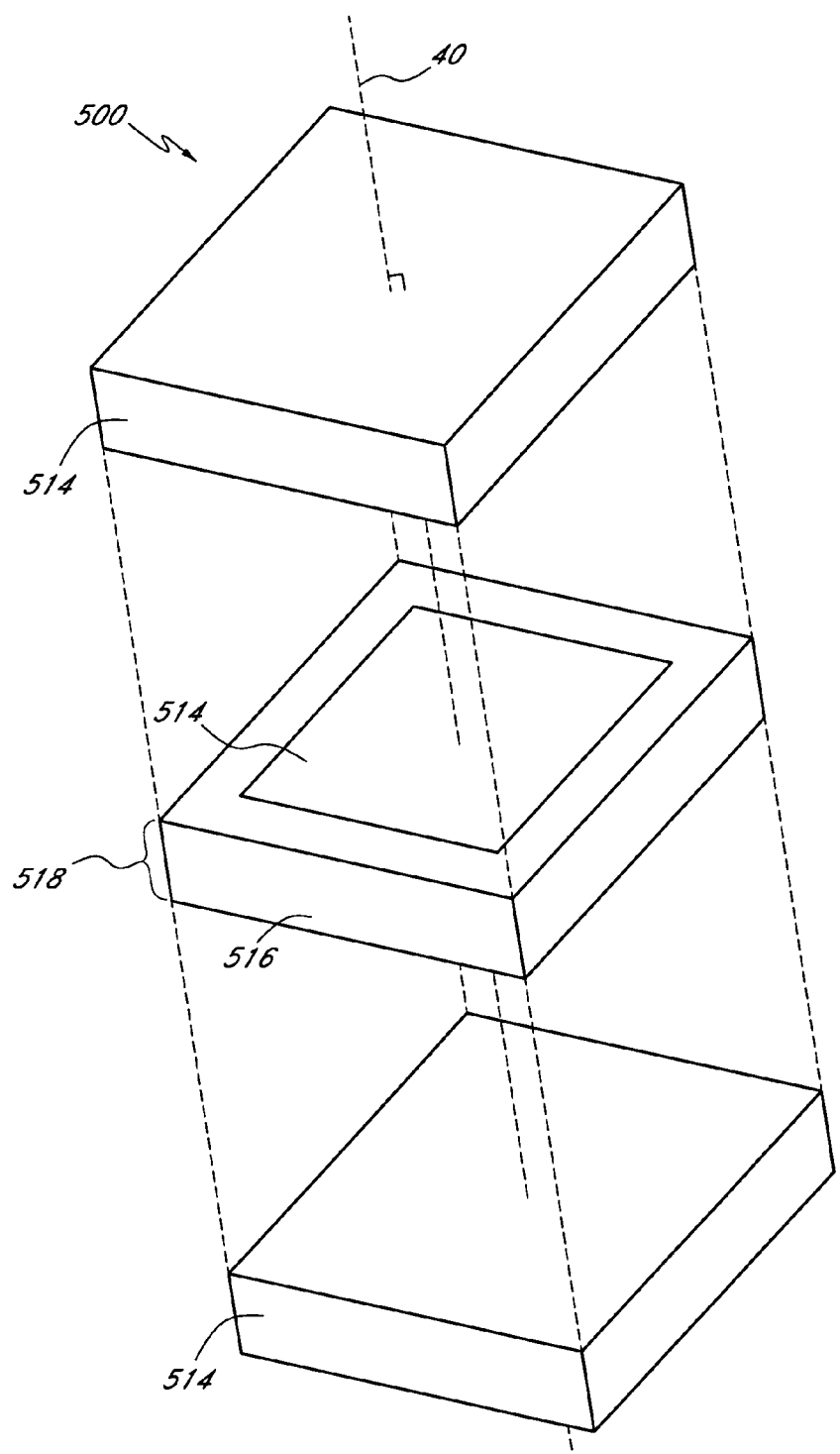
FIG. 19A is an exploded perspective view of a sample holder comprising a circumferential open mesh surrounding the microporous sheet.

FIG. 19A is an exploded perspective view of a sample holder 500 that further comprises a circumferential open mesh 516 bonded to and surrounding the microporous sheet 514. The open mesh 516 facilitates collection and retention of the material sample. In such embodiments, the sample holder 500 preferably meets the transmittance criteria described herein. However, because the open mesh 516 is open, and because the open mesh 516 can be positioned outside of the optical path 40, the bulk properties of the open mesh 516 may or may not meet those transmittance criteria.

U.S. Pat. No. 4,539,256 (Shipman) discloses microporous sheet materials and methods for making the same. Many of these materials can be used with the embodiments disclosed herein. In addition, U.S. Pat. Nos. 3,953,566, 3,962,153, 4,096,227, 4,110,392, 4,187,390 and 4,194,041 describe the preparation of porous articles, including microporous sheets, from polytetrafluoroethylene. All of these patents are hereby incorporated herein by reference. Many of the polymeric materials described in these patents can be used with the embodiments disclosed herein.

Many types of microporous polymer sheets useful in the various embodiments disclosed herein are commercially available in a variety of polymers, thicknesses and void volumes. Among these are: ADVENT™ film (a microporous polyethylene film available from 3M, Saint Paul, Minn.); CELGARD™ films (hydrophobic or hydrophilic microporous polyethylene or polypropylene films available from Hoechst Celanese, Charlotte, N.C.); GORE-TEX™ film (a microporous polytetrafluoroethylene film available from W.L. Gore Associates); ZITEX™ film (a microporous polytetrafluoroethylene film available from Norton Performance Plastics, Wayne, N.J.); and DURAPORE™ film (a microporous hydrophilic film available from Millipore Products Division, Bedford, Mass.). Other illustrative examples include microporous sheets of polyolefins such as ethylene/propylene copolymers, polyvinylidene fluoride, polyester and nylon. In other embodiments, the microporous sheet can consist of one or more of the chosen polymeric films. The microporous sheet can comprise special agents such as the hydrophilic or hydrophobic coatings discussed below.

Figure 19B:
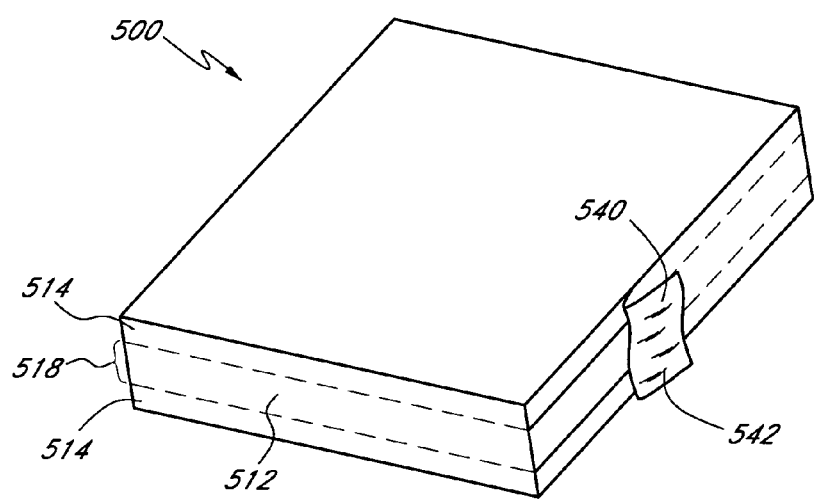
FIG. 19B is a perspective view of a sample holder having a removable protective flap disposed thereon.

In a modified embodiment, illustrated in FIG. 19B, the sample holder 500 further comprises a protective cover or flap 540 that covers at least a portion of the transit opening(s) 518 during storage. Preferably, the flap 540 is secured to the sample holder 500 using a removable adhesive 542, thereby allowing the flap to be moved clear of the transit opening 518 when a material sample S is to be applied thereto. Such a configuration reduces the likelihood of contamination of the microporous sheet 512 when not in use.

D. Support Member Properties

As described above, the support members 514 are configured to provide the sample holder 500 with a rigid structure, to prevent contamination of the material sample S and the analyte detection system, and to facilitate the mounting of the sample holder 500 in or on an analyte detection system. Support members 514 having appropriate optical properties, as described above, can be formed by a wide variety of processes, such as but not limited to, injection molding, stamping of bulk sheet stock, and growth of materials having a crystalline structure.

In a preferred embodiment, the microporous sheet 512 is bonded to the support members 514 using an adhesive (not shown) applied outside the optical path 40. For example, the adhesive can be applied around the circumference of the sample holder 500. Suitable adhesives include, for example, pressure-sensitive adhesives and hot-melt adhesives. Placement of the adhesive outside the optical path reduces the likelihood that the adhesive will interfere with the absorbance spectra obtained during analysis of the material sample S. In certain applications, it may be desirable to configure the adhesive to be repositionable, non-outgassing, or the like. Those of ordinary skill in the art will be able to readily identify and select many suitable adhesives appropriate for a particular application, such as for example press-fitting, heat-activation or tacking characteristics. In other embodiments, different bonding mechanisms can be used, such as for example, lamination, sonic welding or mechanical techniques. In still other embodiments, a thin film of the material comprising the microporous sheet can be applied to the support members 514 using a sputtering process. The layered support members can be constructed in bulk dimensions, and then cut or stamped to appropriate dimensions after the assembly steps have been completed.

The support members 514 are preferably sufficiently stiff, and the microporous sheet 512 is preferably mounted sufficiently tightly therein, that the microporous sheet 512 is held flat across the sample holder 500. Due to the material properties of the microporous sheet 512 discussed above, the microporous sheet 512 is often thin and thus may be subject to creasing or crinkling. It is generally desired that the microporous sheet 512 be maintained substantially flat when mounted on the spectroscopic device, thereby providing a substantially constant microporous sheet thickness along the optical path 40. A substantially constant microporous sheet thickness causes the infrared energy E to pass through a substantially constant amount of material sample S, and minimizes reflectance and scattering of the infrared energy by the microporous sheet. Reflectance and scattering are generally undesirable effects that can cause interference in spectra obtained using the sample holder. As discussed above, the support members 514 can comprise any suitable film that is relatively rigid compared to the microporous sheet 512 and that is preferably not microporous, such as polymeric films.

In some applications it may be desirable for the prepared material sample to be archived or stored for future reference. Accordingly, in such embodiments, it is preferable that support members 514 comprise a material that may be written on or otherwise labeled (preferably near the edges) so that pertinent information relating to the material sample (for example, index number or date/time information) can be noted thereon. In other embodiments, a label or other additional information-bearing media (such as microfilm, magnetic media, or the like) can be included around the perimeter of the support members 514 if desired.

E. Aperture Shield

Figure 20A:
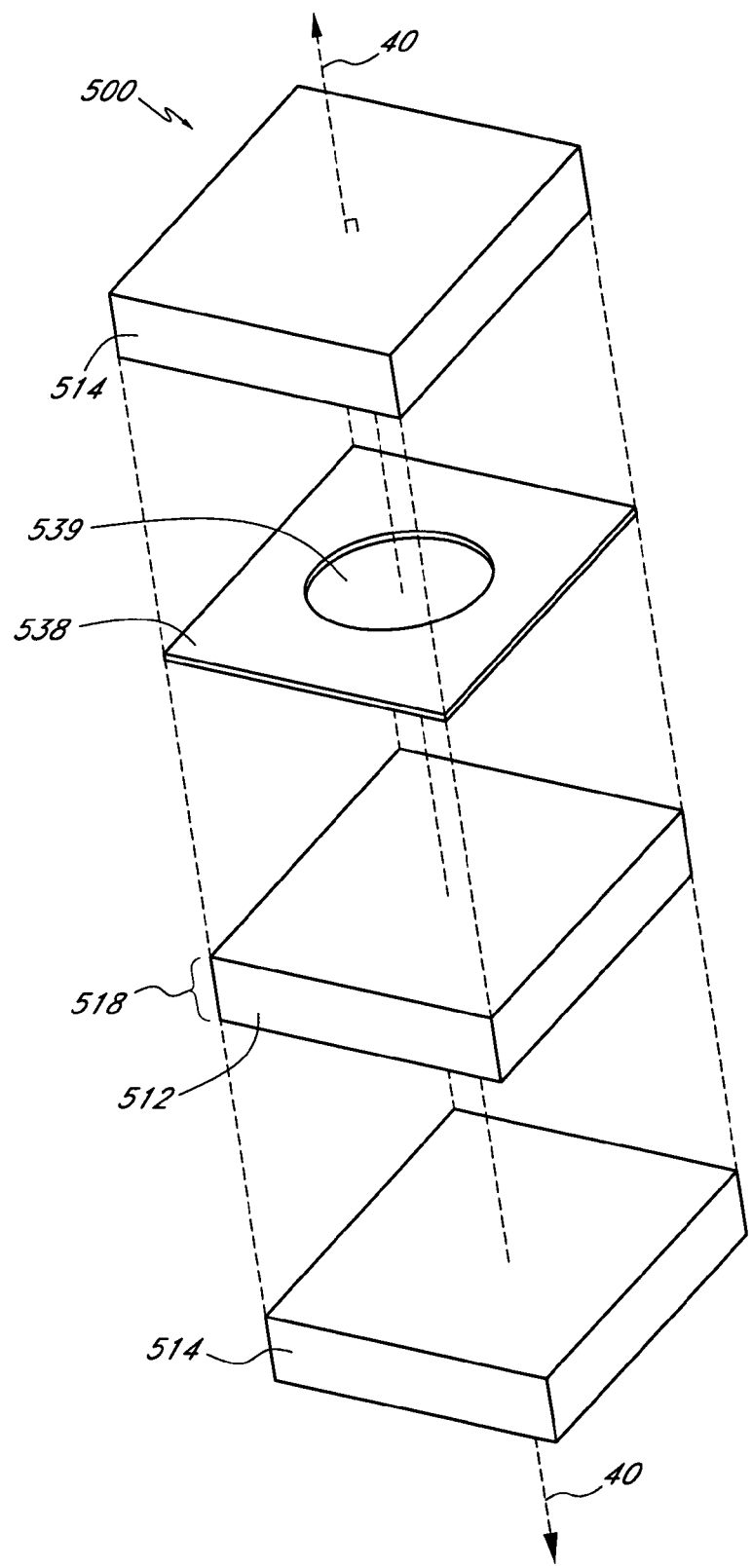
FIG. 20A is an exploded perspective view of a sample holder comprising a shield that forms an aperture.
Figure 20B:
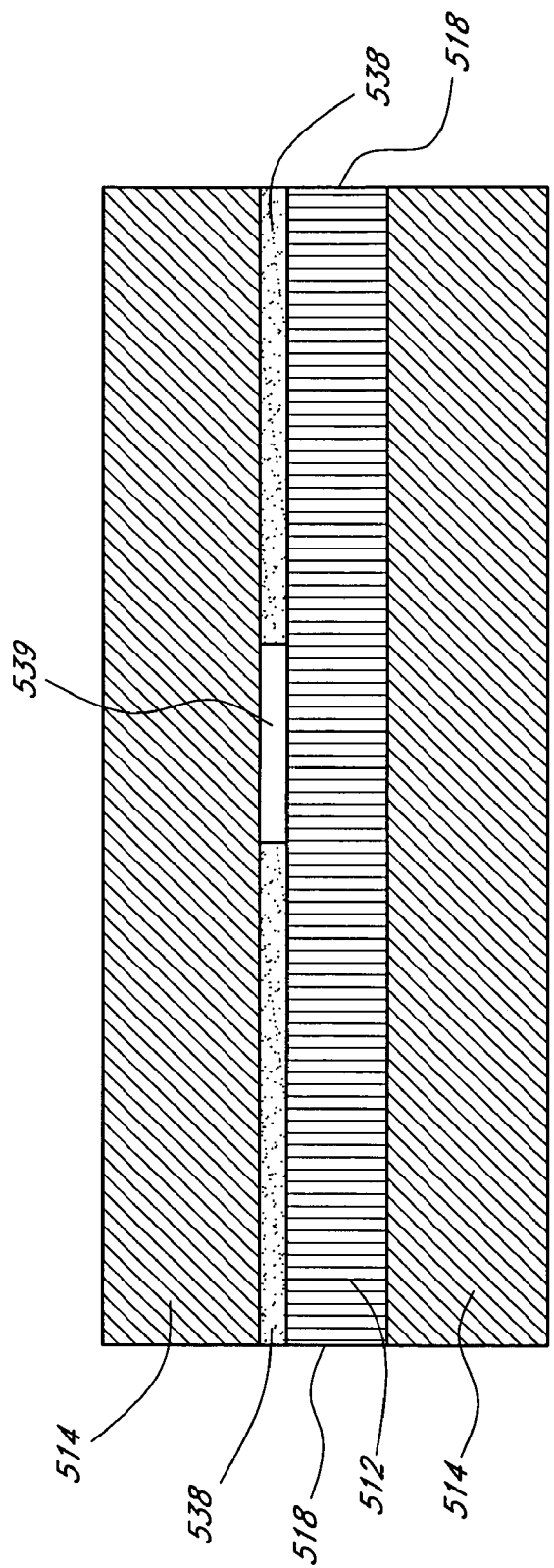
FIG. 20B is a cross-sectional view of the sample holder of FIG. 20A.

In certain applications, it is desired to restrict the area of the microporous membrane through which the emitted radiation passes. FIG. 20A illustrates an embodiment wherein sample holder 500 comprises a microporous sheet 512 and support members 514. The sample holder 500 further comprises a shield 538 which covers a portion of the microporous sheet 512, thereby forming an aperture 539 that leaves only a portion of microporous sheet 512 exposed. In use, the optical path 40 passes through the aperture 539 and the portion of the material sample located in the aperture 539. Shield 538 is preferably substantially opaque to the wavelengths of radiation to be used (other than, of course, the aperture 539), such that no interfering absorbances are produced and no incident radiation is scattered. In the wavelength ranges disclosed above for analysis of bodily fluids, the shield 539 preferably has a transmittance of less than about 10 percent, and more preferably of less than about 1 percent. FIG. 20B is a cross-sectional view of the sample holder 500 of FIG. 20A. The shield 538 can cover a portion of only one side of microporous sheet 512 as shown in FIGS. 20A and 20B, or it can cover portions of both sides of microporous sheet 512, leaving at least one aperture 539, configured to permit the wavelength(s) of interest to pass through the entire sample holder 500.

In certain embodiments, the shield 538 serves as a target to facilitate arrangement of the material sample S on the microporous sheet 512 for spectroscopic analysis. In other embodiments, the shape, size, and location of the aperture 539 are dependent at least in part upon the characteristics of the analyte detection system being used, particularly on the geometric arrangement of the window assembly (as discussed above). For example, in such embodiments, the presence of the material sample across the entire aperture 539 can serve as a indication that a sufficient amount of material sample has been applied to the sample holder 500. Also, depending on the configuration of the support members 514 and the shield 538, the shield 538 can serve to impart greater support stiffness to microporous sheet 532.

The shield 538 can comprise plastic, paperboard, metal, or any other suitable, rigid material with appropriate optical properties. Preferably, the shield 538 is inert and nonabsorbent, so that if the material sample S contacts the shield, waste is minimized. The shield 538 can be secured to the microporous sheet 512 and the support members 514 by any suitable technique, such as for example, adhesives, sonic welding and mechanical closures.

One of ordinary skill in the art will understand that the shapes of the support members 514, and the aperture 539 if used, can be of many different types, depending in part on such things as the construction of the sample holder 500, the characteristics and specifications of the equipment with which the sample holder 500 will be used, the type of material sample being analyzed, and the preferences of individuals using the sample holder 500. The same is of course true of the microporous sheet 512.

F. Skin-Piercing Structure

Figure 21A:
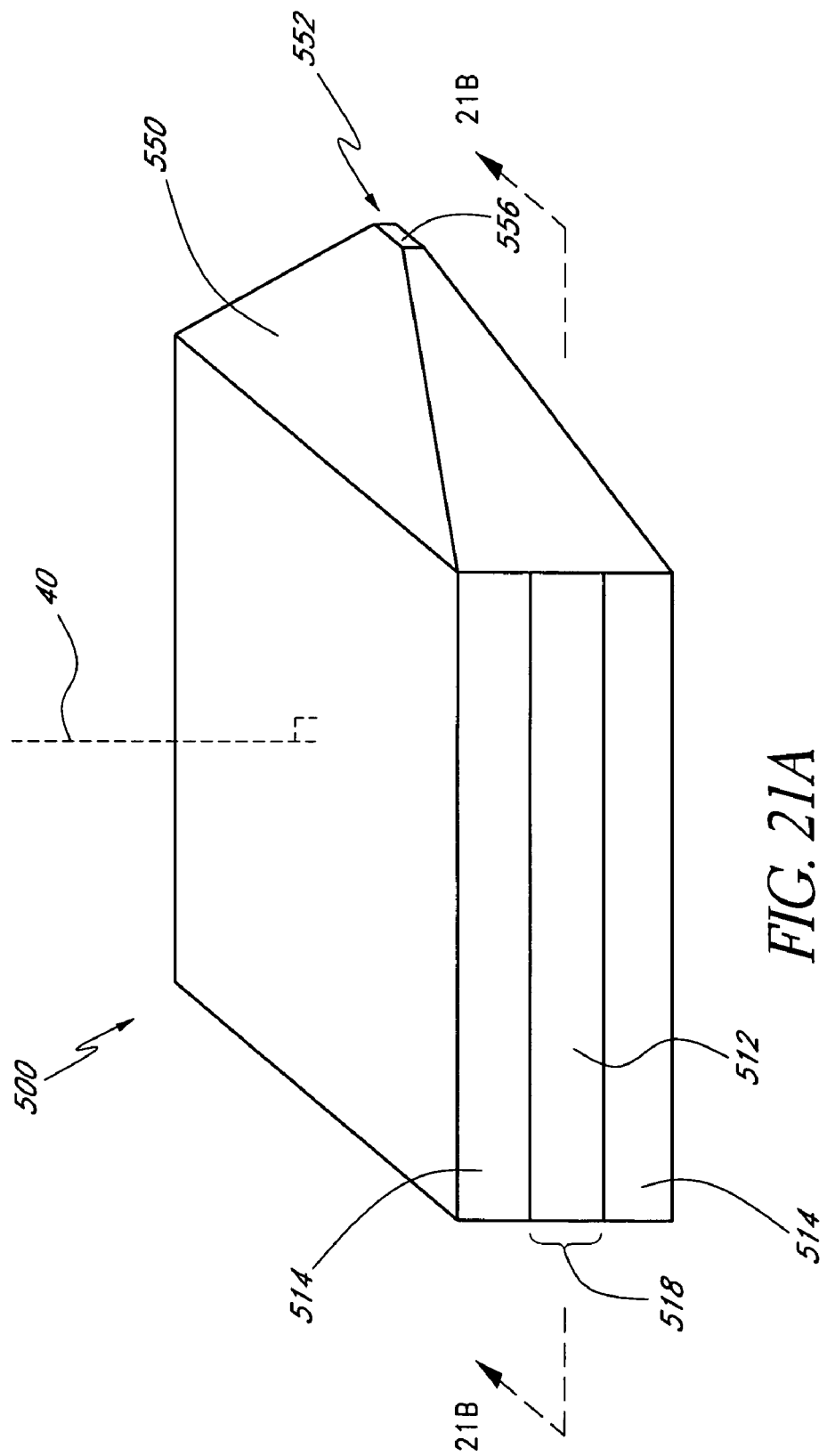
FIG. 21A is a perspective view of a sample holding having a skin-piercing structure.
Figure 21B:
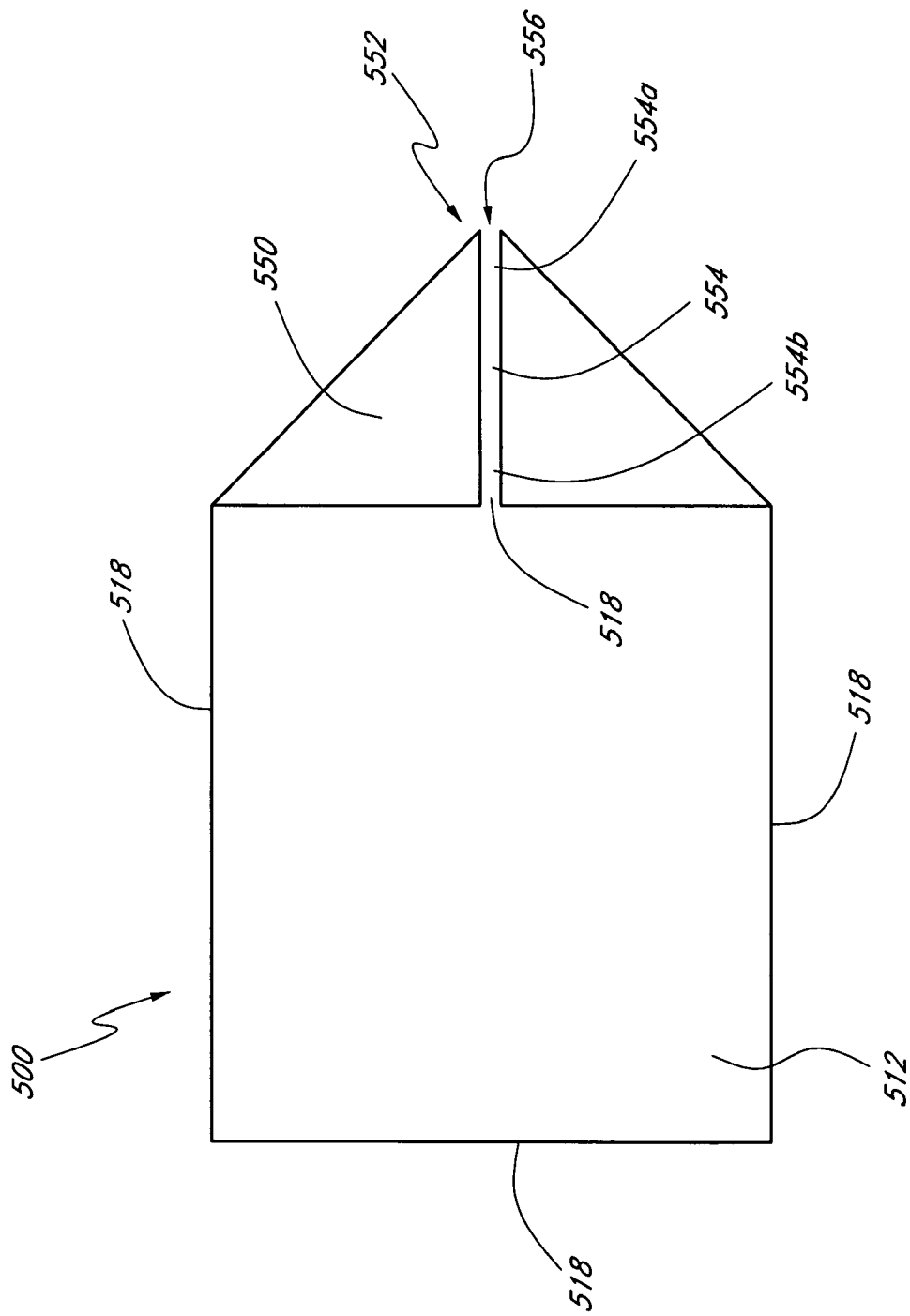
FIG. 21B is a cross-sectional view of the sample holding of FIG. 21A taken along line 21B—21B.

In a modified embodiment, the sample holder further comprises a skin-piercing structure configured to facilitate introduction of a bodily fluid into the microporous sheet. As illustrated in FIGS. 21A and 21B, such a skin-piercing structure comprises one or more tapered prongs 550 mounted on one side of a sample holder 500. The tapered prongs can be securely attached to the edge of the sample holder 500 with any suitable fixation technique, such as with adhesives or snap fittings. Each of the tapered prongs 550 preferably has a sharpened distal tip 552 capable of easily piercing human skin. In one embodiment, the tapered prongs 550 comprise a polished metal, such as stainless steel or aluminum. Although the sample holder 500 illustrated in FIGS. 21A and 21B has one tapered prong 550, one of ordinary skill in the art will recognize that equivalent structures have a plurality of tapered prongs on one or multiple sides of the sample holder. In addition, distal tips having other shapes, such as conical or tubular shapes, are also equivalent.

For example, in one preferred embodiment, the outer diameter of a tapered prong 550 is generally between about 100 $\mu$m and 400 $\mu$m at its thickest point, and generally less than about 10 $\mu$m at the distal tip 552. The average outer diameter of a tapered prong 550 is generally between about 100 $\mu$m and 300 $\mu$m, typically between about 120 $\mu$m and 200 $\mu$m. The length of a tapered prong 550 will depend on the desired depth of insertion. More particularly, a tapered prong 550 will be appropriately dimensioned within certain ranges depending on the type of biological fluid (for example, interstitial fluid, blood or both) desired for sampling and the thickness of the skin layers of the particular patient being tested. As such, target skin layers into which a tapered prong can be inserted include, but are not limited to, the dermis, epidermis and the stratum corneum (that is, the outermost layer of the epidermis). Preferably, a tapered prong 550 has a length of at least about 50 $\mu$m and more preferably at least about 100 $\mu$m, where the length may be as great as 500 $\mu$m or greater, but typically does not exceed about 2000 $\mu$m and usually does not exceed about 3000 $\mu$m.

Still referring to FIGS. 21A and 21B, the tapered prongs 550 preferably further comprise a passageway 554 that is open at a distal tip window 556. The passageway 554 is preferably in contact with one of the transit openings 518 of the sample holder, and is preferably filled with a microporous material. While the passageway 554 illustrated in FIGS. 21A and 21B is substantially linear, one of ordinary skill in the art will recognize that in equivalent structures the passageway can have any shape or orientation, provided that the passageway contacts at least a portion of one of the transit openings. In modified embodiments, the passageway 554 is filled with a microporous material having a gradient of porosity between a distal passageway region 554a and a proximal passageway region 554b. In such embodiments, the microporous material is preferably more porous at the proximal passageway region 554b than at the distal passageway region 554a, thereby providing greater rigidity at the distal tip 552 for piercing the skin. The change in porosity between the proximal passageway region 554b and the distal passageway region 554a can be gradual or sharp.

The micro-protrusions or the distal tip 552 are preferably configured to be mechanically stable and strong enough to penetrate the stratum corneum without breaking. For example, in one embodiment, such skin-piercing structures comprise a biocompatible material so as not to cause irritation to the skin or an undesirable tissue response. Although certain embodiments of the sample holder may be disposable, for those that are intended to be reusable, it is preferable that the material of the micro-needles is able to withstand sterilization cycles.

In other embodiments, the skin-piercing function is accomplished by the surface of the distal tip window. Specifically, the distal tip window is formed with sharp protrusions, such as for example micro-needles. In such embodiments, this surface of the distal tip window is nonporous, wherein the sharp protrusions have a porous central core that extends through the distal tip window, thereby defining a fluid access opening to access a fluid to be analyzed. The fluid transfer medium preferably extends between the access opening of the micro-piercing member to the passageway, and functions to transfer fluid to the microporous sheet.

The fluid transfer medium is preferably made of a porous hydrophilic material. The material preferably is not water-absorbent, thus preventing water within a biological fluid from being absorbed by the fluid transfer material, but instead causing such water to be completely passed through the medium along with the other components of the biological fluid. Porous hydrophilic materials usable as the fluid transfer medium include, but are not limited to, polymers, ceramics, glass and silica. Suitable polymers include polyacrylates, epoxies, polyesters, polycarbonate, polyamideimide, polyaryletherketone, polyetheretherketone, polyphenylene oxide, polyphenylene sulfide, liquid crystalline polyesters, or their composites. Examples of ceramics are aluminum oxide, silicon carbide and zirconium oxide.

A hydrophilic gel or the like may also be used in conjunction with the porous material located within the passageway. Suitable gels include natural gels such as agarose, gelatin, mucopolysaccharide, starch and the like, and synthetic gels such as anyone of the neutral water-soluble polymers or polyelectrolytes, such as polyvinyl pyrrolidone, polyethylene glycol, polyacrylic acid, polyvinyl alcohol, polyacrylamide, and copolymers thereof.

In embodiments comprising a skin-piercing structure, when the distal tip 552 is pierced through a patient's skin, a body fluid of the patient (for example, blood) will be drawn through the passageway 554 and into the microporous sheet 512. For example, in embodiments wherein the passageway comprises a hydrophilic porous material, the pores can provide a capillary action by which fluid can be transferred. This configuration provides a convenient sample holder 500 that can be used in both the collection and analysis of a patient's bodily fluids.

G. Use and Analysis Considerations

As mentioned above, the sample holders described herein can be easily used with the analyte detection systems described above, simplify the process of preparing material samples for analysis, and facilitate precise and accurate measurements.

Hydrophilic films are useful as sheets in spectroscopic analysis of aqueous samples. Such samples can be applied directly to a hydrophilic film without pre-wetting. In addition to aqueous samples, hydrophilic films are useful in the analysis of biological fluids such as blood, sweat, tears, urine, semen, and other bodily fluids disclosed herein. Such biological fluid samples can be applied directly to the sample holder without the need for lengthy sample preparation, and clear, distinct measurements can be obtained. Microporous sheets comprising materials that are inherently hydrophilic or that are treated (for example, by coating with suitable material or by applying suitable surface treatment) to render them hydrophilic can be used with the various embodiments of the sample holders described herein.

In certain embodiments, the microporous sheet is treated to improve sample collection and retention properties. The microporous sheet can be treated before or during fabrication of the sample holder, or before application of the material sample. The timing of the treatment of the microporous sheet depends in part on the material comprising the microporous sheet, the treatment, and intended material sample to be analyzed.

For example, in certain embodiments the microporous sheet is exposed to corona treatment to impart an electrostatic charge thereto. Typically, when electrostatically-charged, the microporous sheet has a substantially uniform charge across the surfaces that contact the support members, with a side-to-side potential of at least about 100 V per 0.75 mil thickness. Electrostatic charges can be particularly useful in the collection and retention of greater quantities of fine particulate materials. By increasing retention of sample material in the microporous sheet, the amount of equipment cleaning and maintenance is likewise reduced.

In another embodiment, at least a portion of the surface of the microporous sheet is treated by application of a material, such as by coating or graft polymerization, that will modify the interaction of the microporous sheet with the material sample. For example, azlactone materials can be used to concentrate proteins in solution in a sample holder for infrared spectroscopic analysis.

The sample holders described herein, while providing good analytical results, are sufficiently inexpensive to be discarded after use. Thus, the need to clean and polish the sample holders for reuse is avoided. Furthermore, the sample holders described herein provide reduced exposure to hazardous samples as well as reduced exposure to potentially harmful solvents such as are used in cleaning and reconditioning conventional sample holders, examples of which include chloroform, methylene chloride, and toluene. Additionally, as described above, the sample holder can be stored or archived for future reference, if desired. For instance, it is sometimes desired to compare the spectra of a material sample with the spectra of one or more known standard samples, and in some instances it is desired to compare various spectra during the course of a chemical reaction or process. The sample holders described herein can be stored with samples present in the microporous sheet, thus permitting such samples to be analyzed at a later date, often with little or no degradation in the spectra. In particular, due to the microporous structure of the sheet, the material sample typically penetrates the pores in the sheet and is securely held within the sheet. Thus, there is typically little tendency to lose material sample from the exposed surfaces of the microporous sheet, and due to the chemical inertness of the microporous sheet, there is little tendency of the material sample to react with the microporous sheet. Accordingly, the sample holders described herein are also well-suited for use in aging and degradation studies of materials.

The sample holders described herein can be used to provide a convenient method of performing spectroscopic analysis. For example, one preferred method for spectroscopic analysis provided herein comprises
 a) providing a sample holder as described herein;
 b) applying the material sample to the microporous sheet exposed at the transit opening;
 c) transmitting radiation in desired wavelength(s) through the material sample by projecting such radiation on one face of the sample holder; and
 d) analyzing the radiation transmitted through or emitted from the material sample and sheet in a spectral region of interest.

In one preferred embodiment, a roll of microporous sheet material is fed into a spectroscopic analysis device and secured in position by clamping support member plates on either side of the microporous sheet. In such embodiments, the support member plates engage releasably with the microporous sheet.

Given the filling factor and porosity of a polyethylene microporous sheet, it is possible to determine the pathlength and the fraction of radiation scattered by using the known polyethylene peaks as a reference. The height of the absorption peaks will allow the thickness of the polyethylene film to be accurately determined. This technique is often used in thin film technology, where the film thickness is determined by absorption lines in the coatings. It is also possible to spike the polyethylene with a known concentration of an internal standard. One of these standards is potassium potassiumthiocyanate (KSCN). Thus, given the filling factor of the microporous sheet is known, the peaks of the spike will allow the pathlength to be determined in a wet measurement, thus eliminating any need for the dry or blank measurement. The spike wavelengths are preferably outside the water total absorbing bands.

In embodiments where a dry measurement is performed, similar principles apply because the microporous material will behave as a scatterer. In particular, the microporous sheet will remove the radiation coherence between the two support members and will provide a more precise measurement of the actual beam intensity in the material sample. Highly scattering material will generally overestimate the absorbance if scattering is not accounted for.

As will be appreciated by those of ordinary skill in the art, conventional reagent-based analyte detection systems react an amount of analyte (for example, glucose) with a volume of body fluid (for example, blood) with a reagent (for example, the enzyme glucose oxidase) and measure a current (that is, electron flow) produced by the reaction. Generating a current large enough to overcome noise in the electronic measurement circuitry requires a substantial amount of the analyte under consideration and thus establishes a minimum volume that can be measured. The present state of the art systems require about 0.5 $\mu$L of blood represent the lower volume limit of electronic measurement technology.

Spectroscopic measurement not requiring a reagent, as taught herein, relies on (1) absorption of electromagnetic energy by analyte molecules in the sample and (2) the ability of the measurement system to measure the absorption by these molecules. The volume of the sample required for measurement is substantially determined by the physical size of the optical components, and is significantly less than the sample volume required using conventional reagent based systems. Specifically, the dimensions of the analyte detection systems disclosed herein can result in a sample volume as low as about 0.3 µL. The presence of the microporous sheet can further reduce the sample volume because the volume of material sample required to fill the microporous sheet is less than the volume of material sample required to fill and empty (that is, non-microporous) cuvette.

The examples expounded herein are merely illustrative of the utility of the sample holders described herein, demonstrating that spectra of a wide variety of samples can be obtained using microporous sheets as described herein, and using a wide variety of sample collection and application techniques. One of ordinary skill in the art will appreciate that the apparatuses and the analysis methodologies described herein can incorporate, without being limited by, well known techniques for sample element use and construction, such as some of those set forth in U.S. Pat. No. 5,470,757 and PCT Publication WO 93/00580, the entire contents of both of which are hereby incorporated herein by reference. Various modifications and alternations of the present invention will be apparent to those of ordinary skill in the art without departing from the scope of the present invention, which is defined by the claims that follow.

We claim:

1. A spectroscopic sample holder comprising:
   a microporous sheet having a top surface, a bottom surface substantially parallel to the top surface, and at least one side surface oriented substantially perpendicular to the top and bottom surfaces, the side surface forming an exposed transit opening configured to contact a material sample and distribute the contacted material sample into the microporous sheet,
   a first planar support member positioned on, and substantially parallel to, the top surface of the microporous sheet;
   a skin-piercing structure having a passageway that connects a distal portion of the skin-piercing structure with the exposed transit opening; and
   a second planar support member positioned on the bottom surface of the microporous sheet, and oriented substantially parallel to the first planar support member.

2. The spectroscopic sample holder of claim 1, wherein the exposed transit opening comprises an entry region through which the material sample can enter the microporous sheet.

3. The spectroscopic sample holder of claim 1, wherein the first and second planar support members comprise members having a structural rigidity greater than or equal to a structural rigidity of the microporous sheet.

4. The spectroscopic sample holder of claim 1, wherein the microporous sheet further comprises a non-solid material having a network of voids through which the material sample can propagate.

5. The spectroscopic sample holder of claim 1, wherein information bearing media is disposed on at least one of the planar support members.

6. The spectroscopic sample holder of claim 1, further comprising a shield forming an aperture.

7. The spectroscopic sample holder of claim 6, wherein the shield is substantially opaque to electromagnetic radiation.

8. The spectroscopic sample holder of claim 1, wherein the microporous sheet has four side surfaces, and the first and second planar support members are substantially coextensive with at least two of the side surfaces of the microporous sheet.

9. The spectroscopic sample holder of claim 8, wherein the first and second planar support members are substantially coextensive with all four of the side surfaces of the microporous sheet.

10. The spectroscopic sample holder of claim 1, further comprising an open mesh at least partially covering the exposed transit opening.

11. The spectroscopic sample holder of claim 1, wherein the spectroscopic sample holder has an average baseline transmittance of at least 1 percent.

12. The spectroscopic sample holder of claim 1, wherein the spectroscopic sample holder has an average baseline transmittance of at least 10 percent.

13. The spectroscopic sample holder of claim 1, wherein the spectroscopic sample holder has an average baseline transmittance of at least 50 percent.

14. The spectroscopic sample holder of claim 1, wherein the microporous sheet consists essentially of a polyolefin film.

15. The spectroscopic sample holder of claim 1, wherein the microporous sheet consists essentially of one or more of the following: polyethylene, polypropylene, ethylene/propylene copolymers, polytetrafluoroethylene, chlorotrifluoroethylene polymers and copolymers, polyvinylidene fluoride, polyester, or nylon.

16. The spectroscopic sample holder of claim 1, wherein the microporous sheet is hydrophilic.

17. The spectroscopic sample holder of claim 1, wherein the microporous sheet is hydrophobic.

18. The spectroscopic sample holder of claim 1, wherein the microporous sheet has an electrostatic charge on opposing sides.

19. The spectroscopic sample holder of claim 1, wherein the microporous sheet further comprises azlactone material.

20. The spectroscopic sample holder of claim 19, wherein a polymer material is grafted to the azlactone material.

21. The spectroscopic sample holder of claim 1, wherein the microporous sheet comprises a polymeric, non-woven material.

22. The spectroscopic sample holder of claim 1, wherein the microporous sheet has a void volume greater than about 20 percent.

23. The spectroscopic sample holder of claim 1, wherein the microporous sheet has a void volume of between about 50 percent and about 98 percent.

24. The spectroscopic sample holder of claim 1, wherein the microporous sheet has a void volume of between about 70 percent and about 85 percent.

25. The spectroscopic sample holder of claim 1, wherein the microporous sheet has pores ranging from about 0.1 µm to about 50 µm in their average characteristic width.

26. The spectroscopic sample holder of claim 1, wherein the exposed transit opening has a structured surface.

27. The spectroscopic sample holder of claim 1, wherein the microporous sheet has a thickness between about 2.5 µm and about 25 µm.

28. The spectroscopic sample holder of claim 1, wherein the microporous sheet transmittance variability is less than 25 percent.

29. The spectroscopic sample holder of claim 1, wherein the microporous sheet transmittance variability is less than 10 percent.

30. The spectroscopic sample holder of claim 1, wherein the microporous sheet has an area between about 1 cm² and about 6 cm².

31. An apparatus comprising:
a microporous sheet positioned between first and second support members, wherein at least a portion of the microporous sheet is an exposed transit opening configured to receive and distribute a material sample into the microporous sheet; and
a skin-piercing structure having a passageway that connects a distal portion of the skin-piercing structure with the exposed transit opening.

32. The apparatus of claim 31, wherein the exposed transit opening comprises art entry region through which the material sample can enter the microporous sheet.

33. The apparatus of claim 31, wherein the first and second planar support members comprise members having a structural rigidity greater than or equal to a structural rigidity of the microporous sheet.

34. The apparatus of claim 31, wherein the microporous sheet comprises a non-solid material having a network of voids through which the material sample can propagate.

35. The apparatus of claim 31, wherein information bearing media is disposed on at least one of the support members.

36. The apparatus of claim 31, further comprising a shield forming an aperture.

37. The apparatus of claim 36, wherein the shield is substantially opaque to electromagnetic radiation.

38. The apparatus of claim 31, wherein the microporous sheet has four side surfaces, and the first and second support members are substantially coextensive with at least two of the side surfaces of the microporous sheet.

39. The apparatus of claim 38, wherein the first and second support members are substantially coextensive with all four of the side surfaces of the microporous sheet.

40. The apparatus of claim 31, further comprising an open mesh at least partially covering the exposed transit opening.

41. The apparatus of claim 31, wherein the exposed transit opening has a structured surface.

42. The apparatus of claim 31, wherein the apparatus has an average baseline transmittance of at least 1 percent.

43. The apparatus of claim 31, wherein the apparatus has an average baseline transmittance of at least 10 percent.

44. The apparatus of claim 31, wherein the apparatus has an average baseline transmittance of at least 50 percent.

45. The apparatus of claim 31, wherein the microporous sheet consists essentially of a polyolefin film.

46. The apparatus of claim 31, wherein the microporous sheet consists essentially of one or more of the following: polyethylene, polypropylene, ethylene/propylene copolymers, polytetrafluoroethylene, chlorotrifluoroethylene polymers and copolymers, polyvinylidene fluoride, polyester, or nylon.

47. The apparatus of claim 31, wherein the microporous sheet is hydrophilic.

48. The apparatus of claim 31, wherein the microporous sheet is hydrophobic.

49. The apparatus of claim 31, wherein the microporous sheet has an electrostatic charge on opposing sides.

50. The apparatus of claim 31, wherein the microporous sheet further comprises azlactone material.

51. The apparatus of claim 50, wherein a polymer material is grafted to the azlactone material.

52. The apparatus of claim 31, wherein the microporous sheet comprises a polymeric, non-woven material.

53. The apparatus of claim 31, wherein the microporous sheet has a void volume greater than about 20 percent.

54. The apparatus of claim 31, wherein the microporous sheet has a void volume between about 50 percent and about 98 percent.

55. The apparatus of claim 31, wherein the microporous sheet has a void volume between about 70 percent and about 85 percent.

56. The apparatus of claim 31, wherein the microporous sheet has pores ranging from about 0.1 $\mu$m to about 50 $\mu$m in their average characteristic width.

57. The apparatus of claim 31, wherein the microporous sheet has a thickness between about 2.5 $\mu$m and about 25 $\mu$m.

58. The apparatus of claim 31, wherein the microporous sheet transmittance variability is less than 25 percent.

59. The apparatus of claim 31, wherein the microporous sheet transmittance variability is less than 10 percent.

60. The apparatus of claim 31, wherein the microporous sheet has an area between about 1 cm² and about 6 cm².

61. A method comprising:
providing a microporous sheet disposed between first and second support members, such that at least a portion of the microporous sheet is left exposed;
contacting the exposed portion of the microporous sheet with a material sample such that at least a portion of the material sample is drawn into the microporous sheet;
transmitting electromagnetic radiation through the material sample in the microporous sheet;
piercing a patient's skin with a skin-piercing structure, the skin-piercing structure having a passageway that connects a distal portion of the skin-piercing structure with the exposed portion of the microporous sheet; and
analyzing the electromagnetic radiation transmitted through the material sample in a spectral region of interest.

62. The method of claim 61, wherein the exposed portion of the microporous sheet comprises an entry region through which the material sample can enter the microporous sheet.

63. The method of claim 61, wherein the first and second planar support members comprise members having a structural rigidity greater than or equal to a structural rigidity of the microporous sheet.

64. The method of claim 61, wherein the microporous sheet comprises a non-solid material having a network of voids through which the material sample can propagate.

65. The method of claim 61, wherein the material sample is allowed to dry before electromagnetic radiation is transmitted through the microporous sheet.

66. The method of claim 61, further comprising determining the baseline transmittance of the microporous sheet before contacting the material sample to the microporous sheet.

67. The method of claim 61, wherein the material sample is a solvent soluble material, and further comprising dissolving the sample in solvent before contacting the material sample to the microporous sheet.

68. The method of claim 61, wherein information bearing media is disposed on at least one of the support members.

69. The method of claim 61, wherein the microporous sheet further comprises a shield forming an aperture.

70. The method of claim 69, wherein the shield is substantially opaque to electromagnetic radiation.

71. The method of claim 61, wherein the microporous sheet has four side surfaces, and the first and second support members are substantially coextensive with at least two of the side surfaces of the microporous sheet.

72. The method of claim 71, wherein the first and second support members are substantially coextensive with all four of the side surfaces of the microporous sheet.

73. The method of claim 61, further comprising an open mesh at least partially covering the exposed portion of the microporous sheet.

74. The method of claim 61, wherein the exposed portion of the microporous sheet has a structured surface.

75. The method of claim 61, wherein the microporous sheet has an average baseline transmittance of at least 1 percent.

76. The method of claim 61, wherein the microporous sheet has an average baseline transmittance of at least 10 percent.

77. The method of claim 61, wherein the microporous sheet has an average baseline transmittance of at least 50 percent.

78. The method of claim 61, wherein the microporous sheet consists essentially of a polyolefin film.

79. The method of claim 61, wherein the microporous sheet consists essentially of one or more of the following: polyethylene, polypropylene, ethylene/propylene copolymers, polytetrafluoroethylene, chlorotrifluoroethylene polymers and copolymers, polyvinylidene fluoride, polyester, or nylon.

80. The method of claim 61, wherein the microporous sheet is hydrophilic.

81. The method of claim 61, wherein the microporous sheet is hydrophobic.

82. The method of claim 61, wherein the microporous sheet has an electrostatic charge on opposing sides.

83. The method of claim 61, wherein the microporous sheet further comprises azlactone material.

84. The method of claim 83, wherein a polymer material is grafted to the azlactone material.

85. The method of claim 61, wherein the microporous sheet comprises a polymeric, non-woven material.

86. The method of claim 61, wherein the microporous sheet has a void volume greater than about 20 percent.

87. The method of claim 61, wherein the microporous sheet has a void volume between about 50 percent and about 98 percent.

88. The method of claim 61, wherein the microporous sheet has a void volume between about 70 percent and about 85 percent.

89. The method of claim 61, wherein the microporous sheet has pores ranging from about 0.1 $\mu$m to about 50 $\mu$m in their average characteristic width.

90. The method of claim 61, wherein the microporous sheet has a thickness between about 2.5 $\mu$m and about 25 $\mu$m.

91. The method of claim 61, wherein the microporous sheet transmittance variability is less than 25 percent.

92. The method of claim 61, wherein the microporous sheet transmittance variability is less than 10 percent.

93. The method of claim 61, wherein the microporous sheet has an area between about 1 cm$^2$ and about 6 cm$^2$.

94. An analyte detection system for determining the concentration of analyte in a biological fluid sample drawn from a patient, the system comprising:
　a near patient optical detection system comprising:
　　a source configured to emit electromagnetic radiation; and
　　a detector positioned in an optical path of the radiation;
　a sample element configured for removable engagement with the optical detection system, the sample element comprising:
　　a sample cell configured to hold the biological fluid sample, the sample cell being located in the optical path upon engagement of the sample cell with the optical detection system, the sample cell being defined by at least one window which is highly transmissive of infrared radiation; and
　　a sample supply passage extending from and in fluid communication with the sample cell and including a pierceable portion; and
　a sample extractor comprising a skin piercing member, the skin piercing member configured to create a passageway that connects a distal portion of the skin-piercing structure with the pierceable portion of the sample supply passage of the sample element;
　wherein the detection system performs optical analysis on the material sample to assess the concentration of at least one constituent of the material sample.

95. The system of claim 94, further comprising a filter positioned in the sample supply passage, the filter configured to filter the material sample passing therethrough.

96. The system of claim 94, further comprising a microporous sheet situated in the optical path of the radiation, wherein the microporous sheet is positioned within the sample cell.

97. The system of claim 96, wherein the microporous sheet comprises a non-solid material having a network of voids through which the material sample can propagate.

98. A method comprising:
　providing a microporous sheet disposed between first and second support members, such that at least a portion of the microporous sheet is left exposed;
　contacting the exposed portion of the microporous sheet with a material sample such that at least a portion of the material sample is drawn into the microporous sheet;
　transmitting electromagnetic radiation emitted from the material sample in the microporous sheet to a detector;
　piercing a patient's skin with a skin-piercing structure, the skin-piercing structure having a passageway that connects a distal portion of the skin-piercing structure with the exposed portion of the microporous sheet; and
　analyzing the electromagnetic radiation emitted from the material sample in a spectral region of interest.

99. The method of claim 98, wherein the exposed portion of the microporous sheet comprises an entry region through which the material sample can enter the microporous sheet.

100. The method of claim 98, wherein the first and second planar support members comprise members having a structural rigidity greater than or equal to a structural rigidity of the microporous sheet.

101. The method of claim 98, wherein the microporous sheet comprises a non-solid material having a network of voids through which the material sample can propagate.

102. The method of claim 98, further comprising determining the baseline transmittance of the microporous sheet before contacting the material sample to the microporous sheet.

103. The method of claim 98, wherein the material sample is a biological fluid.

104. The method of claim 98, wherein the microporous sheet has four side surfaces, and the first and second support members are substantially coextensive with at least two of the side surfaces of the microporous sheet.

105. The method of claim 104, wherein the first and second support members are substantially coextensive with all four of the side surfaces of the microporous sheet.

106. The method of claim 98, wherein the exposed portion of the microporous sheet has a structured surface.

107. The method of claim 98, wherein the microporous sheet comprises a polymeric, non-woven material.

108. An analyte detection system for determining the concentration of analyte in a biological fluid sample drawn from a patient, the system comprising:

a source configured to emit electromagnetic radiation;

a detector positioned to receive at least a portion of the electromagnetic radiation emitted from the source;

a sample element configured to hold the biological fluid sample in a sample cell that is defined by a window, wherein the window is highly transmissive of infrared radiation, and a microporous sheet positioned in the sample cell wherein at least a portion of the sheet is an exposed transit opening configured to receive and distribute the biological fluid sample;

a sample supply passage extending from a skin-piercing structure to the exposed transit opening; and a filter positioned in the sample supply passage to filter the biological sample;

wherein the detection system performs optical analysis on the biological sample to assess the concentration of at least one constituent of the biological sample.

109. The system of claim 108, wherein the microporous sheet comprises a non-solid material having a network of voids through which the material sample can propagate.

110. The system of claim 108, wherein the microporous sheet has a void volume of greater than about 20%.

111. The system of claim 108, wherein the microporous sheet has an average baseline transmittance of at least 1 percent.

112. The system of claim 108, wherein the sample element is configured to be removably positioned within an optical path extending from the source to the detector.

113. The system of claim 108, wherein the sample cell is reagentless.

114. The system of claim 108, wherein the skin-piercing structure forms a part of the sample element.

115. The system of claim 108, further comprising an optical filtering system that allows at least one wavelength between about 3.5 $\mu$m and about 14 $\mu$m to pass through the sample cell.

* * * * *

UNITED STATES PATENT AND TRADEMARK OFFICE
CERTIFICATE OF CORRECTION

| | |
|---|---|
| PATENT NO. | : 6,983,177 B2 |
| APPLICATION NO. | : 10/337226 |
| DATED | : January 3, 2006 |
| INVENTOR(S) | : Peter Rule et al. |

It is certified that error appears in the above-identified patent and that said Letters Patent is hereby corrected as shown below:

In Column 43, Line 14, Claim 32, delete "art" and insert --an--, therefor.

Signed and Sealed this

Third Day of October, 2006

JON W. DUDAS
*Director of the United States Patent and Trademark Office*